United States Patent

Harris et al.

[11] Patent Number: 6,150,373
[45] Date of Patent: Nov. 21, 2000

[54] BICYCLIC NITROGEN HETEROCYCLES

[75] Inventors: William Harris, Henlow; Christopher Huw Hill, Baldock; Ian Edward David Smith, Willington, all of United Kingdom

[73] Assignee: Hoffmann-La Roche Inc., Nutley, N.J.

[21] Appl. No.: 09/422,451

[22] Filed: Oct. 21, 1999

[30] Foreign Application Priority Data

Oct. 23, 1998 [GB] United Kingdom .................... 9823277
Aug. 24, 1999 [GB] United Kingdom .................... 9920044

[51] Int. Cl.$^7$ ........................ A01N 43/54; A61K 31/505; C07D 487/00
[52] U.S. Cl. ............................. 514/258; 544/256
[58] Field of Search ............................. 544/256; 514/258

[56] References Cited

U.S. PATENT DOCUMENTS 5,654,307  8/1997  Bridges et al. ........................ 514/258

FOREIGN PATENT DOCUMENTS

WO 96 34867  11/1996  WIPO .
WO 98/11095   3/1998  WIPO .
WO 98/28281   7/1998  WIPO .
WO 99/61444  12/1999  WIPO .

*Primary Examiner*—Mukund J. Shah
*Assistant Examiner*—Tamthom N. Truong
*Attorney, Agent, or Firm*—George W. Johnston; William H. Epstein; Lewis J. Kreisler

[57] ABSTRACT

Amino-substituted dihydropyrimido[4,5-d]pyrimidinones of the formula

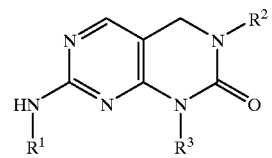

(I)

in which $R^1$ represents hydrogen, lower alkyl, aryl, aryl-lower alkyl, heteroaryl, heteroaryl-lower alkyl, lower cycloalkyl or lower cycloalkyl-lower alkyl, $R^2$ represents lower alkyl, aryl, aryl-lower alkyl, heteroaryl, heteroaryl-lower alkyl, lower cycloalkyl or lower cycloalkyl-lower alkyl, and $R^3$ represents hydrogen, lower alkyl, aryl, aryl-lower alkyl, heteroaryl, heteroaryl-lower alkyl, lower cycloalkyl, lower cycloalkenyl or lower cycloalkyl-lower alkyl, and pharmaceutically acceptable salts thereof are protein kinase inhibitors. They can be used in the treatment or prophylaxis of inflammatory, immunological, oncological, bronchopulmonary, dermatological and cardiovascular disorders, in the treatment of asthma, central nervous system disorders or diabetic complications or for the prevention of graft rejection following transplant surgery.

16 Claims, No Drawings

BICYCLIC NITROGEN HETEROCYCLES

SUMMARY OF THE INVENTION

The present invention relates to bicyclic nitrogen heterocycles. More particularly, the invention is concerned with amino-substituted dihydropyrimido[4,5-d]pyrimidinone derivatives, a process for their manufacture and pharmaceutical preparations containing them.

The amino-substituted dihydropyrimido[4,5-d] pyrimidinone derivatives provided by the present invention are compounds of the formula

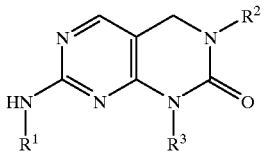

(I)

wherein
- $R^1$ represents hydrogen, lower alkyl, aryl, aryl-lower alkyl, heteroaryl, heteroaryl-lower alkyl, lower cycloalkyl or lower cycloalkyl-lower alkyl,
- $R^2$ represents lower alkyl, aryl, aryl-lower alkyl, heteroaryl, heteroaryl-lower alkyl, lower cycloalkyl or lower cycloalkyl-lower alkyl, and
- $R^3$ represents hydrogen, lower alkyl, aryl, aryl-lower alkyl, heteroaryl, heteroaryl-lower alkyl, lower cycloalkyl, lower cycloalkenyl or lower cycloalkyl-lower alkyl, and pharmaceutically acceptable salts of basic compounds of formula I with acids, or pharmaceutically acceptable salts of acidic compounds of formula I with bases.

The compounds of formula I and their aforementioned salts are inhibitors of the T-cell tyrosine kinase $p56^{lck}$ as determined by the assay described below. Inhibition of $p56^{lck}$ is known to down-regulate T-cell activation, leading to immunosuppression and decreased inflammation. They can accordingly be used in the treatment or prophylaxis of inflammatory and immunological responses.

DETAILED DESCRIPTION OF THE INVENTION

As used herein, the term "lower alkyl", alone or in combination as in "aryl-lower alkyl", "heteroaryl-lower alkyl" and "lower cycloalkyl-lower alkyl", means a straight-chain or branched-chain alkyl group containing from 1 to 7, preferably from 1 to 4, carbon atoms, such as methyl, ethyl, n-propyl, isopropyl, n-butyl, sec.butyl, tert.butyl, n-pentyl, n-hexyl, n-heptyl and the like.

The term "lower alkoxy" means a lower alkyl group as defined earlier which is bonded via an oxygen atom, with examples of lower alkoxy groups being methoxy, ethoxy, n-propoxy, isopropoxy, n-butoxy, sec.butoxy, tert.butoxy, n-pentoxy and the like.

The term "lower cycloalkyl", alone or in combination as in "lower cycloalkyl-lower alkyl", means a cycloalkyl group containing from 3 to 7, preferably from 4 to 6, carbon atoms, i.e. cyclopropyl, cyclobutyl, cyclopentyl, cyclohexyl or cycloheptyl.

The term "lower cycloalkenyl" means a cycloalkenyl group containing from 4 to 7 carbon atoms, e.g. cyclobutenyl, cyclopentenyl, cyclohexenyl and the like.

The term "aryl", alone or in combination as in "aryl-lower alkyl", means a phenyl or naphthyl group which is unsubstituted or optionally mono- or multiply-substituted by halogen, lower alkyl, lower alkoxy, lower-alkoxy lower alkyl, trifluoromethyl, hydroxy, hydroxy lower-alkyl, carboxylic acid, carboxylic ester, nitro, amino, or phenyl, particularly by halogen, lower alkyl, lower alkoxy, trifluoromethyl, hydroxy, nitro, amino and phenyl, wherein the substituents may be the same or different, and/or by a group of the formula —Z—$NR^4R^5$ or —Z—$OR^6$ in which Z represents a spacer group and $R^4$ and $R^5$ each individually represent hydrogen or lower alkyl or $R^4$ and $R^5$ together with the nitrogen atom to which they are attached represent a 4-, 5- or 6-membered saturated or partially unsaturated or 5- or 6-membered aromatic heterocyclic group which contains one or more hetero atoms selected from nitrogen, sulfur and oxygen and which is optionally substituted by lower alkyl, lower alkoxy and/or oxo and/or which is optionally benz-fused, and in which $R^6$ is defined as H or lower-alkyl, preferably H. As used herein, the term "spacer group" means —$(CH_2)_m$— in which m stands for 1, 2, 3 or 4 and —$O(CH_2)_n$— in which n stands for 2, 3 or 4. The carbon atoms of the —$(CH_2)_m$ chain may be unsubstituted or optionally mono- or di-substituted by lower-alkyl, hydroxy lower-alkyl or lower-alkyloxy lower-alkyl, wherein the substituents may be the same or different. Pyrrolidinyl, piperidinyl, piperazinyl, morpholinyl and indolyl are examples of heterocyclyl groups formed by $R^4$ and $R^5$ together with the nitrogen atom to which they are attached. Thus, the term "aryl" embraces groups such as phenyl, 1-naphthyl, 2-hydroxyphenyl, 3-bromophenyl, 4-methoxyphenyl, 2,6-difluorophenyl, 2,6-dichlorophenyl, 3-(2-aminoethyl)-phenyl, 4-(2-hydroxyethyl)-phenyl, 4-(2-diethylaminoethoxy)-phenyl, 3-(2-phthalimidoethyl)-phenyl and the like.

The term "heteroaryl", alone or in combination as in "heteroaryl-lower alkyl", means a 5- or 6-membered heteroaromatic group which contains one or more hetero atoms selected from N, S and O and which may be benz-fused and/or substituted in the same manner as "aryl" defined earlier. Examples of typical heteroaryl groups are thienyl, furyl, pyridyl, pyrimidinyl, quinolyl, indolyl, benzofuranyl, imidazole, 1,2,3-triazole, 1,2,4-triazole, tetrazole, thiazole, pyridine-N-oxide and the like.

The term "halogen" means fluorine, chlorine, bromine or iodine.

A preferred class of compounds provided by the present invention comprises those of the formula

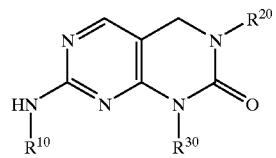

(Ia)

wherein $R^{10}$ represents lower alkyl, aryl or aryl-lower alkyl, $R^{20}$ represents aryl and $R^{30}$ represents hydrogen, lower alkyl, aryl or aryl-lower alkyl.

Preferred compounds falling under formula Ia have the formula

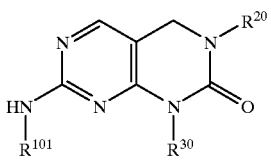

(Iai)

wherein $R^{101}$ represents aryl and $R^{20}$ and $R^{30}$ have the significance given earlier.

$R^{101}$ preferably represents phenyl. $R^{20}$ preferably represents halophenyl, especially 2,6-dichlorophenyl. $R^{30}$ preferably represents phenyl substituted by a group of the formula —Z—NR$^4$R$^5$ defined hereinbefore.

Another preferred class of compounds provided by the present invention comprises those of the formula

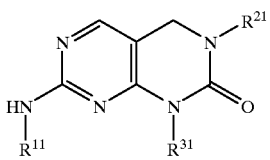

(Ib)

wherein $R^{11}$ represents lower alkyl, $R^{21}$ represents aryl and $R^{31}$ represents heteroaryl-lower alkyl. $R^{11}$ preferably represents isopropyl and $R^{21}$ preferably represents halophenyl.

1-[3-(2-Aminoethyl)phenyl]-7-anilino-3-(2,6-dichlorophenyl)-3,4-dihydropyrimido-[4,5-d]pyrimidin-2(1H)-one is a particularly preferred compound of formula I.

Other representative compounds of the present invention are 3-(2,6-dichlorophenyl)-7-[4-[2-(diethylamino)ethoxy]anilino]-3,4-dihydro-1-methylpyrimido[4,5-d]pyrimidin-2(1H)-one, 3-(2,6-dichlorophenyl)-7-[4-[2-(diethylamino)ethoxy]anilino]-3,4-dihydro-1-phenylpyrimido[4,5-d]pyrimidin-2(1H)-one, 1-benzyl-3-(2,6-dichlorophenyl)-7-[4-[2-(diethylamino)ethoxy]anilino]-3,4-dihydropyrimido[4,5-d]pyrimidin-2(1H)-one, 3-(2,6-dichlorophenyl)-7-[4-[2-(diethylamino)ethoxy]anilino]-3,4-dihydro-1-[( 3-pyridyl)-methyl]pyrimido[4,5-d]pyrimidin-2(1H)-one, 3-(2,6-dichlorophenyl)-3,4-dihydro-1-phenyl-7-[(4-pyridyl)amino]pyrimido[4,5-d]pyrimidin-2(1H)-one, 7-[4-[2-(diethylamino)ethoxy]anilino]-3-(2,6-difluorophenyl)-3,4-dihydro-1-methylpyrimido[4,5-d]pyrimidin-2(1H)-one, 3-(2,4-dichlorophenyl)-7-[4-[2-(diethylamino)ethoxy]anilino]-3,4-dihydro-1-methylpyrimido[4,5-d]pyrimidin-2(1H)-one and 3-(2,6-dichlorophenyl)-1-[2-cyclohexen-1(RS)-yl]-7-[4-[2-(diethylamino)ethoxy]-anilino]-3,4-dihydropyrimido[4,5-d]pyrimidin-2(1H)-one.

Other preferred compounds are

1-[3-(2-aminoethyl)phenyl]-7-anilino-3-(2-bromophenyl)-3,4-dihydropyrimido[4,5-d]pyrimidin-2(1H)-one, 1-[3-(2-aminoethyl)phenyl]-7-anilino-3,4-dihydro-3-(2,6-dimethylphenyl)-pyrimido[4,5-d]pyrimidin-2(1H)-one, 3-(2-bromophenyl)-7-[4-[2-(diethylamino)ethoxy]anilino]-3,4-dihydro-1-[3-(2-hydroxyethyl)phenyl]pyrimido[4,5-d]pyrimidin-2(1H)-one, 1-[3-((2-amino-1,1-dimethyl)ethyl)phenyl]-7-anilino-3-(2-bromophenyl)-3,4-dihydropyrimido[4,5-d]pyrimidin-2(1H)-one, 1-[3-(2-aminoethyl)phenyl]-3-(2-bromophenyl)-7-(4-methoxyanilino)-3,4-dihydropyrimido[4,5-d]pyrimidin-2(1H)-one, 7-anilino-3-(2-bromophenyl)-3,4-dihydro-1-[4-(hydroxymethyl)phenyl]-pyrimido[4,5-d]pyrimidin-2(1H)-one, 1-[4-(aminomethyl)phenyl]-7-anilino-3-(2-bromophenyl)-3,4-dihydropyrimido[4,5-d]pyrimidin-2(1H)-one, 7-anilino-3-(2,6-dichlorophenyl)-3,4-dihydro-1-[3-[2-(methylamino)ethyl]-phenyl]pyrimido[4,5-d]pyrimidin-2(1H)-one, 7-anilino-3-(2,6-dichlorophenyl)-3,4-dihydro-1-[3-[2-(dimethylamino)ethyl]phenyl]-pyrimido[4,5-d]pyrimidin-2(1H)-one, 1-[3-(2-aminoethyl)phenyl]-7-anilino-3-(2,4-dichlorophenyl)-3,4-dihydropyrimido[4,5-d]pyrimidin-2(1H)-one, 7-anilino-3-(2,4-dichlorophenyl)-3,4-dihydro-1-[3-[2-(methylamino)ethyl]phenyl]-pyrimido[4,5-d]pyrimidin-2(1H)-one, 1-[4-(2-aminoethyl)phenyl]-7-anilino-3-(2,4-dichlorophenyl)-3,4-dihydropyrimido[4,5-d]pyrimidin-2(1H)-one, 3-(2,4-dichlorophenyl)-7-[4-[2-(diethylamino)ethoxy]anilino]-3,4-dihydro-1-[3-(2-hydroxyethyl))phenyl]pyrimido[4,5-d]pyrimidin-2(1H)-one, 3-(2,4-dichlorophenyl)-7-[4-[2-(diethylamino)ethoxy]anilino]-3,4-dihydro-1-[3-(2-(dimethylamino)ethyl)phenyl]pyrimido[4,5-d]pyrimidin-2(1H)-one and 1-[3-(1-aminomethyl-1-ethyl-propyl)-phenyl]-3-(2,6-dichloro-phenyl)-7-phenylamino-3,4-dihydropyrimido[4,5-d]pyrimidin-2(1H)-one.

According to the process provided by the present invention, the aforementioned amino-substituted dihydropyrimido[4,5-d]pyrimidinone derivatives are manufactured by (a) reacting a compound of the formula

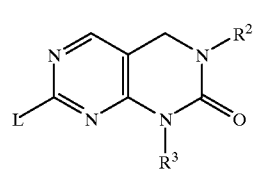

(II)

wherein $R^2$ and $R^3$ have the significance given earlier with the proviso that any hydroxy, amino or carboxylic acid group present may be in protected form, and L signifies benzyl sulfonyl or lower alkanesulfonyl, with an amine of the formula $R^1$—NH$_2$    (III)

wherein $R^1$ has the significance given earlier, with the proviso that any hydroxy, amino or carboxylic acid group present may be in protected form, and, where required, converting a protected hydroxy or protected amino or protected carboxylic acid group present in the reaction product into a free hydroxy or free amino or free carboxylic acid group, or b) for the manufacture of a compound of formula I in which $R^1$ represents hydrogen, cleaving off the aryl-methyl group from a compound of formula I in which $R^1$ signifies aryl-methyl, and c) if desired, converting a basic compound of formula I obtained into a pharmaceutically acceptable salt with an acid, or converting an acidic compound of formula I obtained into a pharmaceutically acceptable salt with a base.

A protected hydroxy or protected amino or protected carboxylic acid group present in a starting material of formula II or III, i.e. on an aryl or heteroaryl substituent $R^1$, $R^2$ and/or $R^3$, can be any conventional protected hydroxy or protected amino or protected carboxylic acid group. Thus, for example, a hydroxy group can be protected in the form of an ether, e.g. the methyl ether, or an ester, e.g. the ethyl ester. With respect to protected amino, phthalimido is an example of such a group. An example of a protected carboxylic acid is an ester, e.g. methyl ester.

The requirement for protecting groups obviously depends on the chemistry that is to be performed. For preparation of compounds of formula I by reaction of compounds of formula II with those of formula III, a primary or secondary aliphatic amino group in R1 must be protected, unless the compound of formula III is symmetrical. An aromatic amino group in R1 only requires protection when the reacting R1—$NH_2$ is also an aromatic amine and R1—$NH_2$ is not symmetrical. Hydroxy or carboxylic acid groups in R1, R2 or R3 do not need to be protected. Primary or secondary amino groups in R2 and R3 must be protected. Those groups that do not require protection for this reaction may be in protected form as a consequence of the preceding chemistry, and may optionally be carried through in their protected form. For the preceding chemistry, the requirement for protecting groups depends on the synthetic steps and is apparent to a practising chemist.

To illustrate the use of protecting groups, an amino group present in R1 maybe protected as it's tert-butyl carbamate so that it does not interfere when reacting a compound of formula (III) with a compound of formula (II). This protecting group may also be used for an amino group present in R3 when reaction Scheme II is utilised. A phthalimido protected amino group may also be introduced into R3 following the cyclisation step of Scheme I. Phenolic hydroxyl groups, which may be present in R1, R2 or R3, can conveniently be protected as their methyl ethers which survive the chemistry employed in Schemes I and II. Aliphatic hydroxyl groups in R3 may be protected as tert-butyl diphenyl silyl ethers in Scheme I, immediately prior to reaction with a compound of formula (IX). Examples 66 and 67 illustrate the protection of a carboxylic acid in R3 as it's methyl ester, where R3 is introduced via alkylation of a dihydropyrimido[4,5-d]pyrimidinone.

The reaction of a compound of formula II with an amine of formula III in accordance with embodiment (a) of the process can be carried out in the presence or absence of a solvent. When a solvent is used, this can conveniently be a halogenated aliphatic hydrocarbon, e.g. dichloromethane or 1,2-dichloroethane, an open-chain ether, e.g. diethyl ether or diisopropyl ether, a cyclic ether, e.g. tetrahydrofuran, an optionally halogenated aromatic hydrocarbon, e.g. benzene, toluene, a xylene or chlorobenzene, or a formamide, e.g. dimethylformamide. Suitably, the reaction is carried out at a temperature in the range of about 0° C. to about 200° C., preferably at about 100° C. to about 200° C.

The conversion of a protected hydroxy group or a protected amino or a protected carboxylic acid group present in a product obtained by reacting a compound of formula II with an amine of formula III can be carried out in a manner known per se. Thus, for example, an ether such as the methyl ether can be converted into hydroxy by treatment with hydrobromic acid and an ester such as the ethyl ester can be converted into hydroxy using an alkali metal aluminium hydride such as lithium aluminium hydride. Again, for example, the phthalimido group can be converted into amino by treatment with hydrazine hydrate. The ester, e.g. methyl ester can, in turn, be converted into carboxylic acid, for example, by reacting with an alkali metal hydroxide.

Deprotection is necessary when the required product is the free hydroxy, amino, or carboxylic acid. For example, the product of Example 66 is a carboxylic ester and claimed as such, but can also be considered a protected form of the carboxylic acid (Example 67). The group "lower alkoxy" could be regarded as "a protected hydroxy" which would require no deprotection but "hydroxy" or "hydroxy lower-alkyl" in "aryl" need deprotection. Similarly, the phthalimido compound of Example 37 can be regarded as a protected amino group which would require no deprotection.

The cleavage of an aryl-methyl group, e.g. lower-alkoxybenzyl such as 4-methoxybenzyl, from a compound of formula I in which $R^1$ signifies aryl-methyl in accordance with embodiment (b) of the process can be carried out using methods which are known per se. For example, the cleavage can be carried out using trifluoroacetic acid, conveniently at an elevated temperature, preferably at the reflux temperature of the reaction mixture.

Compounds of formula I which are basic can form salts with inorganic acids, e.g. hydrohalic acids such as hydrochloric acid or hydrobromic acid, sulfuric acid, nitric acid or phosphoric acid, or with organic acids, e.g. formic acid, acetic acid, trifluoroacetic acid, citric acid, fumaric acid, malic acid, maleic acid, succinic acid, tartaric acid, salicylic acid, methanesulfonic acid, ethanesulfonic acid, 4-toluenesulfonic acid and the like. Compounds of formula I which are acidic can form salts with bases e.g. metals or amines, such as alkali and alkaline earth metals or organic amines The basic or acidic nature of the compounds is determined by the presence of basic or acidic groups contained in R1, R2 or R3. The compound produced in Example 67 is acidic. The compounds produced in Examples 11–14, 16–21, 23, 24, 32–34, 37, 38, 46, 47, 49, 53, 57, 62, 63, 65, 66, 68, 69, 72, 76, and 90–92 are neutral. The compounds produced in the remainder of the examples are basic. Examples of metals used as cations are sodium, potassium, magnesium, calcium and the like. Examples of suitable amines are ethylenediamine, monoethanolamine, diethanolamine and the like. In accordance with embodiment (c) of the process, these salts can be formed and isolated in a manner known per se. Salts of basic compounds of formula I with acids are preferred.

The starting materials of formula II are novel and also form an object of the present invention. They can be prepared as illustrated in Scheme I hereinafter in which $R^2$ and $R^3$ have the significance given earlier, subject to the foregoing proviso and $R^7$ represents lower alkyl or benzyl.

Scheme I

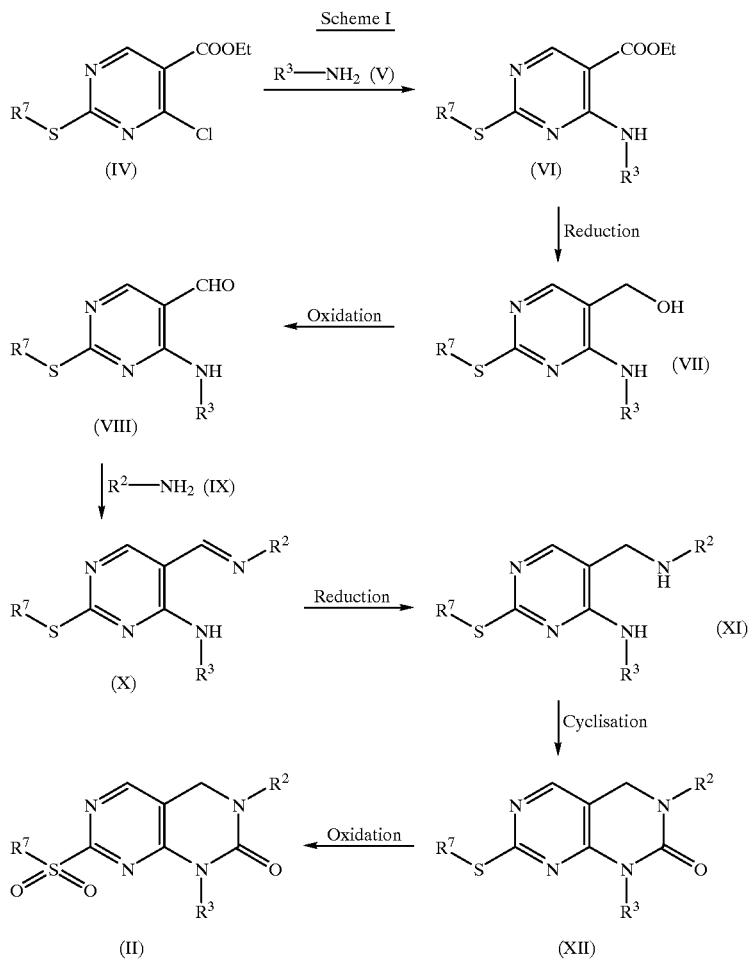

Having regard to Scheme I, in the first step a compound of formula IV is reacted with a compound of formula V to give a compound of formula VI. This reaction is conveniently carried out in a solvent which is inert under the reaction conditions, preferably a halogenated aliphatic hydrocarbon, especially dichloromethane, an optionally halogenated aromatic hydrocarbon, an open-chain or cyclic ether, a formamide or a lower alkanol. Suitably, the reaction is carried out at about −20° C. to about 120° C.

The next step comprises the reduction of a compound of formula VI to give an alcohol of formula VII. This reduction is carried out using lithium aluminium hydride in a manner known per se, e.g. in a solvent which is inert under the conditions of the reduction, preferably an open-chain or cyclic ether, especially tetrahydrofuran, at about −20° C. to about 70° C., preferably at about 0° C. to about room temperature.

Oxidation of an alcohol of formula VII in the next step yields a carboxaldehyde of formula VIII. This oxidation is carried out with manganese dioxide in a manner known per se, conveniently in a solvent which is inert under the oxidation conditions, preferably a halogenated aliphatic hydrocarbon, especially dichloromethane, or an optionally halogenated aromatic hydrocarbon. Suitably, the oxidation is carried out at about 0° C. to about 60° C.

Reaction of a carboxaldehyde of formula VIII with an amine of formula IX in the next step yields a compound of formula X. This reaction may be carried out in the presence of an acid, e.g. an aromatic sulfonic acid, preferably 4-toluenesulfonic acid, with azeotropic removal of the water formed during the reaction. Conveniently, the reaction is carried out in a solvent which is inert under the reaction conditions, preferably an optionally halogenated aromatic hydrocarbon, especially toluene, and at a temperature of about 70° C. to about 150° C., especially at the reflux temperature of the solvent.

The next step comprises the reduction of a compound of formula X to give a compound of formula XI. This reduction is carried out using sodium borohydride, lithium aluminium hydride or sodium triacetoxyborohydride in a manner known per se. Preferably, the compound of formula X is not purified, but rather the reaction mixture in which it is prepared is concentrated and the concentrate obtained is taken up in a solvent which is inert under the conditions of the reduction, preferably an open-chain or cyclic ether, especially tetrahydrofuran or an optionally halogenated aromatic hydrocarbon or a lower alkanol, and then treated with an aforementioned reducing agents. The reduction is suitably carried out at about 0° C. to about 100° C., preferably at about 25° C.

Cyclisation of a compound of formula XI yields a compound of formula XII. This cyclisation is effected by reaction with phosgene or trichloromethyl chloroformate in a manner known per se, conveniently in the presence of a tertiary organic base, preferably a tri(lower alkyl)amine, especially triethylamine, and in a solvent which is inert under the conditions of the reaction, preferably an open-chain or cyclic ether, especially tetrahydrofuran, an optionally halogenated aromatic hydrocarbon or a halogenated aliphatic hydrocarbon. Conveniently, the reaction is carried out at about −20° C. to about 50° C., preferably at about 0° C. to about room temperature.

Oxidation of a compound of formula XII with 3-chloroperbenzoic acid yields a starting material of formula II. This oxidation is carried out in a manner known per se, conveniently in a solvent which is inert under the conditions of the oxidation, preferably a halogenated aliphatic hydrocarbon, especially dichloromethane, and at about −20° C. to about 50° C., preferably about 0° C. to about room temperature.

Compounds of formula XII in Scheme I or starting materials of formula II in which $R^3$ represents hydrogen can be N-substituted by treatment with an alkali metal hydride, especially sodium hydride, and subsequent reaction with a compound of the formula $$R^{3a}\text{—L} \tag{XIII}$$

wherein $R^{3a}$ has any of the values accorded to $R^3$ hereinbefore except hydrogen, aryl or heteroaryl and L represents a leaving group.

The leaving group denoted by L in a compound of formula XIII can be, for example, halo, lower alkanesulfonate, e.g. methanesulfonate, trifluoromethanesulfonate or aromatic sulfonate, e.g. benzenesulfonate or 4-toluenesulfonate. L preferably represents iodo.

The N-substitution is conveniently carried out in a solvent which is inert under the reaction conditions, preferably a formamide, especially dimethylformamide, an open-chain or cyclic ether or an optionally halogenated aromatic hydrocarbon. Suitably, the reaction is carried out at about 50° C. to about 200° C., preferably at about 50° C. to about 150° C.

Furthermore, compounds of formula XII in scheme I or starting materials of formula II in which $R^3$ signifies aryl substituted by a group of the formula —$(CH_2)_m$—$NR^4R^5$, wherein $NR^4R^5$ signifies phthalimido and m has the significance given earlier, can be prepared by cyclising a compound of formula XI in which $R^3$ signifies aryl substituted by a group of the formula —$(CH_2)_m$—OH, wherein m has the significance given earlier, with phosgene and treating the reaction product (a compound corresponding to formulae XII or II in which $R^3$ signifies aryl substituted by a group of the formula —$(CH_2)_m$—Cl, wherein m has the significance given earlier) with an alkali metal salt of phthalimide, preferably the potassium salt.

Furthermore, compounds of formula XII in scheme I, starting materials of formula II, or compounds of formula I where any of $R^1$–$R^3$ contain aryl substituted by a group Z—$NR^4R^5$ may be prepared from the corresponding compounds substituted by Z—OH by standard methods, for example by activation as the methanesulfonate or toluenesulfonate, and reaction with an amine $HNR^4R^5$, or by reaction with $HNR^4R^5$ under Mitsunobu conditions.

When any of $R^1$–$R^3$ include a nitrogen-containing heteroaryl group, the process may lead to N-oxide formation. The N-oxides can be converted to the free N compounds by standard methods, for example, by reaction with triphenyl phosphine.

In an alternative procedure for the preparation of compounds of formula VI in Scheme I in which $R^3$ represents hydrogen, ethyl 4-amino-2-mercapto-pyrimidine-5-carboxylate of the formula

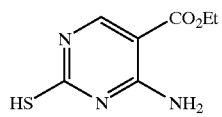

(XIV)

can be reacted with a compound of the formula $$R^7\text{—L} \tag{XV}$$

wherein $R^7$ has the significance given earlier, and wherein L has the same significance as given for structure XIII.

The reaction of the compound of formula XIV with a compound of formula XV is conveniently carried out in a solvent which is inert under the reaction conditions, preferably a ketone, especially acetone, a halogenated aliphatic hydrocarbon, an optionally halogenated aromatic hydrocarbon, an open-chain or cyclic ether or a formamide. Suitably, the reaction is effected at about −20° C. to about 100° C., preferably at about 20° C.

The compounds of formulae IV, XIII, XIV and XV hereinbefore are known compounds or analogues of known compounds. A compound of formula IV, where $R^7$ is methyl is commercially available from Sigma-Aldrich Company Ltd. or, where $R^7$ is benzyl, may be synthesised as described by Peters, E. et al.; J.Amer.Chem.Soc., 64, 794–795, 1942. Compound XIV is commercially available from Lancaster Synthesis Ltd. Compounds of formula XIII and XV are commercially available, for example, when L is halogen like methyl and ethyl iodide or benzyl bromide from Sigma-Aldrich Company Ltd. or, where L is a sulfonate like n-butyl methanesulfonate or ethyl 4-toluenesulfonate from Lancaster Synthesis Ltd.

The amine starting materials of formulae III, V and IX hereinbefore, insofar as they are not known compounds or analogues of known compounds, can be prepared in a similar manner to the known compounds or as illustrated in the following Examples. In particular, compounds of formulae III, V and IX are commercially available, for example, from Sigma-Aldrich Company Ltd. or Lancaster Synthesis Ltd., or may be synthesised by standard methods as illustrated in Examples 1, 15, 16, 27, 37, 57, 61, 63, 77, 84, and 85. Generally, the aromatic and heteroaromatic amines can be prepared, for example, from the corresponding nitro compounds by reduction with, for example, Raney Nickel, or by catalytic hydrogenation. The nitro compounds in turn may be prepared by nitration of an aromatic or heteroaromatic compound. Alkyl amines, including those that contain aromatic or heteroaromatic groups, can be prepared, for example, by reacting the corresponding compounds bearing a leaving group with ammonia or a group such as azide that can be converted to an amine by known methods. Examples of such leaving groups are sulfonates, prepared in turn from the corresponding alcohols, or halides. Alternatively, the alkyl amines may be prepared from cyano compounds by reduction. Therefore, the amines are accessible, for example, from commercially available alcohols, halides and nitrites.

The intermediates of formula XI in Scheme I may also be prepared as illustrated in Scheme II, in which $R^2$, $R^3$ and $R^7$ have the significance given earlier. $R^8$ is either ethyl or 4-methoxybenzyl.

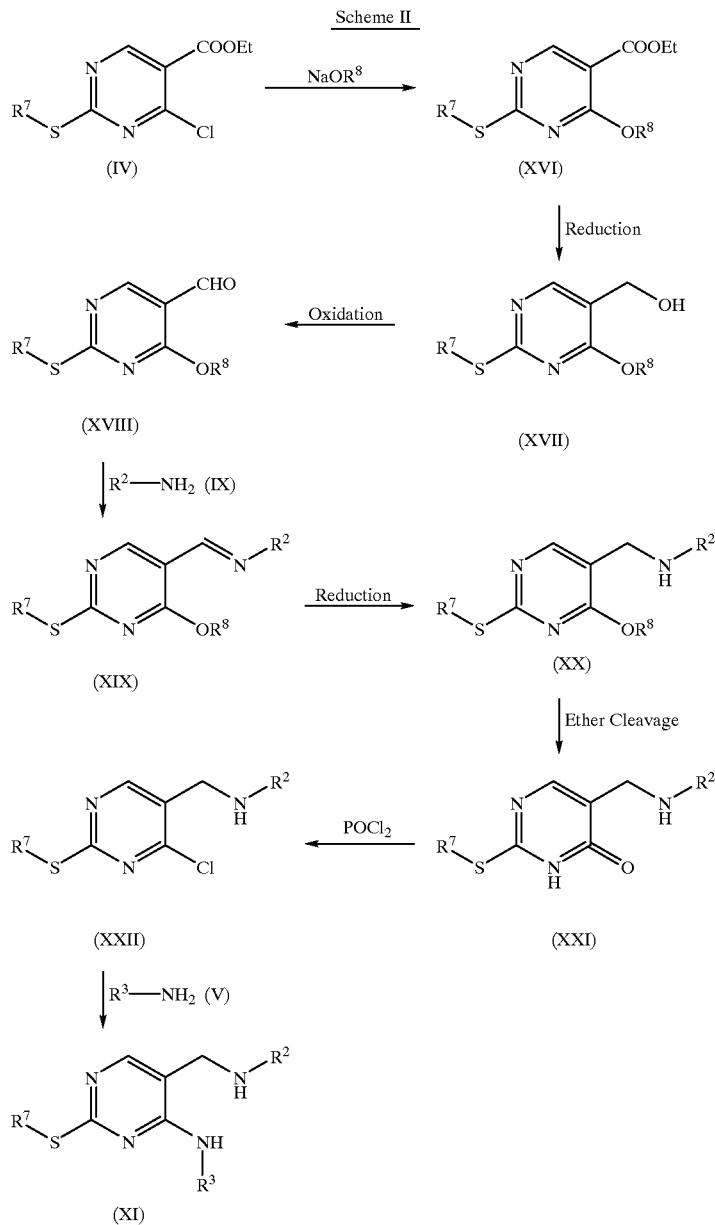

Scheme II

Having regard to Scheme II, in the first step a compound of formula (IV) is reacted with either sodium ethoxide in ethanol, or the sodium salt of 4-methoxy benzyl alcohol in tetrahydrofuran, at a temperature of about 0C to about room temperature, to give a compound of formula (XVI).

In the next step compound (XVI) is reduced to an alcohol of formula (XVII). The reaction is carried out with di-isobutyl aluminium hydride or lithium aluminium hydride in a manner known per se, in a solvent that is inert under the reaction conditions, preferably a halogenated aliphatic hydrocarbon, especially dichloromethane, or an open-chain or cyclic ether, especially tetrahydrofuran. Suitably, the reaction is conducted at a temperature of about −78° C. to about room temperature.

Oxidation of an alcohol of formula (XVII) yields a carboxaldehyde of formula (XVIII). This oxidation is carried out with manganese dioxide in a manner known per se, conveniently in a solvent which is inert under the oxidation conditions, preferably a halogenated aliphatic hydrocarbon, especially dichloromethane, or an optionally halogenated aromatic hydrocarbon. Suitably, the oxidation is carried out at about 0° C. to about 60° C.

Reaction of a carboxaldehyde of formula (XVIII) with an amine of formula (IX) in the next step yields a compound of formula (XIX). This reaction may be carried out in the presence of an acid, e.g. an aromatic sulfonic acid, preferably 4-toluenesulfonic acid, with azeotropic removal of the water formed during the reaction. Conveniently, the reaction is carried out in a solvent which is inert under the reaction conditions, preferably an optionally halogenated aromatic hydrocarbon, especially toluene, and at a temperature of about 70° C. to about 150° C., especially at the reflux temperature of the solvent.

The next step comprises the reduction of a compound of formula (XIX) to give a compound of formula (XX). This reduction is carried out using sodium borohydride, lithium aluminium hydride or sodium triacetoxy borohydride in a manner known per se. Preferably, the compound of formula (XIX) is not purified, but rather the reaction mixture in which it is prepared is concentrated and the concentrate obtained is taken up in a solvent which is inert under the conditions of the reduction, preferably an open-chain or cyclic ether, especially tetrahydrofuran or an optionally halogenated aromatic hydrocarbon or a lower alkanol, and then treated with an aforementioned reducing agent. Alternatively, the reaction mixture containing compound (XIX) may be added without concentration to a solution of one of the aforementioned reducing agents in a solvent which is inert under the conditions of the reduction, preferably an open-chain or cyclic ether, especially tetrahydrofuran or an optionally halogenated aromatic hydrocarbon or a lower alkanol.

In the ether cleavage step, a compound of formula (XX) is reacted with concentrated sulfuric acid, where $R^8$ is ethyl, or with trifluoroacetic acid, where $R^8$ is 4-methoxybenzyl, to give a pyridone of formula (XXI). The reaction is carried out using the reagent as solvent. In the case of sulfuric acid, the reaction is conducted at about 120° C., and in the case of trifluoroacetic acid at its reflux temperature.

Reaction of a compound of formula (XXI) with phosphorus oxychloride in the next step gives a compound of formula (XXII). The reaction is carried out using phosphorus oxychloride as the solvent at a temperature of about 100° C.

A chloride of formula (XXII) is reacted with a compound of formula (V) to give the intermediate (XI). The reaction can be carried out in the presence or absence of a solvent. When a solvent is used, this can conveniently be a halogenated aliphatic hydrocarbon, e.g. dichloromethane or 1,2-dichloroethane, an open-chain ether, e.g. diethyl ether or diisopropyl ether, a cyclic ether, e.g. tetrahydrofuran, an optionally halogenated hydrocarbon, e.g. benzene, toluene, xylene or chlorobenzene, or a formamide, e.g. dimethyl formamide. The reaction is conducted in the presence of a base, especially a tertiary amine, e.g. diethylaniline. Suitably, the reaction is carried out at a temperature in the range of about 0° C. to about 200° C., preferably at about 100° C. to about 200° C.

As mentioned earlier, the compounds of formula I, the pharmaceutically acceptable salts of basic compounds of formula I with acids, and the pharmaceutically acceptable salts of acidic compounds of formula I with bases, are all inhibitors of the T-cell tyrosine kinase p56$^{lck}$ which will down-regulate T-cell activation leading to immunosuppression and decrease inflammation. Therefore, the compounds of the invention are anti-inflammatory agents which can be used in combating the inflammatory condition which occurs in various diseases, as well as immunosuppressives which can be used, for example, for preventing graft rejection in transplantation therapy. This activity can be demonstrated using the following test procedure.

Reaction mixtures (25 µl) containing human recombinant p56$^{lck}$, 10 mM MnCl$_2$, 10-µM ATP, 0.2 mM sodium vanadate, 20 µM peptide substrate (AlaGluGluGluIleTyr-GlyGlu-PheGluAlaLysLysLysLys, [γ-$^{33}$P] ATP (1000–2000 cpm/pmol) in 25 mM HEPES buffer (pH 7.5) and 0.1% Triton X-100 are incubated at 30° C. for 60 minutes and the reaction is then stopped by the addition of 10 µl of 2% orthophosphoric acid. Radiolabelled peptide is separated from unreacted [γ-$^{33}$P] ATP by filtration through Millipore Multiscreen phosphocellulose cation exchange paper filters. Bound peptide is washed with 0.5% orthophosphoric acid and incorporated radioactivity is determined by scintillation spectrometry.

The degree of enzyme blockade at each concentration of test compound is calculated from the following equation:

$$\frac{\text{CPM incorporated (+test compound + enzyme)}}{\text{CPM incorporated (−test compound + enzyme)}} \times 100$$

The IC$_{50}$ value is that concentration of test compound which reduces by 50% the protein kinase-induced incorporation of the radiolabel under the test conditions described earlier.

1-[3-(2-Aminoethyl)phenyl]-7-anilino-3-(2,6-dichlorophenyl)-3,4-dihydropyrimido[4,5-d]pyrimidin-2 (1H)-one has an IC$_{50}$ of 0.03 nM in the aforementioned test. Further examples are given in the following table:

| Compound of Example | IC$_{50}$(nM) |
|---|---|
| 1 | 10 |
| 7 | 0.6 |
| 10 | 19 |
| 22 | 265 |
| 50 | 6 |
| 63 | 17 |
| 82 | 0.4 |
| 85 | 7 |

The compounds of formula I, the pharmaceutically acceptable salts of basic compounds of formula I with acids and the pharmaceutically acceptable salts of acidic compounds of formula I with bases can be used as medicaments, e.g. in the form of pharmaceutical preparations especially for the treatment or prophylaxis of inflammatory, immunological, oncological, bronchopulmonary, dermatological and cardiovascular disorders, in the treatment of asthma, central nervous system disorders or diabetic complications or for the prevention of graft rejection following transplant surgery. The pharmaceutical preparations can be administered enterally, e.g. orally in the form of tablets, coated tablets, dragees, hard and soft gelatine capsules, solutions, emulsions or suspensions, nasally, e.g. in the form of nasal sprays, or rectally, e.g. in the form of suppositories. However, they may also be administered parenterally, e.g. in the form of injection solutions.

The compounds of formula I and their aforementioned pharmaceutically acceptable salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain therapeutically valuable substances other than the compounds of formula I and their aforementioned pharmaceutically acceptable salts.

Medicaments which contain a compound of formula I or a pharmaceutically acceptable salt thereof in association with a compatible pharmaceutical carrier material are also an object of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of formula I and their aforementioned pharmaceutically acceptable salts can be used in accordance with the invention as therapeutically active substances, especially as anti-inflammatory agents or for the prevention of graft rejection following transplant surgery. The dosage can vary within wide limits and will, of course, be fitted to the individual requirements in each particular case. In general, in the case of administration to adults a convenient daily dosage should be about 0.1 mg/kg to about 100 mg/kg, preferably about 0.5 mg/kg to about 5 mg/kg. The daily dosage may be administered as a single dose or in divided doses and, in addition, the upper dosage limit referred to earlier may be exceeded when this is found to be indicated.

Finally, the use of compounds of formula I and their aforementioned pharmaceutically acceptable salts for the manufacture of medicaments, especially in the treatment or prophylaxis of inflammatory, immunological, oncological, bronchopulmonary, dermato-logical and cardiovascular disorders, in the treatment of asthma, central nervous system disorders or diabetic complications or for the prevention of graft rejection following transplant surgery, is also an object of the invention.

The contents of GB Patent Application No. 9823277.0, filed Oct. 23, 1998, and No. 9920044.6, filed Aug. 24, 1999, are incorporated herein by reference.

The following Examples illustrate the present invention in more detail, but are not intended to limit its scope in any manner.

EXAMPLES

Example 1

A mixture of 2.55 g (6.6 mmol) of 3-(2,6-dichlorophenyl)-7-methanesulfonyl-3,4-dihydro-1-methylpyrimido[4,5-d]pyrimidin-2(1H)-one and 7 g (34 mmol) of 4-[2-(diethylamino)ethoxy]-aniline was heated at 180° C. for 35 minutes and then cooled. The residue was chromatographed on silica gel using firstly 5% methanol in dichloromethane and then dichloromethane/methanol/acetic acid/water (240:24:3:2) for the elution. Product-containing fractions were combined and evaporated. The residue was evaporated with toluene and then dissolved in 150 ml of dichloromethane. The solution was washed with 100 ml of saturated aqueous sodium bicarbonate solution, dried over magnesium sulfate and evaporated to give 1.18 g (35%) of crude product. Purification by crystallisation from cyclohexane/ethyl acetate gave 310 mg (9%) of pure 3-(2, 6-dichlorophenyl)-7-[4-[2-(diethylamino)ethoxy]anilino]-3, 4-dihydro-1-methylpyrimido[4,5-d]pyrimidin-2(1H)-one as a white solid of melting point 123–124° C.

The 3-(2,6-dichlorophenyl)-7-methanesulfonyl-3,4-dihydro-1-methylpyrimido[4,5-d]pyrimidin-2(1H)-one used as the starting material was prepared as follows:

a) A solution of 20 g (86 mmol) of ethyl 4-chloro-2-methylthiopyrimidine-5-carboxylate in 250 ml of dichloromethane was cooled to 0° C. and treated slowly with 35 ml (281 mmol) of a 33% solution of methylamine in ethanol. After stirring for 30 minutes 150 ml of water were added and the phases were separated. The organic phase was dried over magnesium sulfate and filtered. The filtrate was evaporated under reduced pressure to give 19 g (97%) of ethyl 4-methylamino-2-methylthiopyrimidine-5-carboxylate as a white solid.

b) 9 g (237 mmol) of lithium aluminium hydride were stirred in 300 ml of dry tetrahydrofuran and treated dropwise with a solution of 34 g (143 mmol) of ethyl 4-methylamino-2-methylthio-pyrimidine-5-carboxylate in 300 ml of dry tetrahydrofuran and left to stand for 15 minutes. The mixture was cooled in ice and cautiously treated dropwise with 18 ml of water. 36 ml of 2M sodium hydroxide solution were added dropwise, followed by 48 ml of water. The resulting suspension was stirred for 17 hours at room temperature and then filtered. The filter residue was washed twice with 100 ml of ethyl acetate each time and the combined filtrate and washings were evaporated under reduced pressure. The residue was suspended in 200 ml of dichloromethane/hexane (2:1) and the solid was filtered off and dried to give 23.5 g (86%) of 4-methylamino-2-methylthiopyrimidine-5-methanol as a yellow solid.

c) 20 g (108 mmol) of 4-methylamino-2-methylthiopyrimidine-5-methanol were stirred in 1 l of dichloromethane and treated with 87 g (1 mol) of manganese dioxide. The resulting suspension was stirred for 24 hours and then filtered through a filter aid. The filter residue was washed with 100 ml of dichloromethane and the combined filtrate and washings were evaporated under reduced pressure to give 15.8 g (80%) of 4-methylamino-2-methylthiopyrimidine-5-carboxaldehyde as a white solid.

d) A mixture of 6 g (32.8 mmol) of 4-methylamino-2-methylthiopyrimidine-5-carboxaldehyde, 5.5 g (33.9 mmol) of 2,6-dichloroaniline and 1 g (5.3 mmol) of 4-toluenesulfonic acid in 70 ml of toluene was heated under reflux with azeotropic removal of water for 17 hours. The mixture was concentrated to a volume of about 10 ml under reduced pressure and then treated with 120 ml of ethanol. The suspension obtained was heated to 75° C. and treated over a period of 15 minutes with 6.2 g (160 mmol) of sodium borohydride pellets. The mixture was stirred for a further 15 minutes and cooled to room temperature. The solvent was evaporated under reduced pressure and the residue was stirred in a mixture of 200 ml of 2M sodium hydroxide solution and 200 ml of ethyl acetate for 1 hour. The phases were separated and the organic phase was dried over magnesium sulfate and filtered. Evaporation of the filtrate under reduced pressure and flash chromatography of the residue using diethyl ether/hexane (3:7) for the elution gave 5.2 g (48%) of 5-(2,6-dichlorophenyl)aminomethyl-4-methylamino-2-methylthio-pyrimidine as a white solid.

e) A stirred solution, cooled in ice, of 12 ml of phosgene (20% solution in toluene; 23 mmol) in 100 ml of tetrahydrofuran was treated dropwise with a solution of 5 g (15.2 mmol) of 5-(2,6-dichlorophenyl)aminomethyl-4-methylamino-2-methylthiopyrimidine and 4 ml (29 mmol) of triethylamine in 80 ml of tetrahydrofuran. After stirring for 1 hour the mixture was treated with 100 ml of saturated aqueous ammonium chloride solution and the phases were separated. The aqueous phase was extracted with 100 ml of tetrahydrofuran and the combined organic solutions were dried over magnesium sulfate and filtered. The filtrate was concentrated under reduced pressure to give 4.8 g (89%) of 3-(2,6-dichlorophenyl)-7-methylthio-3,4-dihydro-1-methylpyrimido[4,5-d]pyrimidin-2(1H)-one as a white solid.

f) A solution of 5 g (14.1 mmol) of 3-(2,6-dichlorophenyl)-7-methylthio-3,4-dihydro-1-methylpyrimido[4,5-d] pyrimidin-2(1H)-one in 200 ml of dichloromethane was cooled in ice and treated with 10 g (28.9 mmol) of 3-chloroperbenzoic acid. The mixture was stirred at room temperature for 17 hours, then treated with 2 ml of dimethyl sulfoxide and left to stand for 10 minutes. 100 ml of saturated aqueous sodium bicarbonate solution were then added and the phases were separated. The organic phase was dried over magnesium sulfate and filtered. Concentration of the filtrate under reduced pressure gave 5 g (92%) of 3-(2,6-dichlorophenyl)-7-methanesulfonyl-3,4-dihydro-1-methylpyrimido[4,5-d]pyrimidin-2(1H)-one as a white solid.

The 4-[2-(diethylamino)ethoxy]-aniline used as the starting material was prepared as follows:

i) A solution of 27.8 g (0.2 mol) of 4-nitrophenol in 500 ml of ethanol was treated with 15 g (0.22 mol) of sodium ethoxide. After stirring at room temperature for 30 minutes the solvent was removed under reduced pressure. The residual yellow solid was stirred in a mixture of 160 ml of xylene and 30 ml of water and then treated with 41.4 g (0.3 mol) of potassium carbonate and 34.4 g (0.2 mol) of 2-diethylaminoethyl chloride hydrochloride. The mixture was heated under reflux for 17 hours and filtered while hot. The filter residue was washed with hot xylene and the combined filtrate and washings were evaporated under reduced pressure. Distillation of the residue under a high vacuum gave 31.4 g (66%) of 4-[2-(diethylamino)ethoxy]-nitrobenzene as a liquid.

ii) A solution of 5 g (21 mmol) of 4-[2-(diethylamino) ethoxy]-nitrobenzene in 50 ml of ethanol was hydrogenated over 100 mg of 10% palladium-on-carbon at room temperature and under atmospheric pressure. After 4 hours the suspension was filtered through a filter aid and the filtrate was evaporated under reduced pressure to give 4 g (92%) of 4-[2-(diethylamino)ethoxy]-aniline as an oil.

Example 2

A mixture of 100 mg (0.31 mmol) of 3-(2-chlorophenyl)-7-methanesulfonyl 3,4-dihydro-1-methylpyrimido[4,5-d] pyrimidin-2(1H)-one and 300 mg (1.4 mmol) of 4-[2-diethylamino)ethoxy]aniline was heated at 180° C. for 30 minutes and then cooled. The residue was chromatographed on silica gel using dichloromethane/methanol/acetic acid/ water (240:24:3:2) for the elution. Product-containing fractions were combined and evaporated. The residue was evaporated with toluene and then dissolved in 40 ml of dichloromethane. The solution was washed with 40 ml of saturated sodium bicarbonate solution, dried over magnesium sulfate, filtered and evaporated to give 20 mg (15%) of 3-(2-chlorophenyl)-7-[4-[2-(diethylamino)ethoxy]anilino]-3,4-dihydro-1-methylpyrimido[4,5-d]pyrimidin-2(1H)-one as a white solid of melting point 150–151° C.

The 3-(2-chlorophenyl)-7-methanesulfonyl-3,4-dihydro-1-methyl-pyrimidin-2(1H)-one used as the starting material was prepared in an analogous manner to that described in Example 1a)–f) using 2-chloroaniline in place of 2,6-dichloroaniline.

Example 3

A mixture of 100 mg (0.31 mmol) of 3-phenyl-7-methanesulfonyl-3,4-dihydro-1-methylpyrimido[4,5-d] pyrimidin-2(1H)-one and 300 mg (1.4 mmol) of 4-[2-(diethylamino)ethoxy]aniline was heated at 170–180° C. for 10 minutes and then cooled. The residue was chromatographed on silica gel using dichloromethane/methanol/ acetic acid/water (240:24:3:2) for the elution. Product-containing fractions were combined and evaporated. The residue was evaporated with toluene and then dissolved in 40 ml of dichloromethane. The solution was washed with 40 ml of saturated sodium bicarbonate solution, dried over magnesium sulfate, filtered and evaporated. The residual solid was purified by crystallisation from cyclohexane/ethyl acetate to give 14 mg (10%) of 3-phenyl-7-[4-[2-(diethylamino)ethoxy]anilino]-3,4-dihydro-1-methylpyrimido[4,5-d]pyrimidin-2(1H)-one as a white solid of melting point 141–144° C.

The 3-phenyl-7-methanesulfonyl-3,4-dihydro-1-methylpyrimido[4,5-d]-pyrimidin-2(1H)-one used as the starting material was prepared as follows:

a) 350 mg (1.6 mmol) of sodium triacetoxyborohydride and subsequently 0.1 ml (1.7 mmol) of acetic acid were added to a mixture of 200 mg (1.1 mmol) of 4-methylamino-2-methylthiopyrimidine-5-carboxaldehyde and 110 mg (1.2 mmol) of aniline in 5 ml of 1,2-dichloroethane. After 2.5 hours 25 ml of saturated aqueous sodium bicarbonate and 20 ml of dichloromethane were added. The phases were separated and the aqueous phase was washed twice with 25 ml of dichloromethane. The combined organic solutions were dried over magnesium sulfate, filtered and evaporated. The residue was chromatographed on silica gel using diethyl ether/hexane (1:1) for the elution. Product-containing fractions were combined and evaporated to give 218 mg (76%) of 5-phenylaminomethyl-4-methylamino-2-methylthiopyrimidine as a white solid.

b) A mixture of 200 mg (0.77 mmol) of 5-phenylaminomethyl-4-methylamino-2-methylthiopyrimidine and 0.2 ml (1.4 mmol) of triethylamine in 15 ml of dioxan was added dropwise to a solution, cooled in ice, of 150 mg (0.79 mmol) of trichloromethyl chloroformate in 10 ml of dioxan. The mixture was then left to warm to room temperature. After a further 10 minutes the mixture was evaporated. 40 ml of dichloromethane and 40 ml of saturated aqueous sodium bicarbonate solution were added to the residue. The phases were separated and the dichloromethane phase was dried over magnesium sulfate, filtered and evaporated to give 162 mg (74%) of 3-phenyl-7-methylthio-3,4-dihydro-1-methylpyrimido[4,5-d] pyrimidin-2(1H)-one as a white solid.

c) A solution of 160 mg (0.56 mmol) of 3-phenyl-7-methylthio-3,4-dihydro-1-methylpyrimido[4,5-d]pyrimidin-2(1H)-one in 20 ml of dichloromethane was treated with 400 mg (1.16 mmol) of 3-chloroperbenzoic acid (50% w/w in water). After 3 hours 30 ml of saturated aqueous sodium bicarbonate solution and 20 ml of dichloromethane were added and the phases were separated. The organic phase was dried over magnesium sulfate, filtered and then evaporated to give 165 mg (93%) of 3-phenyl-7-methanesulfonyl-3,4-dihydro-1-methylpyrimido[4,5-d]pyrimidin-2(1H)-one as a white solid.

Example 4

A mixture of 100 mg (0.31 mmol) of 3-cyclohexyl-7-methanesulfonyl-3,4-dihydro-1-methylpyrimido[4,5-d] pyrimidin-2-(1H)-one and 400 mg (1.9 mmol) of 4-[2-(diethylamino)ethoxy]aniline was heated at 180° C. for 35 minutes and then cooled. The residue was chromatographed on silica gel using dichloromethane/methanol/acetic acid/ water (240:24:3:2) for the elution. Product-containing fractions were combined and evaporated. The residue was evaporated with toluene and then dissolved in 40 ml of dichloromethane. The solution was washed with 40 ml of saturated aqueous sodium bicarbonate solution, dried over magnesium sulfate, filtered and evaporated. The residue was triturated in hexane, filtered off and dried to give 25 mg (18%) 3-cyclohexyl-7-[4-[2-(diethylamino)ethoxy]anilino]-3,4-dihydro-1-methylpyrimido[4,5-d]pyrimidin-2(1H)-one as a white solid of melting point 90–92° C.

The 3-cyclohexyl-7-methanesulfonyl-3,4-dihydro-1-methylpyrimido[4,5-d]pyrimidin-2(1H)-one used as the starting material was prepared as follows:

a) A mixture of 200 mg (1.1 mmol) of 4-methylamino-2-methylthiopyrimidine-5-carboxaldehyde and 200 mg (2.02 mmol) of cyclohexylamine in 10 ml of methanol was left to stand over 500 mg of type 4A molecular sieves for 3 days. The solution was decanted from the sieves and 100 mg (2.7 mmol) of sodium borohydride were added portionwise thereto. After 30 minutes the mixture was evaporated and 60 ml of ethyl acetate and 60 ml of 2M aqueous sodium hydroxide were added to the residue. The phases were separated and the organic phase was dried over magnesium sulfate, filtered and evaporated to give 245 mg (85%) of 5-cyclohexylaminomethyl-4-methylamino-2-methylthiopyrimidine as a colorless oil.

b) A mixture of 210 mg (0.79 mmol) of 5-cyclohexylaminomethyl-4-methylamino-2-methylthiopyrimidine and 0.2 ml of triethylamine in 10 ml of tetrahydrofuran was added dropwise to an ice-cooled solution of 0.5 ml (0.96 mmol) of phosgene (20% solution in toluene) in 5 ml of tetrahydrofuran. After 1 hour 15 ml of aqueous ammonium chloride solution and 10 ml of tetrahydrofuran were added to the resulting mixture. The phases were separated. The organic phase was dried over magnesium sulfate, filtered and then evaporated. The residue was chromatographed on silica gel using diethyl ether/hexane (3:2) for the elution. Product-containing fractions were combined and evaporated to give 120 mg (52%) of 3-cyclohexyl-7-methylthio-3,4-dihydro-1-methylpyrimido[4,5-d]pyrimidin-2(1H)-one as white solid.

c) A solution of 100 mg (0.34 mmol) 3-cyclohexyl-7-methylthio-3,4-dihydro-1-methylpyrimido[4,5-d]pyrimidin-2(1H)-one in 10 ml of dichloromethane was treated with 250 ml (0.74 mmol) of 3-chloroperbenzoic acid (50% w/w water). After 3 hours 30 ml of saturated aqueous sodium bicarbonate solution and 20 ml of dichloromethane were added and the phases were separated. The organic phase was dried over magnesium sulfate, filtered and then evaporated to give 165 mg (93%) of 3-cyclohexyl-7-methanesulfonyl-3,4-dihydro-1-methylpyrimido[4,5-d]pyrimidin-2(1H)-one as a white solid.

Example 5

A mixture of 250 ml (0.83 mmol) of 3-tert.butyl-7-methanesulfonyl-3,4-dihydro-1-methylpyrimido[4,5-d]pyrimidin-2(1H)-one and 600 mg (2.9 mmol) of 4-(2-(diethylamino)ethoxy)aniline was heated at 180° C. for 35 minutes and then cooled. The residue was chromatographed on silica gel using dichloromethane/methanol/acetic acid/water (240:24:3:2) for the elution. Product-containing fractions were combined and evaporated. The residue was evaporated with toluene and then dissolved in 30 ml of dichloromethane. The solution was washed with 20 ml of saturated aqueous sodium bicarbonate solution, dried over magnesium sulfate, filtered and evaporated. The residue was triturated in hexane, filtered off and dried to give 70 mg (21%) of 3-tert.butyl-7-[4-[2-(diethylamino)ethoxy]anilino]-3,4-dihydro-1-methylpyrimido[4,5-d]pyrimido-2(1H)-one as an off-white solid of melting point 130° C.

The 3-tert.butyl-7-methanesulfonyl-3,4-dihydro-1-methylpyrimido[4,5-d]-pyrimidin-2(1H)-one used as the starting material was prepared as follows:

a) A mixture of 200 mg (1.1 mmol) of 4-methylamino-2-methylthiopyrimidine-5-carboxaldehyde and 0.23 ml (2.18 mmol) of tert.butylamine in 10 ml of methanol was left to stand over 500 mg of type 4A molecular sieves for 3 days. The solution was decanted from the sieves and 100 mg (2.7 mmol) of sodium borohydride were added portionwise thereto. After minutes the mixture was evaporated and 20 ml of ethyl acetate and 20 ml of 2M aqueous sodium hydroxide were added to the residue. The phases were separated and the organic phase was dried over magnesium sulfate, filtered and evaporated to give 240 mg (92%) of 5-tert.butylaminomethyl-4-methylamino-2-methylthiopyrimidine as a white solid.

b) A mixture of 240 mg (1 mmol) of 5-tert.butylaminomethyl-4-methylamino-2-methylthiopyrimidine and 0.28 ml of triethylamine in 5 ml of tetrahydrofuran was added dropwise to an ice-cooled solution of 1 ml (1.92 mmol) of phosgene (20% solution in toluene) in 5 ml of tetrahydrofuran. After 1 hour 30 ml of saturated aqueous ammonium chloride and 20 ml of tetrahydrofuran were added to the resulting mixture. The phases were separated. The organic phase was dried over magnesium sulfate, filtered and then evaporated to give 220 mg (83%) of 3-tert.butyl-7-methylthio-3,4-dihydro-1-methylpyrimido[4,5-d]pyrimidin-2(1H)-one as a white solid.

c) A solution of 220 mg (0.83 mmol) of 3-tert.butyl-7-methylthio-3,4-dihydro-1-methylpyrimido[4,5-d]pyrimidin-2(1H)-one in 20 ml of dichloromethane was treated with 570 mg (1.66 mmol) of 3-chloroperbenzoic acid (50% w/w in water). After 18 hours 0.2 ml of saturated aqueous sodium bicarbonate solution was added and the phases were separated. The organic phase was washed with 20 ml of saturated aqueous sodium bicarbonate solution, dried over magnesium sulfate, filtered and then evaporated to give 250 mg (100%) of 3-tert.butyl-7-methanesulfonyl-3,4-dihydro-1-methylpyrimido[4,5-d]pyrimidin-2(1H)-one as a white solid.

Example 6

A mixture of 200 mg (0.65 mmol) of 3-cyclopentyl-7-methanesulfonyl-3,4-dihydro-1-methylpyrimido[4,5-d]pydrimidin-2(1H)-one and 300 mg (1.4 mmol) of 4-[2-(diethylamino)ethoxy]aniline was heated at 180° C. for 35 minutes and then cooled. The residue was chromatographed on silica gel using dichloromethane/methanol/acetic acid/water (240:24:3:2) for the elution. Product-containing fractions were combined and evaporated. The residue was evaporated with toluene and then dissolved in 30 ml of dichloromethane. The solution was washed with 20 ml of saturated aqueous sodium bicarbonate solution, dried over magnesium sulfate, filtered and evaporated. The residue was purified by reverse-phase high performance liquid chromatography (HPLC). The mobile phase was water/0.1% trifluoroacetic acid (A) and acetonitrile/0.07% trifluoroacetic acid (B); the gradient was 5%–95% B over 20 minutes; and the product was detected using an ultraviolet detector at a wavelength of 215 nm. Product-containing fractions were lyophilized to give 20 mg (7%) of 3-cyclopentyl-7-[4-[2-(diethylamino)ethoxy]anilino]-3,4-dihydro-1-methylpyrimido[4,5d]pydrimidin-2(1H)-one trifluoroacetate as a white solid of melting point 89° C.

The 3-cyclopentyl-7-methanesulfonyl-3,4-dihydro-1-methylpyrimido[4,5-d]-pyrimidin-2(1H)-one used as the starting material was prepared in an analogous manner to that described in Example 5a)–c) using cyclopentylamine in place of tert.butylamine.

Example 7

A mixture of 120 mg (0.27 mmol) of 3-(2,6-dichlorophenyl)-7-methane-sulfonyl-3,4-dihydro-1- phenylpyrimido[4,5-d]pyrimidin-2(1H)-one and 370 mg (1.8 mmol) of 4-[2-(diethylamino)ethoxy]aniline was heated at 180° C. for 40 minutes and then cooled. The residue was chromatographed on silica gel using dichloromethane/methanol/acetic acid/water (240:24:3:2) for the elution. Product-containing fractions were combined and evaporated. The residue was evaporated with toluene and then dissolved in 50 ml of dichloromethane. The solution was washed with 50 ml of saturated aqueous sodium bicarbonate solution, dried over magnesium sulfate, filtered and evaporated. The residual solid was purified by crystallisation from cyclohexane/ethyl acetate to give 10 mg (6%) of 3-(2,6-dichlorophenyl)-7-[4-[2-(diethylamino) ethoxy]anilino]-3,4-dihydro-1-phenylpyrimido[4,5-d]pyrimidin-2(1H)-one as an off-white solid of melting point 162–163° C.

The 3-(2,6-dichlorophenyl)-7-methanesulfonyl-3,4-dihydro-1-phenylpyrimido[4,5-d]pyrimidin-2(1H)-one used as the starting material was prepared as follows:

a) A mixture of 4 g (17.2 mmol) of ethyl 4-chloro-2-methylthiopyrimidine-5-carboxylate and 5 g (54 mmol) of aniline in 40 ml of dioxan was stirred at room temperature for 24 hours. The mixture was then evaporated and 100 ml of ethyl acetate and 50 ml of 2M aqueous hydrochloric acid were added to the residue. The phases were separated and the organic phase was washed with 50 ml of aqueous hydrochloric acid, dried over magnesium sulfate, filtered and evaporated. The resulting solid was purified by crystallisation from aqueous ethanol to give 3.5 g (64%) of ethyl 4-phenylamino-2-methylthiopyrimidine-5-carboxylate as a white solid.

b) A solution of 3.5 g (11.1 mmol) of ethyl 4-phenylamino-2-methylthiopyrimidine-5-carboxylate in 50 ml of tetrahydrofuran was cooled in ice and then treated dropwise with 12 ml (12 mmol) of 1M lithium aluminium hydride in tetrahydrofuran. The cooling was removed and the mixture was stirred at room temperature for 3 hours. The mixture was then cooled in ice and cautiously treated dropwise with 0.5 ml of water, 0.75 ml of 2M aqueous sodium hydroxide and then 1 ml of water. The resulting suspension was filtered through a filter aid. The filtrate was evaporated to give 2.7 g (98%) of 4-phenylamino-2-methylthiopyrimidine-5-methanol as a yellow oil.

c) 2.7 g (10.9 mmol) of 4-phenylamino-2-methylthiopyrimidine-5-methanol were stirred in 50 ml of dichloromethane and treated with 9.6 g (111 mmol) of manganese dioxide. The suspension was stirred for 18 hours and then filtered through a filter aid. The filtrate was evaporated and the residue was chromatographed on silica gel using diethyl ether/hexane (1:1) for the elution. Product-containing fractions were combined and evaporated to give 1.8 g (67%) of 4-phenylamino-2-methylthiopyrimidine-5-carboxaldehyde as a white solid.

d) A mixture of 700 mg (2.9 mmol) of 4-phenylamino-2-methylthiopyrimidine-5-carboxaldehyde, 490 mg (3.0 mmol) of 2,6-dichloroaniline and 100 mg (0.5 mmol) of 4-toluenesulfonic acid in 50 ml of toluene was heated at reflux with the azeotropic removal of water for 18 hours. The mixture was cooled and evaporated. 50 ml of methanol and 400 mg (11.7 mmol) of sodium borohydride were added and the mixture was heated at reflux for 20 minutes, cooled and then evaporated. The residue was stirred in a mixture of 50 ml of 2M aqueous sodium hydroxide and 50 ml of ethyl acetate for 30 minutes and then the phases were separated. The organic phase was dried over magnesium sulfate, filtered and evaporated. Flash chromatography of the residue on silica gel using diethyl ether/hexane (2:3) for the elution gave 410 mg (36%) of 5-(2,6-dichlorophenyl)aminomethyl-4-phenylamino-2-methylthiopyrimidine as a white solid.

e) A stirred solution, cooled in ice, of 0.25 ml (0.48 ml) of phosgene (20% in toluene) in 5 ml of tetrahydrofuran was treated dropwise with a solution of 100 mg (0.26 mmol) of 5-(2,6-dichlorophenyl)aminomethyl-4-phenylamino-2-methylthiopyrimidine and 0.1 ml (0.7 mmol) of triethylamine in 10 ml of tetrahydrofuran. The mixture was stirred at room temperature for 3 days. 20 ml of tetrahydrofuran and 20 ml of saturated aqueous ammonium chloride solution were added, the phases were separated and the organic phase was dried over magnesium sulfate, filtered and evaporated to give 110 mg (100%) of 3-(2,6-dichlorophenyl)-7-methylthio-3,4-dihydro-1-phenylpyrimido[4,5-d]pyrimidin-2(1H)-one as a white solid.

f) A solution of 110 mg (0.26 mmol) of 3-(2,6-dichlorophenyl)-7-methylthio-3,4-dihydro-1-phenylpyrimido[4,5-d]pyrimidin-2(1H)-one in 5 ml of dichloromethane was treated with 190 mg (0.55 mmol) of 3-chloroperbenzoic acid (50% w/w in water). After 18 hours 40 ml of saturated aqueous sodium bicarbonate solution and 40 ml of dichloro-methane were added and the phases were separated. The organic phase was dried over magnesium sulfate, filtered and evaporated to give 120 mg (100%) of 3-(2,6-dichlorophenyl)-7-methanesulfonyl-3,4-dihydro-1-phenylpyrimido[4,5-d]pyrimidin-2(1H)-one as a pale yellow oil.

Example 8

A mixture of 100 mg (0.25 mmol) of 3-(2,6-dichlorophenyl)-1-ethyl-7-methanesulfonyl-3,4-dihydropyrimido[4,5-d]pyrimidin-2(1H)-one and 120 mg (0.5 mmol) of 4-[2-(diethylamino)ethoxy]aniline was heated at 180° C. for 35 minutes and then cooled. The residue was chromatographed on silica gel using dichloromethane/methanol/acetic acid/water (240:24:3:2) for the elution. Product-containing fractions were combined and evaporated. The residue was evaporated with toluene and then dissolved in 50 ml of dichloromethane. The solution was washed with 50 ml of saturated aqueous sodium bicarbonate solution, dried over magnesium sulfate, filtered and evaporated to give 30 mg (22%) of 3-(2,6-dichlorophenyl)-1-ethyl-7-[4-[2-(diethylamino)ethoxy]anilino]-3,4-dihydropyrimido[4,5-d]pyrimidin-2(1H)-one as an orange colored solid of melting point 85° C.

The 3-(2,6-dichlorophenyl)-1-ethyl-7-methanesulfonyl-3,4-dihydro-pyrimido[4,5-d]-pyrimidin-2(1H)-one used as the starting material was prepared as follows:

a) A mixture of 49 g (246 mmol) of 4-amino-5-carbethoxypyrimidine-2-thiol and 42 g (304 mmol) of potassium carbonate in 400 ml of acetone was treated with 50 g (352 mmol) of iodomethane. After stirring for 3 hours 500 ml of water were added. The phases were separated and the aqueous phase was extracted twice with 300 ml of dichloromethane each time. The combined organic phases were washed with 100 ml of brine, dried over magnesium sulfate, filtered and evaporated to give 45.2 g (86%) of ethyl 4-amino-2-methylthiopyrimidine-5-carboxylate as a pale yellow solid.

b) 13 g (338 mmol) of lithium aluminium hydride were stirred in 300 ml of tetrahydrofuran and treated dropwise with a solution of 45 g (211 mmol) of ethyl 4-amino-2-methylthiopyrimidine-5-carboxylate in 300 ml of tetrahydrofuran. 15 minutes after completion of the addition the mixture was cooled in ice and cautiously treated dropwise with 25 ml of water. After stirring for 2 hours at room temperature the mixture was filtered through a filter aid and the filtrate was evaporated. The residue was triturated in 500 ml of dichloromethane/hexane (1:1), collected by filtration and dried to give 28 g (78%) of 4-amino-2-methylthiopyrimidine-5-methanol as a white solid.

c) 28 g (164 mmol) of 4-amino-2-methylthiopyrimidine-5-methanol were stirred in 500 ml of dichloromethane and treated with 150 g (1.7 mol) of manganese dioxide. The suspension was stirred for 24 hours and then filtered through a filter aid. The filtrate was evaporated to give 20.2 g (73%) of 4-amino-2-methylthiopyrimidine 5-carboxaldehyde as a pale yellow solid.

d) A mixture of 10 g (59.2 mmol) of 4-amino-2-methylthiopyrimidine-5-carboxaldehyde, 9.7 g (59.9 mmol) of 2,6-dichloroaniline and 1 g (5.3 mmol) of 4-toluenesulfonic acid in 200 ml of xylene was heated at reflux with the azeotropic removal of water for 24 hours. The mixture was cooled and evaporated. 50 ml of acetic acid and 20 ml of toluene were added to the residue. The mixture was cooled in ice and treated portionwise over 30 minutes with 5 g (147 mmol) of sodium borohydride. After 1 hour the mixture was evaporated and the residue was stirred in a mixture of 100 ml of ethyl acetate and 100 ml of 2M aqueous sodium hydroxide for 1 hour. The phases were separated and the organic phase was dried over magnesium sulfate, filtered and evaporated. Crystallisation of the residue from aqueous ethanol gave 2.4 g (13%) of 5-(2,6-dichlorophenyl) aminomethyl-4-amino-2-methylthiopyrimidine as a white solid. The mother liquors were evaporated and flash chromatography of the residue on silica gel using diethyl ether/hexane (1:1) for the elution gave a further 2.1 g (11%) of 5-(2,6-dichlorophenyl)aminomethyl-4-amino-2-methylthiopyrimidine as a white solid.

e) A stirred solution, cooled in ice, of 5.8 ml (11.2 mmol) of phosgene (20% in toluene) in 80 ml of tetrahydrofuran was treated dropwise with a solution of 1.76 g (5.6 mmol) of 5-(2,6-dichlorophenyl)aminomethyl-4-amino-2-methylthiopyrimidine and 1.6 ml (11.2 mmol) of triethylamine in 80 ml of tetrahydrofuran. The mixture was stirred for 1 hour. 50 ml of tetrahydrofuran and 50 ml of saturated aqueous ammonium chloride solution were added. The phases were separated and the organic phase was washed with saturated aqueous ammonium chloride solution, dried over magnesium sulfate, filtered and evaporated to give 1.7 g (89%) of 3-(2,6-dichlorophenyl)-7-methylthio-3,4-dihydropyrimido[4,5-d]pyrimidin-2(1H)-one as a white solid.

f) A solution of 220 mg (0.64 mmol) of 3-(2,6-dichlorophenyl)-7-methylthio-3,4-dihydropyrimido[4,5-d]pyrimidine-2(1H)-one in 10 ml of dichloromethane was treated with 440 mg (1.28 mmol) of 3-chloroperbenzoic acid (50% w/w in water) and stirred for 18 hours. 0.2 ml of dimethyl sulfoxide was added. After a further 15 minutes 15 ml of saturated aqueous sodium bicarbonate solution were added. The phases were separated and then the organic phase was washed with 30 ml of saturated aqueous sodium bicarbonate solution, dried over magnesium sulfate and evaporated to give 250 mg (100%) of 3-(2,6-dichlorophenyl)-7-methanesulfonyl-3,4-dihydropyrimido[4,5-d]pyrimidin-2(1H)-one as a white solid.

g) A solution, cooled in ice, of 100 mg (0.27 ml) of 3-(2,6-dichlorophenyl)-7-methanesulfonyl-3,4-dihydropyrimido[4,5-d]pyrimidin-2(1H)-one in 6 ml of dimethylformamide was treated with 11 mg (0.27 mmol) of sodium hydride (60% w/w). After 30 minutes the mixture was treated with 0.03 ml (0.3 mmol) of iodoethane and then heated to 90° C. for 2 hours. The mixture was evaporated and the residue was treated with 30 ml of dichloromethane and 30 ml of water. The phases were separated and the organic phase was washed with 30 ml of water, dried over magnesium sulfate, filtered and evaporated to give 100 mg (92%) of 3-(2,6-dichlorophenyl)-1-ethyl-7-methanesulfonyl-3,4-dihydropyrimido[4,5-d]pyrimidin-2 (1H)-one as a yellow solid.

Example 9

A mixture of 100 mg (0.22 mmol) of 1-benzyl-3-(2,6-dichlorophenyl)-7-methanesulfonyl-3,4-dihydropyrimido[4,5-dl]pyrimidin-2(1H)-one and 120 mg (0.5 mmol) of 4-[2-(diethylamino)ethoxy]aniline was heated at 180° C. for 35 minutes and then cooled. The residue was chromatographed on silica gel using dichloromethane/methanol/acetic acid/water (240:24:3:2) for the elution. Product-containing fractions were combined and evaporated. The residue was evaporated with toluene and then dissolved in 50 ml of dichloromethane. The solution was washed with 50 ml of saturated aqueous sodium bicarbonate solution, dried over magnesium sulfate, filtered and evaporated to give 30 mg (23%) of 1-benzyl-3-(2,6-dichlorophenyl)-7-[4-[2-(diethylamino)ethoxy]anilino]-3,4-dihydropyrimido[4,5-d] pyrimidin-2(1H)-one as a white solid of melting point 106° C.

The 1-benzyl-3-(2,6-dichlorophenyl)-7-methanesulfonyl-3,4-dihydropyrimido[4,5-d]pyrimidin-2(1H)-one used as the starting material was prepared as follows:

A solution, cooled in ice, of 100 mg (0.27 mmol) of 3-(2,6-dichlorophenyl)-7-methanesulfonyl-3,4-dihydropyrimido[4,5-d]pyrimidin-2(1H)-one in 6 ml of dimethylformamide was treated with 11 mg (0.27 ml) of sodium hydride (60% w/w). After 30 minutes the mixture was treated with 0.04 ml (0.3 mmol) of benzyl bromide and then heated to 90° C. for 2 hours. The mixture was evaporated and 30 ml of dichloromethane and 30 ml of water were added to the residue. The phases were separated and the organic phase was washed with 30 ml of water, dried over magnesium sulfate, filtered and evaporated to give 100 mg (80%) of 1-benzyl-3-(2,6-dichlorophenyl)-7-methanesulfonyl-3,4-dihydropyrimido[4,5-d]pyrimidin-2 (1H)-one as a yellow solid.

Example 10

A mixture of 60 mg (0.13 mmol) of 3-(2,6-dichlorophenyl)-7-methanesulfonyl-3,4-dihydro-1-[(3-pyridyl)methyl]pyrimido[4,5-d]pyrimidin-2(1H)-one and 150 mg (0.72 mmol) of 4-[2-(diethylamino)ethoxy]aniline was heated at 180° C. for 35 minutes and then cooled. The residue was chromatographed on silica gel using dichloromethane/methanol/acetic acid/water (240:24:3:2) for the elution. Product-containing fractions were combined and evaporated. The residue was evaporated with toluene and then dissolved in 50 ml of dichloromethane, washed with 50 ml of saturated aqueous sodium bicarbonate solution, dried over magnesium sulfate, filtered and evaporated. The residue was purified by reverse-phase HPLC. The mobile phase was water/0.1% trifluoroacetic acid (A) and acetonitrile/0.07% trifluoroacetic acid (B). The gradient was 5%–95% B over 20 minutes, with the product being detected using an ultraviolet detector at a wavelength of 215 nm. Product-containing fractions were lyophilized to give 16 mg (17%) of 3-(2,6-dichlorophenyl)-7-[4-[2-(diethylamino) ethoxy]anilino]-3,4-dihydro-1-[(3-pyridyl)-methyl] pyrimido[4,5-d]pyrimidin-2(1H)-one trifluoroacetate as a white solid of melting point 64° C.

The 3-(2,6-dichlorophenyl)-7-methanesulfonyl-3,4-dihydro-1-[(3-pyridyl)-methyl]pyrimido[4,5-d]pyrimidin-2 (1H)-one used as the starting material was prepared as follows:

An ice-cooled solution of 100 mg (0.27 mmol) of 3-(2,6-dichlorophenyl)-7-methanesulfonyl-3,4-dihydropyrimido[4,5-d]pyrimidin-2(1H)-one in 6 ml of dimethylformamide was treated with 22 mg (0.54 mmol) of sodium hydride (60% w/w). After 30 minutes the mixture was treated with 50 mg (0.3 mmol) of picolyl chloride hydrochloride and then heated to 90° C. for 2 hours and to 100° C. for a further hour. The mixture was evaporated and the residue was treated with 30 ml of dichloromethane and 30 ml of water. The phases were separated and the organic phase was washed with 30 ml of water, dried over magnesium sulfate, filtered and evaporated to give 60 mg (48%) of 3-(2,6-dichlorophenyl)-7-methanesulfonyl-3,4-dihydro-1-[(3-pyridyl)methyl]pyrimido[4,5-d]pyrimidin-2(1H)-one as a yellow solid.

Example 11

A mixture of 110 mg (0.29 mmol) of 3-(2,6-dichlorophenyl)-7-methanesulfonyl-3,4-dihydro-1-methylpyrimido[4,5-d]pyrimidin-2(1H)-one and 0.31 ml (2.9 mmol) of benzylamine was heated at 180° C. for 10 minutes and then cooled. 30 ml of ethyl acetate and 30 ml of 2M aqueous hydrochloric acid were added to the residue. The phases were separated and the organic phase was washed in sequence with 20 ml of 5% aqueous sodium bicarbonate solution and 20 ml of brine, dried over magnesium sulfate, filtered and evaporated to give 93 mg (79%) of 7-benzylamino-3-(2,6-dichlorophenyl)-3,4-dihydro-1-methylpyrimido[4,5-d]pyrimidin-2(1H)-one as a white solid of melting point 195–198° C.

Example 12

A mixture of 100 mg (0.26 mmol) of 3-(2,6-dichlorophenyl)-7-methane-sulfonyl-3,4-dihydro-1-methylpyrimido[4,5-d]pyrimidin-2(1H)-one and 0.25 ml (2.6 mmol) of 4-fluoroaniline was heated at 180° C. for 30 minutes and then cooled. 30 ml of ethyl acetate and 30 ml of 2M hydrochloric acid were added to the residue. The phases were separated and the organic phase was washed with 20 ml of brine, dried over magnesium sulfate, filtered and evaporated. The residue was chromatographed on silica gel using ethyl acetate/hexane (2:3) for the elution. Product-containing fractions were combined and evaporated to give 40 mg (37%) of 3-(2,6-dichlorophenyl)-7-(4-fluoroanilino)-3,4-dihydro-1-methylpyrimido[4,5-d]-pyrimidin-2(1H)-one as a light grey solid of melting point 208–211° C.

Example 13

A mixture of 100 mg (0.26 mmol) of 3-(2,6-dichlorophenyl)-7-methane-sulfonyl-3,4-dihydro-1-methylpyrimido[4,5-d]pyrimido-2(1H)-one and 0.24 ml (2.6 mmol) of aniline was heated at 180° C. for 30 minutes and then cooled. 30 ml of ethyl acetate and 30 ml of 2M aqueous hydrochloric acid were added to the residue. The phases were separated and the organic phase was washed with 20 ml of brine, dried over magnesium sulfate, filtered and evaporated. The residue was chromatographed on silica gel using ethyl acetate/hexane (1:1) for the elution. Product-containing fractions were combined and evaporated to give 42 mg (40%) of 7-anilino-3-(2,6-dichlorophenyl)-3,4-dihydro-1-methylpyrimido[4,5-d]pyrimidin-2(1H)-one as a pale purple solid of melting point 222–224° C.

Example 14

A mixture of 100 mg (0.26 mmol) of 3-(2,6-dichlorophenyl)-7-methane-sulfonyl-3,4-dihydro-1-methylpyrimido[4,5-d]pyrimidin-2(1H)-one and 0.32 ml (2.6 mmol) of 4-methoxyaniline was heated at 60° C. for 4 hours and then cooled. 10 ml of 2M aqueous hydrochloric acid were added to the residue. The precipitated yellow solid was filtered off, washed in sequence with 2M aqueous hydrochloric acid, water and diethyl ether and then dried to give 45 mg (40%) of 3-(2,6-dichlorophenyl)-3,4-dihydro-7-(4-methoxyanilino)-1-methylpyrimido[4,5-d]pyrimidin-2(1H)-one as a yellow solid of melting point 175° C. (decomposition).

Example 15

A mixture of 200 mg (0.52 mmol) of 3-(2,6-dichlorophenyl)-7-methanesulfonyl-3,4-dihydro-1-methylpyrimido[4,5-d]pyrimidin-2(1H)-one and 140 mg (0.8 mmol) of 4-[2-(dimethylamino)ethoxy]aniline was heated at 160° C. for 2 hours and then cooled. The residue was chromatographed on silica gel using firstly dichloromethane/methanol/acetic acid/water (240:24:3:2) and then dichloromethane/methanol/acetic acid/water (90:18:3:2) for the elution. Product-containing fractions were combined and evaporated. The residue was evaporated with toluene and then dissolved in 40 ml of dichloromethane, washed with 40 ml of saturated aqueous sodium bicarbonate solution, dried over magnesium sulfate, filtered and evaporated to give 35 mg (23%) of 3-(2,6-dichlorophenyl)-7-[4-[2-(dimethylamino)ethoxy]anilino]-3,4-dihydro-1-methylpyrimido[4,5-d]pyrimidin-2(1H)-one as a white solid of melting point 173–174° C.

The 4-[2-(dimethylamino)ethoxy]aniline used as the starting material was prepared as follows:

a) A suspension of 5 g (36 mmol) of 4-nitrophenol in 250 ml of xylene was treated with a solution of 1.63 g (41 mmol) of sodium hydroxide in 20 ml of water and the mixture was stirred at room temperature for 30 minutes. The mixture was then treated with 7.5 g (54 mmol) of potassium carbonate and 5.11 g (36 mmol) of dimethylaminoethyl chloride hydrochloride. The mixture was heated at reflux for 2 hours and then for a further 24 hours with azeotropic removal of water. The mixture was filtered while hot and the solid was washed with hot xylene. The combined filtrate and washings were evaporated and the residue was distilled under a high vacuum to give 1.28 g (20%) of 4-[2-dimethylamino)ethoxy]nitrobenzene as an orange colored liquid.

b) A solution of 880 mg (3.7 mmol) of 4-[2-dimethylamino)ethoxy]nitrobenzene in 10 ml of ethanol was hydrogenated at atmospheric pressure over 88 mg of 10% palladium on charcoal for 3 hours. The suspension was filtered through a pad of filter aid and the filtrate was evaporated to give 680 mg (100%) of 4-[2-(dimethylamino)ethoxy]aniline as an orange colored liquid.

Example 16 a) A mixture of 200 mg (0.52 mmol) of 3-(2,6-dichlorophenyl)-3,4-dihydro-7-methanesulfonyl-1-methylpyrimido[4,5-d]pyrimidin-2(1H)-one and 800 mg (4.47 mmol) of ethyl 4-aminophenylacetate was heated at 185° C. for 45 minutes. The residue was partitioned between 10 ml of ethyl acetate and 10 ml of 2M hydrochloric acid and the insoluble cream colored solid was collected by filtration and washed with 20 ml of water and 20 ml of ethyl acetate and then dried under a high vacuum. 95 mg (38%) of ethyl 2-[4-[[3-(2,6-dichlorophenyl)-1,2,3,4-tetrahydro-1-methyl-2-oxopyrimido[4,5-d]pyrimidin-7-yl]amino]phenyl]acetate of melting point 211–212° C. were isolated.

b) A 1.0M solution of lithium aluminium hydride in anhydrous tetrahydrofuran (91 μl; 91 μmol) was added dropwise to a stirred solution of 40 mg (82 μmol) of ethyl 2-[4-[[3-(2,6-dichlorophenyl)-1,2,3,4-tetrahydro-1-methyl-2-oxopyrimido[4,5-d]pyrimidin-7-yl]amino]-phenyl]acetate in 4 ml of anhydrous tetrahydrofuran at 0° C. and the mixture was stirred for a further 90 minutes. The reaction was quenched with 10 ml of 2M sodium hydroxide and the mixture was extracted twice with 10 ml of ethyl acetate each time. The combined organic extracts were dried over magnesium sulfate, filtered and evaporated. The residue was purified by flash column chromatography on silica gel using ethyl acetate/hexane (2:1) for the elution. Product-containing fractions were evaporated to give 25 mg (68%) of 3-(2,6-dichlorophenyl)-3,4-dihydro-7-[4-(2-hydroxyethyl)anilino]-1-methylpyrimido[4,5-d]pyrimidin-2(1H)-one as a white solid of melting point 148–151° C.

The ethyl 4-aminophenylacetate used as the starting material was prepared as follows:

A solution of 1 g (4.78 mmol) of ethyl-4-nitrophenylacetate in 10 ml of dry methanol was treated with 100 mg of 10% palladium-on-carbon and then hydrogenated at room temperature and at atmospheric pressure for 4 hours. The catalyst was removed by filtration and the filtrate was evaporated to give 830 mg (97%) of ethyl 4-aminophenylacetate as a mobile yellow oil.

Example 17

A mixture of 100 mg (0.26 mmol) of 3-(2,6-dichlorophenyl)-3,4-dihydro-7-methanesulfonyl-1-methylpyrimido[4,5-d]pyrimidin-2(1H)-one and 400 μl (3.4 mmol) of phenethylamine was heated at 180° C. for 4 hours and then cooled to room temperature. The mixture was dissolved in 10 ml of ethyl acetate and washed in sequence with 10 ml of 2M hydrochloric acid and 10 ml of saturated aqueous sodium bicarbonate solution. The ethyl acetate phase was separated, dried over magnesium sulfate, filtered and evaporated. The crude product was purified by flash column chromatography on silica gel using 5% methanol/dichloromethane for the elution. Product-containing fractions were combined and evaporated to give 35 mg of 3-(2,6-dichlorophenyl)-3,4-dihydro-1-methyl-7-(2-phenylethylamino)pyrimido[4,5-d]pyrimidin-2(1H)-one as a pale yellow solid of melting point 148–151° C.

Example 18

A mixture of 2.2 g (5.7 mmol) of 3-(2,6-dichlorophenyl)-3,4-dihydro-7-methanesulfonyl-1-methylpyrimido[4,5-d]pyrimidin-2(1H)-one and 4.8 g (28.5 mmol) of 2,4-dimethoxybenzylamine was heated at 55° C. for 2 hours and then left to cool. The mixture was dissolved in 100 ml of dichloromethane and washed in sequence with 30 ml of 2M hydrochloric acid, 30 ml of saturated aqueous sodium bicarbonate solution and 30 ml of brine. The organic phase was separated, dried over magnesium sulfate, filtered and evaporated. The residue was triturated with ethyl acetate/hexane (1:1) and 3-(2,6-dichlorophenyl)-3,4-dihydro-7-(2,4-dimethoxybenzylamino)-1-methylpyrimido[4,5-d]pyrimidin-2(1H)-one was collected by filtration as a white solid which was dried at 40° C. under a high vacuum. The yield was 2.35 g (87%) after drying and the melting point was 152–154° C.

Example 19

A solution of 200 mg (0.42 mmol) of 3-(2,6-dichlorophenyl)-3,4-dihydro-7-(2,4-dimethoxybenzylamino)-1-methylpyrimido[4,5-d]pyrimidin-2(1H)-one in 2 ml of dichloromethane was treated with 2 ml of trifluoroacetic acid and the mixture was stirred at room temperature under a nitrogen atmosphere for 5 hours. The solvent was evaporated, the residue was triturated with saturated aqueous sodium bicarbonate solution and the product was collected by filtration and sucked dry. The dried product was purified further by suspension in dichloromethane and filtration through a polytetrafluoroethylene membrane. The filtrate was evaporated and the residue was dried to give 115 mg (84%) of 7-amino-3-(2,6-dichlorophenyl)-3,4-dihydro-1-methylpyrimido[4,5-d]pyrimidin-2(1H)-one as a white solid of melting point 176–184° C.

Example 20

A solution of 100 mg (0.22 mmol) of 3-(2,6-dichlorophenyl)-7-methanesulfonyl-1-phenyl-3,4-dihydro-1H-pyrimido[4,5-d]pyrimidin-2-one and 300 μl (2.4 mmol) of cyclohexylamine in 2 ml of dichloromethane was stirred at room temperature overnight. The mixture was diluted with 10 ml of dichloromethane, washed with 10 ml of 2M hydrochloric acid and with 10 ml of saturated aqueous sodium bicarbonate solution, dried over magnesium sulfate, filtered and evaporated. 99 mg (96%) of 3-(2,6-dichlorophenyl)-7-cyclohexylamino-3,4-dihydro-1-phenylpyrimido[4,5-d]pyrimidin-2(1H)-one were isolated as a white foam of melting point 258–259° C.

Example 21

A solution of 100 mg (0.22 mmol) of 3-(2,6-dichlorophenyl)-7-methanesulfonyl-1-phenyl-3,4-dihydro-1H-pyrimidof4,5-d]pyrimidin-2-one and 2 ml of methylamine in tetrahydrofuran was stirred at room temperature for 48 hours. The mixture was diluted with 10 ml of ethyl acetate, washed with 10 ml of 2M hydrochloric acid and with 10 ml of saturated aqueous sodium bicarbonate solution, dried over magnesium sulfate, filtered and evaporated. 30 mg (34%) of 3-(2,6-dichlorophenyl)-3,4-dihydro-7-methylamino-1-phenylpyrimido[4,5-d]pyrimidin-2(1H)-one were isolated as a white solid of melting point 211–213° C.

Example 22

A solution of 100 mg (0.22 mmol) of 3-(2,6-dichlorophenyl)-7-methanesulfonyl-1-phenyl-3,4-dihydro-1H-pyrimido[4,5-d]pyrimidin-2-one and 200 mg (2.12 mmol) of 4-aminopyridine in 2 ml of dichloromethane was stirred at room temperature overnight. The mixture was evaporated and the residue was purified by flash column chromatography on silica gel using 10% methanol/dichloromethane for the elution. Product containing fractions were combined and evaporated to give 16 mg (15%) of 3-(2,6-dichlorophenyl)-3,4-dihydro-1-phenyl-7-[(4-pyridyl)amino]pyrimido[4,5-d]pyrimidin-2(1H)-one as an off-white solid which decomposed at 289° C.

Example 23

A solution of 100 mg (0.22 mmol) of 3-(2,6-dichlorophenyl)-7-methanesulfonyl-1-phenyl-3,4-dihydro-1H-pyrimido[4,5-d]pyrimidin-2-one and 285 μl (2.2 mmol) of cyclohexylmethylamine in 2 ml of dichloromethane was stirred at room temperature overnight. The mixture was diluted with 10 ml of dichloromethane, washed with 10 ml of 2M hydrochloric acid and with 10 ml of saturated aqueous sodium bicarbonate solution, dried over magnesium sulfate, filtered and evaporated. 100 mg (94%) of 3-(2,6- dichlorophenyl)-7-(cyclohexylmethylamino)-3,4-dihydro-1-phenylpyrimido[4,5-d]pyrimidin-2(1H)-one were isolated as a white foam of melting point 229–233° C.

Example 24

A mixture of 100 mg (0.22 mmol) of 3-(2,6-dichlorophenyl)-7-methanesulfonyl-1-phenyl-3,4-dihydro-1H-pyrimido[4,5-d]pyrimidin-2-one and 320 mg (2.2 mmol) of 1-aminonaphthalene was heated at 130° C. for 4 hours. The mixture was left to cool and was then partitioned between 10 ml of ethyl acetate and 2M hydrochloric acid. The insoluble 1-aminonaphthalene hydrochloride was removed by filtration. The ethyl acetate phase was separated, washed with 10 ml of saturated aqueous sodium bicarbonate solution, dried over magnesium sulfate, filtered and evaporated. The residue was purified by flash column chromatography on silica gel using ethyl acetate/hexane (1:1) for the elution. Product-containing fractions were evaporated to give 46 mg (40%) of 3-(2,6-dichlorophenyl)-3,4-dihydro-7-(1-naphthylamino)-1-phenylpyrimido[4,5-d]pyrimidin-2(1H)-one as a pale pink solid of melting point 213–214° C.

Example 25

A mixture of 100 mg (0.26 mmol) of 3-(2,6-dichlorophenyl)-3,4-dihydro-7-methanesulfonyl-1-methylpyrimido[4,5-d]pyrimidin-2(1H)-one and 136 mg (1 mmol) of p-xylenediamine was heated at 70° C. for 20 minutes. The product was purified by flash column chromatography on silica gel using dichloromethane/methanol/water/acetic acid (90:18:3:2) for the elution. Product-containing fractions were combined and evaporated. The residue was dissolved in 20 ml of dichloromethane, washed with 20 ml of saturated aqueous sodium bicarbonate solution, dried over magnesium sulfate, filtered and evaporated to give 35 mg (30%) of 7-[4-(aminomethyl)benzylamino]-3-(2,6-dichlorophenyl)-3,4-dihydro-1-methylpyrimido[4,5-d]pyrimidin-2(1H)-one as a white solid of melting point 151–152° C.

Example 26

A mixture of 100 mg (0.26 mmol) of 3-(2,6-dichlorophenyl)-3,4-dihydro-7-methanesulfonyl-1-methylpyrimido[4,5-d]pyrimidin-2(1H)-one and 140 mg (1 mmol) of 2-(4-aminophenyl)ethylamine was heated at 70° C. for 20 minutes. The product was purified by flash column chromatography using 5% methanol in dichloromethane for the elution. Product-containing fractions were combined and evaporated. The residue was recrystallized from ethyl acetate and 3 mg (3%) of 7-[2-(4-aminophenyl)ethylamino]-3-(2,6-dichlorophenyl)-3,4-dihydro-1-methylpyrimido[4,5-d]pyrimidin-2(1H)-one were isolated as a yellow solid of melting point 174–175° C.

Example 27

A mixture of 100 mg (0.26 mmol) of 3-(2,6-dichlorophenyl)-3,4-dihydro-7-methanesulfonyl-1-methylpyrimido[4,5-d]pyrimidin-2(1H)-one and 238 mg (1.07 mmol) of 4-(2-diethylaminoethoxy)benzylamine was heated at 170° C. for 30 minutes. The product was purified by flash column chromatography using dichloromethane/methanol/water/acetic acid (120:14:3:2) for the elution. Product-containing fractions were combined and evaporated to give 40 mg (29%) of 3-(2,6-dichlorophenyl)-7-[4-[2-(diethylamino)ethoxy]benzylamino]-3,4-dihydro-1-methylpyrimido[4,5-d]pyrimidin-2(1H)-one as a white solid of melting point 137–138° C.

The 4-(2-diethylaminoethoxy)benzylamine used as the starting material was prepared as follows:

a) A solution of 8.04 g (67 mmol) of 4-cyanophenol in 100 ml of xylene was treated with a solution of 2.99 g (74 mmol) of sodium hydroxide in 20 ml of water and the mixture was stirred for 30 minutes. To this mixture were added 13.88 g (100 mmol) of potassium carbonate and 12.83 g (75 mmol) of 2-diethylaminoethyl chloride hydrochloride. The resulting mixture was then heated at reflux for 3 hours, subsequently left to cool, washed twice with 50 ml of water each time, dried over magnesium sulfate, filtered and evaporated to give 10.93 g (74%) of 4-(2-diethylaminoethoxy)benzonitrile as a colorless mobile liquid.

b) A 1M solution of lithium aluminium hydride (5 ml; 5 mmol) was added dropwise to a stirred solution of 1.01 g (5 mmol) of 4-(2-diethylaminoethoxy)benzonitrile in 5 ml of dry tetrahydrofuran at 0° C. The mixture was warmed to room temperature and stirred overnight. The reaction was quenched by the cautious addition of a saturated solution of 5 ml of Rochelle's salt and then evaporated. The residue was partitioned between 25 ml of diethyl ether and 25 ml of water and the organic phase was separated, dried over magnesium sulfate and evaporated. The crude product was purified by flash column chromatography on silica gel using dichloromethane/methanol/water/acetic acid (60:18:2:3) for the elution. Product-containing fractions were combined and evaporated to give 785 mg (71%) of 4-(2-diethylaminoethoxy)benzylamine as a colorless oil. [Mass spectrum (ESI) MH$^+$=223].

Example 28

A mixture of 65 mg (0.19 mmol) of 3-(2,6-dimethylphenyl)-7-methanesulfonyl-3,4-dihydro-1-methylpyrimido[4,5-d]pyrimidin-2(1H)-one and 180 mg (0.87 mmol) of 4-[2-(diethylamino)ethoxy]aniline was heated at 180° C. for 30 minutes and then cooled. The residue was subjected to column chromatography on silica gel using dichloromethane/methanol/acetic acid/water (240:24:3:2) for the elution. Product-containing fractions were combined and evaporated and the residue was evaporated with toluene. The residue was dissolved in 20 ml of dichloromethane, washed three times with 20 ml of saturated aqueous sodium bicarbonate solution each time, dried over magnesium sulfate, filtered and evaporated to give 15 mg of a pink oil which was purified by HPLC. The mobile phase was water/0.1% trifluoroacetic acid (A) and acetonitrile/0.07% trifluoroacetic acid (B); the gradient was 5%–95% B over 20 minutes; and the product was detected using an ultraviolet detector at a wavelength of 215 nm. Product-containing fractions were lyophilized and the lyophilisate was dissolved in 20 ml of dichloromethane, washed three times with 20 ml of saturated aqueous sodium bicarbonate solution each time, dried over magnesium sulfate, filtered and evaporated to give 10 mg (11%) of 7-[4-[2-(diethylamino)ethoxy]anilino]-3,4-dihydro-1-methyl-3-(2,6-dimethylphenyl)pyrimido[4,5-d]pyrimidin-2(1H)-one as a white solid of melting point 58° C.

The 3-(2,6-dimethylphenyl)-7-methanesulfonyl-3,4-dihydro-1-methylpyrimido[4,5-d]pyrimidin-2(1H)-one used as the starting material was prepared as follows:

a) To a mixture of 200 mg (1.1 mmol) of 4-methylamino-2-methylthiopyrimidine-5-carboxaldehyde and 0.15 ml (1.2 mmol) of 2,6-dimethylaniline in 5 ml of dichloromethane were added 350 mg (1.6 mmol) of sodium triacetoxyborohydride and then 0.1 ml (1.7 mmol) of acetic acid. After 5 hours a further 0.15 ml of 2,6-dimethylaniline was added and the mixture was stirred at room temperature for 18 hours. 20 ml of saturated aqueous sodium bicarbonate solution and 25 ml of dichloromethane were added. The phases were separated and the aqueous phase was washed twice with 25 ml of dichloromethane. The combined organic solutions were dried over magnesium sulfate, filtered and evaporated. The residue was subjected to column chromatography on silica gel using diethyl ether/hexane (1:2) for the elution. Product-containing fractions were combined and evaporated to give 40 mg (13%) of 5-(2,6-dimethylphenyl) aminomethyl-4-methylamino-2-methylthiopyrimidine as a white solid [mass spectrum (ESI) MH$^+$=289] and 200 mg (65%) of 5-(2,6-dimethylphenyl)iminomethyl-4-methylamino-2-methylthiopyrimidine as a white solid. [Mass spectrum (ESI) MH$^+$=287].

b) A mixture of 195 mg (0.68 mmol) 5-(2,6-dimethylphenyl) aminomethyl-4-methylamino-2-methylthiopyrimidine and 0.19 ml (1.4 mmol) of triethylamine in 10 ml of dioxan was added dropwise to an ice-cooled solution of 0.085 ml (0.7 mmol) of trichloromethyl chloroformate in 10 ml of dioxan. The mixture was then left to warm to room temperature. After a further 10 minutes the mixture was evaporated. To the residue were added 40 ml of dichloromethane and 40 ml of saturated aqueous sodium bicarbonate. The phases were separated and the dichloromethane phase was dried over magnesium sulfate, filtered and evaporated. The residue was dissolved in 15 ml of pyridine and heated at reflux for 1 hour. The mixture was cooled and evaporated. The residue was partitioned between 20 ml of dichloromethane and 20 ml of 2M hydrochloric acid. The organic phase was washed with 20 ml of water, dried over magnesium sulfate and evaporated to give 100 mg (47%) of 3-(2,6-dimethylphenyl)-7-methylthio-3,4-dihydro-1-methylpyrimido[4,5-d]pyrimidin-2(1H)-one as an off-white solid. [Mass spectrum (ESI) MH$^+$=315].

c) A solution of 100 mg (0.32 mmol) of 3-(2,6-dimethylphenyl)-7-methylthio-3,4-dihydro-1-methylpyrimido[4,5-d]pyrimidin-2(1H)-one in 10 ml of dichloromethane was treated with 220 mg (0.64 mmol) of 3-chloroperbenzoic acid (50% w/w in water). After 18 hours 30 ml of saturated aqueous sodium bicarbonate solution and 20 ml of dichloromethane were added and the phases were separated. The organic phase was dried over magnesium sulfate, filtered and evaporated to give 65 mg (59%) of 3-(2,6-dimethylphenyl)-7-methanesulfonyl-3,4-dihydro-1-methylpyrimido[4,5-d]pyrimidin-2(1H)-one as a white solid. [Mass spectrum (ESI) MH$^+$=347].

Example 29

A mixture of 250 mg (0.67 mmol) of 3-(2,6-dichlorophenyl)-7-methanesulfonyl-3,4-dihydropyrimido[4,5-d]pyrimidin-2(1H)-one and 600 mg (2.9 mmol) of 4-[2-(diethylamino)ethoxy]aniline was heated at 180° C. for 35 minutes and then cooled. The residue was subjected to column chromatography on silica gel using dichloromethane/methanol/acetic acid/water 240:24:3:2 for the elution. Product-containing fractions were combined and evaporated and the residue was evaporated with toluene. The residue was dissolved in 30 ml of dichloromethane, washed twice with 20 ml of saturated aqueous sodium bicarbonate solution each time, dried over magnesium sulfate, filtered and evaporated. The residue was triturated in hexane, filtered off and dried to give 70 mg (21%) of 3-(2,6-dichlorophenyl)-7-[4-[2-(diethylamino)ethoxy]anilino]-3,4-dihydropyrimido[4,5-d]pyrimidin-2(1H)-one as an off-white solid of melting point 248° C.

Example 30

A mixture of 70 mg (0.16 mmol) of 3-(2,6-dichlorophenyl)-1-isopropyl-7-methanesulfonyl-3,4-dihydropyrimido[4,5-d]pyrimidin-2(1H)-one and 166 mg (0.8 mmol) of 4-[2-diethylamino)ethoxy]aniline was heated at 180° C. for 35 minutes and then cooled. The residue was subjected to column chromatography on silica gel using dichloromethane/methanol/acetic acid/water (240:24:3:2) for the elution. Product-containing fractions were combined and evaporated and the residue was evaporated with toluene. The residue was then dissolved in 30 ml of dichloromethane, washed twice with 20 ml of saturated aqueous sodium bicarbonate solution each time, dried over magnesium sulfate, filtered and evaporated to give 5 mg (22%) of 3-(2,6-dichlorophenyl)-7-[4-[2-(diethylamino)ethoxy] anilino]-3,4-dihydro-1-isopropylpyrimido[4,5-d]pyrimidin-2(1H)-one as a white solid of melting point 125° C.

The 3-(2,6-dichlorophenyl)-1-isopropyl-7-methanesulfonyl-3,4-dihydropyrimido[4,5-d]pyrimidin-2 (1H)-one used as the starting material was prepared as follows:

a) A solution, cooled in ice, of 100 mg (0.27 mmol) of 3-(2,6-dichlorophenyl)-7-methylthio-3,4-dihydropyrimido [4,5-d]pyrimidin-2(1H)-one in 6 ml of dimethylformamide was treated with 13 mg (0.33 mmol) of sodium hydride (60% w/w). After 30 minutes the mixture was treated with 0.03 ml (0.3 mmol) of 2-bromopropane and then heated to 90° C. for 2 hours, cooled and left to stand for 3 days. The mixture was evaporated and the residue was treated with 30 ml of dichloromethane and 30 ml of water. The phases were separated and the organic phase was washed with 30 ml of water, dried over magnesium sulfate, filtered and evaporated to give 60 mg (54%) of 3-(2,6-dichlorophenyl)-1-isopropyl-7-methylthio-3,4-dihydropyrimido[4,5-d]pyrimidin-2(1H)-one as a yellow solid. [Mass spectrum (ESI) MH$^+$=383].

b) A solution of 60 mg (0.16 mmol) of 3-(2,6-dichlorophenyl)-1-isopropyl-7-methylthio-3,4-dihydropyrimido[4,5-d]pyrimidin-2(1H)-one in 10 ml of dichloromethane was treated with 108 mg (0.32 mmol) of 3-chloroperbenzoic acid (50% w/w in water) and stirred for 18 hours. 0.2 ml of dimethyl sulfoxide was added. After a further 15 minutes 15 ml of saturated aqueous sodium bicarbonate solution were added and the phases were separated. The organic phase was washed with 30 ml of saturated aqueous sodium bicarbonate solution, dried over magnesium sulfate and evaporated to give 65 mg (100%) of 3-(2,6-dichlorophenyl)-1-isopropyl-7-methanesulfonyl-3,4-dihydropyrimido[4,5-d]pyrimidin-2(1H)-one as a white solid. [Mass spectrum (ESI) MH$^+$=415].

Example 31

A mixture of 200 mg (0.6 mmol) of 3-(2-methylphenyl)-7-methanesulfonyl-3,4-dihydro-1-methylpyrimido[4,5-d] pyrimidin-2(1H)-one and 300 mg (1.4 mmol) of 4-[2-(diethylamino)ethoxy]aniline was heated at 180° C. for 35 minutes and then cooled. The residue was subjected to column chromatography on silica gel using dichloromethane/methanol/acetic acid/water (240:24:3:2) for the elution combined and evaporated and the residue was evaporated with toluene. The residue was dissolved in 30 ml of dichloromethane, washed twice with 20 ml of saturated aqueous sodium bicarbonate solution each time, dried over magnesium sulfate, filtered and evaporated to give 30 mg (11%) of 7-[4-[2-(diethylamino)ethoxy]anilino]-3,4-dihydro-1-methyl-3-(2-methylphenyl)pyrimido[4,5-d] pyrimidin-2(1H)-one as a pink solid of melting point 132° C.

The 3-(2-methylphenyl)-7-methanesulfonyl-3,4-dihydro-1-methylpyrimido[4,5-d]pyrimidin-2(1H)-one used as the starting material was prepared as follows:

a) A mixture of 300 mg (1.6 mmol) of 4-methylamino-2-methylthiopyrimidine-5-carboxaldehyde, 0.20 ml (1.8 mmol) of o-toluidine and 59 mg (0.3 mmol) of 4-toluenesulfonic acid in 50 ml of toluene was heated at reflux with azeotropic removal of water for 18 hours. The mixture was cooled and evaporated. The residue was dissolved in 40 ml of ethanol and heated to 70° C. 300 mg (8 mmol) of sodium borohydride were added cautiously and the mixture was heated at 70° C. for 2 hours. A further 300 mg (0.8 mmol) of sodium borohydride were added cautiously and the heating was continued for a further hour. The mixture was cooled and then evaporated. The residue was partitioned between 50 ml of 2M aqueous sodium hydroxide solution and 50 ml of ethyl acetate. The organic phase was dried over magnesium sulfate, filtered and evaporated. The residue was subjected to column chromatography on silica gel using diethyl ether/hexane (1:1) for the elution. Product-containing fractions were combined and evaporated to give 190 mg (43%) of 5-(2-methylphenyl)aminomethyl-4-methylamino-2-methylthiopyrimidine as a white solid. [Mass spectrum (ESI) MH$^+$=275].

b) A stirred solution, cooled in ice, of 0.7 ml (1.3 mmol) of phosgene (20% in toluene) in 5 ml of tetrahydrofuran was treated dropwise with a solution containing 189 mg (0.69 mmol) of 5-(2-methylphenyl)aminomethyl-4-methylamino-2-methylthiopyrimidine and 0.2 ml (1.4 mmol) of triethylamine in 5 ml of tetrahydrofuran. The mixture was stirred for 1 hour. To the mixture were added 20 ml of tetrahydrofuran and 20 ml of saturated aqueous ammonium chloride solution. The phases were separated and the organic phase was dried over magnesium sulfate, filtered and evaporated to give 210 mg (100%) of 3-(2-methylphenyl)-7-methylthio-3,4-dihydro-1-methylpyrimido[4,5-d]pyrimidin-2(1H)-one as a cream-colored solid. [Mass spectrum (ESI) MH$^+$=301].

c) A solution of 210 mg (0.7 mmol) of 3-(2-methylphenyl)-7-methylthio-3,4-dihydro-1-methylpyrimido[4,5-d]pyrimidin-2(1H)-one in 10 ml of dichloromethane was treated with 482 mg (1.4 mmol) of 3-chloroperbenzoic acid (50% w/w in water). After 18 hours 40 ml of saturated aqueous sodium bicarbonate and 40 ml of dichloromethane were added and the phases were separated. The organic phase was dried over magnesium sulfate, filtered and evaporated to give 200 mg (86%) of 3-(2-methylphenyl)-7-methanesulfonyl-3,4-dihydro-1-methylpyrimido[4,5-d]pyrimidin-2(1H)-one as a white solid. [Mass spectrum (ESI) MH$^+$=) 333].

Example 32

A mixture of 40 mg (0.096 mmol) of 3-(2,6-dichlorophenyl)-7-methanesulfonyl-3,4-dihydro-1-phenylpyrimido[4,5-d]pyrimidin-2(1H)-one and 1 ml (11 mmol) of aniline was heated at 180° C. for 45 minutes, cooled and partitioned between 30 ml of ethyl acetate and 30 ml of 2M hydrochloric acid. The separated organic phase was dried over magnesium sulfate, filtered and evaporated. The residue was subjected to column chromatography on silica gel using ethyl acetate/hexane (1:2) for the elution. Product-containing fractions were combined and evaporated to give a tan solid which was purified further by HPLC. The mobile phase was water/0.1% trifluoroacetic acid (A) and acetonitrile/0.07% trifluoroacetic acid (B); the gradient was 5%–95% B over 20 minutes; and the product was detected with an ultraviolet detector at a wavelength of 215 nm. The product-containing fraction was lyophilized to give 5 mg (4%) of 7-anilino-3-(2,6-dichlorophenyl)-3,4-dihydro-1-phenylpyrimido[4,5-d]pyrimidin-2(1H)-one as a white solid of melting point 138° C.

Example 33

A mixture of 56 mg (0.13 mmol) of 3-(2,6-dichlorophenyl)-7-methanesulfonyl-3,4-dihydro-1-phenylpyrimido[4,5-d]pyrimidin-2(1H)-one and 1 ml of 4-methoxybenzylamine was heated at 100° C. for 30 minutes, then cooled and partitioned between 30 ml of dichloromethane and 30 ml of 2M hydrochloric acid. The organic phase was dried over magnesium sulfate, filtered and evaporated to give 68 mg (100%) of 3-(2,6-dichlorophenyl)-3,4-dihydro-7-(4-methoxybenzyl)amino-1-phenylpyrimido[4,5-d]pyrimidin-2(1H)-one as a yellow solid of melting point 56° C.

Example 34

A solution of 40 mg (0.96 mmol) of 3-(2,6-dichlorophenyl)-7-(4-methoxybenzyl)amino-3,4-dihydro-1-phenylpyrimido[4,5-d]pyrimidin-2(1H)-one in 5 ml of trifluoroacetic acid was heated at reflux for 5 hours. The mixture was evaporated and the residue was partitioned between 30 ml of ethyl acetate and 30 ml of 2M aqueous sodium hydroxide. The organic phase was dried over magnesium sulfate, filtered and evaporated and the residue was subjected to column chromatography on silica gel using dichloromethane/methanol (20:1) for the elution. Product-containing fractions were combined and evaporated to give 10 mg (27%) of 7-amino-3-(2,6-dichlorophenyl)-3,4-dihydro-1-phenylpyrimido[4,5-d]pyrimidin-2(1H)-one as a white solid of melting point >300° C.

Example 35

A mixture of 200 mg (0.56 mmol) of 3-(2,6-difluorophenyl)-7-methanesulfonyl-3,4-dihydro-1-methylpyrimido[4,5-d]pyrimidin-2(1H)-one and 400 mg (1.9 mmol) of 4-[1288 2-(diethylamino)ethoxy]aniline was heated at 180° C. for 30 minutes and then cooled. The residue was subjected to column chromatography on silica gel using dichloromethane/methanol/acetic acid/water (240:24:3:2) for the elution. Product-containing fractions were combined and evaporated and the residue was evaporated with toluene. The residue was then dissolved in 40 ml of dichloromethane, washed with 40 ml of saturated aqueous sodium bicarbonate solution, dried over magnesium sulfate, filtered and evaporated to give 30 mg (11%) of 7-[4-[2-(diethylamino)ethoxy]anilino]-3-(2,6-difluorophenyl)-3,4-dihydro-1-methylpyrimido[4,5-d]pyrimidin-2(1H)-one as an orange colored solid. [Mass spectrum (ESI) MH$^+$=483].

The 3-(2,6-difluorophenyl)-7-methanesulfonyl-3,4-dihydro-1-methylpyrimido[4,5-d]pyrimidin-2(1H)-one used as the starting material was prepared as follows:

a) A mixture of 300 mg (1.6 mmol) of 4-methylamino-2-methylthiopyrimidine-5-carboxaldehyde, 232 mg (1.8 mmol) of 2,6-difluoroaniline and 59 mg (0.3 mmol) of 4-toluenesulfonic acid monohydrate in 30 ml of toluene was heated at reflux with azeotropic removal of water for 18 hours. The mixture was cooled and evaporated. The residue was dissolved in 20 ml of tetrahydrofuran and added dropwise to a solution of 1.6 ml (1.6 mmol) of lithium aluminium hydride (1M in tetrahydrofuran) in a further 20 ml of tetrahydrofuran. After 30 minutes the mixture was cooled in ice and 0.5 ml of water, 0.75 ml of 2M sodium hydroxide solution and finally 1 ml of water were cautiously added dropwise. The resulting suspension was filtered through a filter aid and the filtrate was evaporated. The residue was subjected to column chromatography on silica gel using diethyl ether/hexane (1:1) for the elution to yield 210 mg (44%) of 5-(2,6-difluorophenyl)aminomethyl-4-methylamino-2-methylthiopyrimidine as a white solid. [Mass spectrum (ESI) MH$^+$=297].

b) A stirred solution, cooled in ice, of 0.7 ml (1.3 mmol) of phosgene (20% in toluene) in 5 ml of tetrahydrofuran was treated dropwise with a solution of 210 mg (0.71 mmol) of 5-(2,6-difluorophenyl)aminomethyl-4-methylamino-2-methylthiopyrimidine and 0.2 ml (1.4 mmol) of triethylamine in 5 ml of tetrahydrofuran. The mixture was stirred for 1 hour. To the mixture were added 20 ml of tetrahydrofuran and 20 ml of saturated aqueous ammonium chloride solution and the phases were separated. The organic phase was dried over magnesium sulfate, filtered and evaporated to give 200 mg (87%) of 3-(2,6-difluorophenyl)-7-methylthio-3,4-dihydro-1-methylpyrimido[4,5-d]pyrimidin-2(1H)-one as a white solid. [Mass spectrum (ESI) MH$^+$=323].

c) A solution of 200 mg (0.62 mmol) of 3-(2,6-difluorophenyl)-7-methylthio-3,4-dihydro-1-methylpyrimido[4,5-d]pyrimidin-2(1H)-one in 10 ml of dichloromethane was treated with 430 mg (1.24 mmol) of 3-chloroperbenzoic acid (50% w/w water). After 18 hours 40 ml of saturated aqueous sodium bicarbonate solution and 40 ml of dichloromethane were added and the phases were separated. The organic phase was dried over magnesium sulfate, filtered and evaporated to give 200 mg (91%) of 3-(2,6-difluorophenyl)-7-methanesulfonyl-3,4-dihydro-1-methylpyrimido[4,5-d]pyrimidin-2(1H)-one as a white solid. [Mass spectrum (ESI) MH$^+$=355].

Example 36

A mixture of 200 mg (0.52 mmol) of 3-(2,4-dichlorophenyl)-7-methanesulfonyl-3,4-dihydro-1-methylpyrimido[4,5-d]pyrimidin-2(1H)-one and 300 mg (1.4 mmol) of 4-[2-(diethylamino)ethoxy]aniline was heated at 180° C. for 30 minutes and then cooled. The residue was subjected to column chromatography on silica gel using dichloromethane/methanol/acetic acid/water (240:24:3:2) for the elution. Product-containing fractions were combined and evaporated and the residue was evaporated with toluene. The residue was then dissolved in 40 ml of dichloromethane, washed with 40 ml of saturated aqueous sodium bicarbonate solution, dried over magnesium sulfate, filtered and evaporated to give 20 mg (8%) of 3-(2,4-dichlorophenyl)-7-[4-[2-(diethylamino)ethoxy]anilino]-3,4-dihydro-1-methylpyrimido[4,5-d]pyrimidin-2(1H)-one as an orange colored solid of melting point 172° C.

The 3-(2,4-dichlorophenyl)-7-methanesulfonyl-3,4-dihydro-1-methylpyrimido[4,5-d]pyrimidin-2(1H)-one used as the starting material was prepared in a manner analogous to that described in Example 35 for 3-(2,6-difluorophenyl)-7-methanesulfonyl-3,4-dihydro-1-methylpyrimido[4,5-d]pyrimidin-2(1H)-one using 2,4-dichloroaniline in place of 2,6-difluoroaniline.

Example 37

A mixture of 200 mg (0.52 mmol) of 3-(2,6-dichlorophenyl)-7-methanesulfonyl-3,4-dihydro-1-[3-(2-phthalimidoethyl)phenyl]pyrimido[4,5-d]pyrimidin-2(1H)-one and 3 ml of aniline was heated at 180° C. for 40 minutes and then cooled. The mixture was partitioned between 40 ml of dichloromethane and 40 ml of 2M hydrochloric acid. The organic phase was dried over magnesium sulfate, filtered and evaporated. The residue was subjected to column chromatography on silica gel using diethyl ether/hexane (1:1) for the elution. The product-containing fractions were combined and evaporated to give 30 mg (29%) of 7-anilino3-(2,6-dichlorophenyl)-3,4-dihydro-1-[3-(2-phthalimidoethyl)phenyl]pyrimido[4,5-d]pyrimidin-2(1H)-one as a white solid of melting point 142° C.

The 3-(2,6-dichlorophenyl)-7-methanesulfonyl-3,4-dihydro-1-[3-(2-phthalimidoethyl)phenyl]pyrimido[4,5-d]pyrimidin-2(1H)-one used as the starting material was prepared as follows:

a) To a solution of 10 g (60 mmol) of 3-nitrophenylacetic acid in 120 ml of ethanol were added 20 ml of a saturated solution of hydrogen chloride in ethyl acetate and the mixture was heated at reflux for 4 hours, cooled and left to stand at room temperature for 18 hours. The mixture was evaporated and the residue was partitioned between 120 ml of diethyl ether and 100 ml of saturated aqueous sodium bicarbonate solution. The organic phase was dried over magnesium sulfate, filtered and evaporated to give 10.3 g (82%) of ethyl 3-nitrophenylacetate as a pale yellow oil. [NMR spectrum (250 MHz) δ1.25(t) (3H), δ3.68(s) (2H), δ4.6(q) (2H), δ6.5–δ6.7(m) (3H), δ7.09(dd) (1H)].

b) A solution of 10.3 g (49 mmol) of ethyl 3-nitrophenylacetate in 120 ml of ethanol was hydrogenated over 1 g of 10% palladium on charcoal for 6 hours. The mixture was filtered and the filtrate evaporated to give 9.3 g (100%) of ethyl 3-aminophenylacetate as a yellow oil. [NMR spectrum (250 MHz) δ1.19(t) (3H), δ3.48(s) (2H), δ4.16(q) (2H), δ7.48(dd) (1H), δ7.62(d) (1H), δ8.12(m) (2H)].

c) A mixture of 5 g (21.5 mmol) of ethyl 4-chloro-2-methylthio-pyrimidine-5-carboxylate and 4 g (22.3 mmol) of ethyl 3-aminophenylacetate in 80 ml of 1,4-dioxan was treated with 6 ml (43 mmol) of triethylamine and then heated at 60° C. for 4 hours. The mixture was cooled and evaporated. The residue was partitioned between 120 ml of ethyl acetate and 100 ml of 2M hydrochloric acid. The organic phase was dried over magnesium sulfate, filtered and evaporated to give 7.4 g (92%) of ethyl 4-[3-(ethoxycarbonylmethyl)phenyl]amino-2-methylthiopyrimidine-5-carboxylate as a pale orange colored oil which solidifies slowly to a white solid. [Mass spectrum (ESI) MH$^+$=376].

d) To a solution, cooled in ice, of 1.3 g (34 mmol) of lithium aluminium hydride in 70 ml of tetrahydrofuran was added dropwise a solution of 6.5 g (17 mmol) of ethyl 4-[3-(ethoxycarbonylmethyl)phenyl]amino-2-methylthiopyrimidine-5-carboxylate in 70 ml of tetrahydrofuran. The cooling was removed and the mixture was stirred at room temperature for 2 hours. The reaction was quenched by the cautious dropwise addition of 1.2 ml of water, 1.2 ml of 2M aqueous sodium hydroxide and finally 3.6 ml of water. The resulting suspension was filtered through a filter aid and the filtrate was evaporated. The residue was subjected to column chromatography on silica gel using dichloromethane/methanol (10:1) for the elution. Product-containing fractions were combined and evaporated to give 3.1 g (62%) of 5-hydroxymethyl-4-[3-(2-hydroxyethyl)phenyl]amino-2-methylthiopyrimidine as a yellow oil. [Mass spectrum (ESI) MH$^+$=292].

e) To a solution of 3.1 g (10.7 mmol) of 5-hydroxymethyl-4-[3-(2-hydroxyethyl)phenyl]amino-2-methylthiopyrimidine in 250 ml of dichloromethane were added 9 g (100 mmol) of manganese dioxide and the mixture was stirred for 24 hours. The mixture was filtered through a filter aid and the filtrate was evaporated to give 2.6 g (84%) of 5-formyl-4-(3-(2-hydroxyethyl)phenylamino-2-methylthiopyrimidine as a white solid. [Mass spectrum (ESI) MH$^+$=290].

f) A solution of 4 g (13.8 mmol) of 5-formyl-4-[3-(2-hydroxyethyl)phenyl]amino-2-methylthiopyrimidine in 80 ml of toluene was treated with 2.4 g (15 mmol) of 2,6-dichloroaniline and 0.25 g (1.3 mmol) of 4-toluenesulfonic acid monohydrate and the mixture was heated under reflux with azeotropic removal of water for 18 hours and then cooled. The mixture was evaporated and the residue was dissolved in 40 ml of tetrahydrofuran and added dropwise to a solution of 0.6 g (16 mmol) of lithium aluminium hydride in 40 ml of tetrahydrofuran. After 1 hour the reaction was quenched by the cautious dropwise addition of 0.6 ml of water, 0.6 ml of 2M aqueous sodium hydroxide and 1.8 ml of water. The resulting suspension was filtered through a filter aid and the filtrate was evaporated. The residue was subjected to column chromatography on silica using dichloromethane/methanol for the elution in a gradient from a ratio of 50:1 to a ratio of 10:1. Product-containing fractions from the first product to be eluted from the column were combined and evaporated to give 1 g (17%) of 5-(2,6-dichloroanilino)methyl-4-[3-(2-hydroxyethyl)phenyl] amino-2-methylthiopyrimidine as a white solid. Mass spectrum (ESI) MH$^+$=435. Product-containing fractions from the second product to be eluted from the column were combined and evaporated to give 1.8 g (45%) of 5-hydroxymethyl-4-[3-(2-hydroxyethyl)phenyl]amino-2-methylthiopyrimidine as a white solid. [Mass spectrum (ESI) MH$^+$=292].

g) A solution of 1 g (2.3 mmol) of 5-(2,6-dichloroanilino) methyl-4-[3-(2-hydroxyethyl)phenyl]amino-2-methylthiopyrimidine in 60 ml of tetrahydrofuran was treated with 0.8 ml (6 mmol) of triethylamine and the mixture was added dropwise to a solution of 1.8 ml of phosgene (20% in toluene) in 40 ml of tetrahydrofuran. The cooling was removed. After 2 hours 100 ml of saturated aqueous ammonium chloride solution were added. The mixture was separated and the organic phase was dried over magnesium sulfate, filtered and evaporated. The residue was subjected to column chromatography on silica gel using diethyl ether/hexane (1:2) for the elution. Product-containing fractions were combined and evaporated to give 0.5 g (50%) of 3-(2,6-dichlorophenyl)-7-methylthio-3,4-dihydro-1-[3-(2-chloroethyl)phenyl]pyrimido[4,5-d] pyrimidin-2(1H)-one as a white solid. [Mass spectrum (ESI) MH$^+$=479].

h) A solution of 0.5 g (1.1 mmol) of 3-(2,6-dichlorophenyl)-7-methylthio-3,4-dihydro-1-(3-(2-chloroethyl)phenyl) pyrimido[4,5-d]pyrimidin-2(1H)-one in 30 ml of dimethylformamide was treated with 0.2 g (1.1 mmol) of phthalimide potassium salt and the mixture was heated at 80° C. for 2 hours. The cooled mixture was evaporated and partitioned between 40 ml of dichloromethane and 40 ml of water. The organic phase was dried over magnesium sulfate, filtered and evaporated. The residue was subjected to column chromatography on silica gel using diethyl ether/hexane (1:1) for the elution. Product-containing fractions were combined and evaporated to give 0.43 g (70%) of 3-(2,6-dichlorophenyl)-7-methylthio-3,4-dihydro-1-[3-(2-phthalimidoethyl)phenyl] pyrimido[4,5-d]pyrimidin-2(1H)-one as a white solid. [Mass spectrum (ESI) MH$^+$=590].

i) A solution of 400 mg (0.68 mmol) of 3-(2,6-dichlorophenyl)-7-methylthio-3,4-dihydro-1-[3-(2-phthalimidoethyl)phenyl]pyrimido[4,5-d]pyrimidin-2(1H)-one in 20 of dichloromethane was treated with 470 mg (1.36 mmol) of 3-chloroperbenzoic acid (50% w/w in water). After 18 hours 40 ml of saturated aqueous sodium bicarbonate solution and 40 ml of dichloromethane were added and the phases were separated. The organic phase was dried over magnesium sulfate, filtered and evaporated to give 370 mg (88%) of 3-(2,6-dichlorophenyl)-7-methanesulfonyl-3,4-dihydro-1-[3-(2-phthalimido-ethyl)phenyl]pyrimido[4,5-d]pyrimidin-2(1H)-one as a white solid. [Mass spectrum (ESI) MH$^+$=622].

Example 38

A solution of 30 mg (0.05 mmol) of 3-(2,6-dichlorophenyl)-7-anilino-3,4-dihydro-1-[3-(2-phthalimidoethyl)phenyl]pyrimido[4,5-d]pyrimidin-2(1H)-one in 5 ml of ethanol was treated with 0.02 ml of hydrazine hydrate. After 5 hours the mixture was evaporated and 10 ml of dichloromethane were added to the residue. The resulting suspension was filtered and the filtrate was evaporated. The residue was subjected to column chromatography on silica gel using dichloromethane/methanol/acetic acid/water (240:24:3:2) for the elution. Product-containing fractions were combined and evaporated and the residue was evaporated with toluene. The residue was then dissolved in 40 ml of dichloromethane, washed with 40 ml of saturated aqueous sodium bicarbonate solution, dried over magnesium sulfate, filtered and evaporated to give 12 mg (50%) of 1-[3-(2-aminoethyl)phenyl]-7-anilino-3-( 2,6-dichlorophenyl)-3,4-dihydropyrimido[4,5-d]pyrimidin-2(1H)-one as a white solid of melting point 208° C.

Example 39

A mixture of 250 mg (0.98 mmol) of 3-methyl-7-methanesulfonyl-3,4-dihydro-1-methylpyrimido[4,5-d] pyrimidin-2(1H)-one and 560 mg (2.7 mmol) of 4-[2-(diethylamino)ethoxy]aniline was heated at 180° C. for 35 minutes and then cooled. The residue was subjected to column chromatography on silica gel using dichloromethane/methanol/acetic acid/water (240:24:3:2) for the elution. Product-containing fractions were combined and evaporated and the residue was evaporated with toluene. The residue was then dissolved in 40 ml of dichloromethane, washed with 40 ml of saturated aqueous sodium bicarbonate solution, dried over magnesium sulfate, filtered and evaporated. The residue was triturated in hexane, filtered off and dried to give 23 mg (7%) of 7-[4-[2-(diethylamino)ethoxy] anilino]-3,4-dihydro-1,3-dimethylpyrimido[4,5-d] pyrimidin-2(1H)-one as a white solid of melting point 186° C.

The 3-methyl-7-methanesulfonyl-3,4-dihydro-1-methylpyrimido[4,5-d]pyrimidin-2(1H)-one used as the starting material was prepared in a manner analogous to that described in Example 4 for 3-cyclohexyl-7-methanesulfonyl-3,4-dihydro-1-methylpyrimido[4,5-d] pyrimidin-2(1H)-one using methylamine (as a 2M solution in tetrahydrofuran) in place of cyclohexylamine.

Example 40

A mixture of 160 mg (0.45 mmol) of 3-(2-chloro-6-methylphenyl)-7-methanesulfonyl-3,4-dihydro-1-methylpyrimido[4,5-d]pyrimidin-2(1H)-one and 300 mg (1.4 mmol) of 4-[2-(diethylamino)ethoxy]aniline was heated at 180° C. for 35 minutes and then cooled. The residue was subjected to column chromatography on silica gel using dichloromethane/methanol/acetic acid/water (240:24:3:2) for the elution. Product-containing fractions were combined and evaporated and the residue was evaporated with toluene. The residue was then dissolved in 30 ml of dichloromethane, washed twice with 20 ml of saturated aqueous sodium bicarbonate solution each time, dried over magnesium sulfate, filtered and evaporated. The residue was purified further by HPLC. The mobile phase was water/0.1% trifluoroacetic acid (A) and acetonitrile/0.07% trifluoroacetic acid (B); the gradient was 5%–95% B over 20 minutes; and the product was detected using an ultraviolet detector at a wavelength of 215 nm. Product-containing fractions were lyophilized and the lyophilisate was dissolved in 30 ml of dichloromethane, washed twice with 20 ml of saturated aqueous sodium bicarbonate solution each time, dried over magnesium sulfate, filtered and evaporated to give 5 mg (2%) of 3-(2-chloro-6-methylphenyl)-7-[4-[2-(diethylamino)ethoxy]anilino]-3,4-dihydro-1-methylpyrimido[4,5-d]pyrimidin-2(1H)-one as a yellow gum. [Mass spectrum (ESI) MH+=495].

The 3-(2-chloro-6-methylphenyl)-7-methanesulfonyl-3,4-dihydro-1-methylpyrimido[4,5-d]pyrimidin-2(1H)-one used as the starting material was prepared in a manner analogous to that described in Example 35 for 3-(2,6-difluorophenyl)-7-methanesulfonyl-3,4-dihydro-1-methylpyrimido[4,5-d]pyrimidin-2(1H)-one using 2-chloro-6-methylaniline in place of 2,6-difluoroaniline.

Example 41

A mixture of 350 mg (1.2 mmol) of 3-isopropyl-7-methanesulfonyl-3,4-dihydro-1-methylpyrimido[4,5-d]pyrimidin-2(1H)-one and 500 mg (2.4 mmol) of 4-[2-(diethylamino)ethoxy]aniline was heated at 180° C. for 35 minutes and then cooled. The residue was subjected to column chromatography on silica gel using dichloromethane/methanol/acetic acid/water (240:24:3:2) for the elution. Product-containing fractions were combined and evaporated and the residue was evaporated with toluene. The residue was then dissolved in 40 ml of dichloromethane, washed with 40 ml of saturated aqueous sodium bicarbonate solution, dried over magnesium sulfate, filtered and evaporated. The residue was triturated in hexane, filtered off and dried to give 40 mg (8%) of 7-[4-[2-(diethylamino)ethoxy]anilino]-3,4-dihydro-3-isopropyl-1-methylpyrimido[4,5-d]pyrimidin-2(1H)-one as a white solid of melting point 154° C.

The 3-isopropyl-7-methanesulfonyl-3,4-dihydro-1-methylpyrimido[4,5-d]pyrimidin-2(1H)-one used as the starting material was prepared in a manner analogous to that described in Example 4 for 3-cyclohexyl-7-methanesulfonyl-3,4-dihydro-1-methylpyrimido[4,5-d]pyrimidin-2(1H)-one using isopropylamine in place of cyclohexylamine.

Example 42

A mixture of 70 mg (0.15 mmol) of 3-(2,6-dichlorophenyl)-1-[2-cyclohexen-1(RS)-yl]-7-methanesulfonyl-3,4-dihydropyrimido[4,5-d]pyrimidin-2(1H)-one and 150 mg (0.7 mmol) of 4-[2-(diethylamino)ethoxy]aniline was heated at 180° C. for 35 minutes and then cooled. The residue was subjected to column chromatography on silica gel using dichloromethane/methanol/acetic acid/water (240:24:3:2) for the elution. Product-containing fractions were combined and evaporated and the residue was evaporated with toluene. The residue was then dissolved in 30 ml of dichloromethane, washed twice with 20 ml of saturated aqueous sodium bicarbonate solution each time, dried over magnesium sulfate, filtered and evaporated to give 5 mg (22%) of 3-(2,6-dichlorophenyl)-1-[2-cyclohexen-1(RS)-yl]-7-[4-[2-(diethylamino)ethoxy]anilino]-3,4-dihydropyrimido[4,5-d]pyrimidin-2(1H)-one as an orange colored gum. [Mass spectrum (ESI) MH+= 581].

The 3-(2,6-dichlorophenyl)-1-[2-cyclohexen-1(RS)-yl]-7-methanesulfonyl-3,4-dihydropyrimido[4,5-d]pyrimidin-2(1H)-one used as the starting material was prepared as follows:

A solution, cooled in ice, of 200 mg (0.54 mmol) of 3-(2,6-dichlorophenyl)-7-methanesulfonyl-3,4-dihydropyrimido[4,5-d]pyrimidin-2(1H)-one in 12 ml of dimethylformamide was treated with 22 mg (0.54 mmol) of sodium hydride (60% w/w). After 30 minutes the mixture was treated with 0.07 ml (0.6 mmol) of 3-bromocyclohexene and then heated at reflux for 4 hours. The mixture was evaporated and 30 ml of dichloromethane and 30 ml of water were added to the residue. The phases were separated and the organic phase was washed with 30 ml of water, dried over magnesium sulfate, filtered and evaporated to give 70 mg (29%) 3-(2,6-dichlorophenyl)-1-[2-cyclohexen-1(RS)-yl]-7-methanesulfonyl-3,4-dihydropyrimido[4,5-d]pyrimidin-2(1H)-one as a brown oil. [Mass spectrum (ESI) MH+=453].

Example 43

A mixture of 200 mg (0.5 mmol) of 3-(2-bromophenyl)-7-methanesulfonyl-3,4-dihydro-1-methylpyrimido[4,5-d]pyrimidin-2(1H)-one and 208 mg (1 mmol) of 4-[2-(diethylamino)ethoxy]aniline was heated at 180° C. for 30 minutes and then cooled. The residue was subjected to column chromatography on silica gel using dichloromethane/methanol/acetic acid/water (240:24:3:2) for the elution. Product-containing fractions were combined and evaporated and the residue was evaporated with toluene. The residue was then dissolved in 40 ml of dichloromethane, washed with 40 ml of saturated aqueous sodium bicarbonate solution, dried over magnesium sulfate, filtered and evaporated to give 22 mg (8%) of 3-(2-bromophenyl)-7-[4-[2-(diethylamino)ethoxy]anilino]-3,4-dihydro-1-methylpyrimido[4,5-d]pyrimidin-2(1H)-one as a cream colored solid of melting point 144° C.

The 3-(2-bromophenyl)-7-methanesulfonyl-3,4-dihydro-1-methylpyrimido[4,5-d]pyrimidin-2(1H)-one used as the starting material was prepared in a manner analogous to that described in Example 35 for 3-(2,6-difluorophenyl)-7-methanesulfonyl-3,4-dihydro-1-methylpyrimido[4,5-d]pyrimidin-2(1H)-one using 2-bromoaniline in place of 2,6-difluoroaniline.

Example 44

A mixture of 200 mg (0.52 mmol) of 3-(2,5-dichlorophenyl)-7-methanesulfonyl-3,4-dihydro-1-methylpyrimido[4,5-d]pyrimidin-2(1H)-one and 218 mg (1.04 mmol) of 4-(2-(diethylamino)ethoxy)aniline was heated at 180° C. for 30 minutes and then cooled. The residue was subjected to column chromatography on silica gel eluted with dichloromethane/methanol/acetic acid/water in a ratio of 240:24:3:2. Product containing fractions were combined, evaporated and the residue re-evaporated with toluene. The residue was dissolved in dichloromethane (40 ml), washed with saturated aqueous sodium bicarbonate (40 ml), dried over magnesium sulfate, filtered and evaporated to give 15 mg (6%) of 3-(2,5-dichlorophenyl)-7-[4-[2-(diethylamino)ethoxy]anilino]-3,4-dihydro-1-methylpyrimido[4,5-d]pyrimidin-2(1H)-one as a white solid of melting point 138° C. [Mass spectrum (ESI) MH+=514].

The 3-(2,5-dichlorophenyl)-7-methanesulfonyl-3,4-dihydro-1-methylpyrimido[4,5-d]pyrimidin-2(1H)-one used as the starting material was prepared in a manner analogous to that described in Example 35 for 3-(2,6-difluorophenyl)-7-methanesulfonyl-3,4-dihydro-1-methylpyrimido[4,5-d]pyrimidin-2(1H)-one using 2,5-dichloroaniline in place of 2,6-difluoroaniline.

Example 45

A mixture of 200 mg (0.5 mmol) of 3-(3-bromophenyl)-7-methanesulfonyl-3,4-dihydro-1-methylpyrimido[4,5-d]pyrimidin-2(1H)-one and 300 mg (1.4 mmol) of 4-[2-(diethylamino)ethoxy]aniline was heated at 180° C. for 35 minutes and then cooled. The residue was subjected to column chromatography on silica gel using dichloromethane/methanol/acetic acid/water (240:24:3:2) for the elution. Product-containing fractions were combined, and evaporated and the residue was evaporated with toluene. The residue was then dissolved in 40 ml of dichloromethane, washed with 40 ml of saturated aqueous sodium bicarbonate solution, dried over magnesium sulfate, filtered and evaporated to give 30 mg (11%) of 3-(3-bromophenyl)-7-[4-[2-(diethylamino)ethoxy]anilino]-3,4-dihydro-1-methylpyrimido[4,5-d]pyrimidin-2(1H)-one as an off-white solid of melting point 150° C.

The 3-(3-bromophenyl)-7-methanesulfonyl-3,4-dihydro-1-methylpyrimido[4,5-d]pyrimidin-2(1H)-one used as the starting material was prepared in a manner analogous to that described in Example 35 for 3-(2,6-difluorophenyl)-7-methanesulfonyl-3,4-dihydro-1-methylpyrimido[4,5-d]pyrimidin-2(1H)-one using 3-bromoaniline in place of 2,6-difluoroaniline.

Example 46

A mixture of 380 mg (1.1 mmol) of 3-(2-methoxyphenyl)-7-methanesulfonyl-3,4-dihydro-1-methylpyrimido[4,5-d]pyrimidin-2(1H)-one and 3 ml of aniline was heated at 180° C. for 45 minutes, then cooled and partitioned between 30 ml of dichloromethane and 30 ml of 2M hydrochloric acid. The organic phase was dried over magnesium sulfate, filtered and evaporated. The residue was subjected to column chromatography on silica gel using dichloromethane/methanol for the elution in a gradient from a ratio of 99:1 to a ratio of 20:1. Product-containing fractions were combined and evaporated to 7-anilino-3,4-dihydro-3-(2-methoxyphenyl)-1-methylpyrimido[4,5-d]pyrimidin-2(1H)-one as an off-white solid of melting point 225° C.

The 3-(2-methoxyphenyl)-7-methanesulfonyl-3,4-dihydro-1-methylpyrimido[4,5-d]pyrimidin-2(1H)-one used as the starting material was prepared in a manner analogous to that described in Example 35 for 3-(2,6-difluorophenyl)-7-methanesulfonyl-3,4-dihydro-1-methylpyrimido[4,5-d]pyrimidin-2(1H)-one using 2-methoxyaniline in place of 2,6-difluoroaniline.

Example 47

A solution of 50 mg (0.14 mmol) of 3-(2-methoxyphenyl)-7-anilino-3,4-dihydro-1-methylpyrimido[4,5-d]pyrimidin-2(1H)-one in 15 ml of 48% aqueous hydrobromic acid was heated at reflux for 1 hour. The mixture was cooled and evaporated and the residue was triturated in hexane. The resultant solid was filtered off and dried to give 40 mg (82%) of 7-anilino-3,4-dihydro-3-(2-hydroxyphenyl)-1-methylpyrimido[4,5-d]pyrimidin-2(1H)-one as an off-white solid of melting point 192° C.

Example 48

A mixture of 200 mg (0.55 mmol) of 3-(4-methoxybenzyl)-7-methanesulfonyl-3,4-dihydro-1-methylpyrimido[4,5-d]pyrimidin-2(1H)-one and 300 mg (1.4 mmol) of 4-[2-(diethylamino)ethoxy]aniline was heated at 180° C. for 20 minutes and then cooled. The residue was subjected to column chromatography on silica gel using dichloromethane/methanol/acetic acid/water (240:24:3:2) for the elution. Product-containing fractions were combined, evaporated and the residue was evaporated with toluene. The residue was then dissolved in 40 ml of dichloromethane, washed with 40 ml of saturated aqueous sodium bicarbonate solution, dried over magnesium sulfate, filtered and evaporated. The residue was triturated in hexane, filtered off and dried to give 20 mg (7%) of 7-[4-[2-(diethylamino)ethoxy]anilino]-3,4-dihydro-3-(4-methoxybenzyl)-1-methylpyrimido[4,5-d]pyrimidin-2(1H)-one as a white solid of melting point 112° C.

The 3-(4-methoxybenzyl)-7-methanesulfonyl-3,4-dihydro-1-methylpyrimido[4,5-d]pyrimidin-2(1H)-one used as the starting material was prepared in a manner analogous to that described in Example 4 for 3-cyclohexyl-7-methanesulfonyl-3,4-dihydro-1-methylpyrimido[4,5-d]pyrimidin-2(1H)-one using 4 using 4-methoxybenzylamine in place of cyclohexylamine.

Example 49

A mixture of 300 mg (0.6 mmol) of 3-(2-bromophenyl)-7-methanesulfonyl -3,4-dihydro-1-[3-(2-hydroxyethyl)phenyl]pyrimido[4,5-d]pyrimidin-2(1H)-one and 1.5 ml of 4-methoxybenzylamine was heated at 100° C. for 1 hour. The mixture was cooled and partitioned between 30 ml of dichloromethane and 30 ml of 2M aqueous hydrochloric acid. The organic phase was dried over magnesium sulfate, filtered and evaporated. The residue was dissolved in 10 ml of trifluoroacetic acid and then heated at reflux for 3 hours. The mixture was cooled and evaporated and the residue was partitioned between 25 ml of ethyl acetate and 25 ml of saturated sodium bicarbonate solution. The organic phase was dried over magnesium sulfate, filtered and evaporated and the residue was subjected to column chromatography on silica gel using ethyl acetate for the elution. Product-containing fractions were combined and evaporated to give 105 mg (40%) of 7-amino-3-(2-bromophenyl)-3,4-dihydro-1-[3-(2-hydroxyethyl)phenyl]pyrimido[4,5-d]pyrimidin-2(1H)-one as a white solid of melting point 154° C.

The 3-(2-bromophenyl)-7-methanesulfonyl-3,4-dihydro-1-(3-(2-hydroxyethyl)phenyl)pyrimido[4,5-d]pyrimidin-2(1H)-one used as the starting material was prepared as follows:

a) A solution of 2.5 g (8.65 mmol) of 5-formyl-4-[3-(2-hydroxyethyl)phenyl]amino-2-methylthiopyrimidine in 120 ml of toluene was treated with 1.5 g (9.3 mmol) of 2-bromoaniline and 100 mg (0.5 mmol) of 4-toluenesulfonic acid monohydrate and then heated at reflux with azeotropic removal of water for 1 hour. The cooled mixture was evaporated and the residue was dissolved in 4 ml of tetrahydrofuran. The solution obtained was added dropwise to a solution of 9 ml (9 mmol) of lithium aluminium hydride (as a 1M solution in tetrahydrofuran) in 40 ml of tetrahydrofuran. After 1 hour the reaction was quenched by the cautious dropwise addition of 0.35 ml of water, 0.35 ml of 2M aqueous sodium hydroxide and 1 ml of water. The resulting suspension was filtered through a filter aid and the filtrate was evaporated. The residue was partitioned between 150 ml of ethyl acetate and 50 ml of saturated aqueous sodium bicarbonate solution. The organic phase was dried over magnesium sulfate, filtered and evaporated to give 3.5 g (91%) of 5-(2-bromoanilino)methyl-4-[3-( 2-hydroxyethyl)phenyl]amino-2-methylthiopyrimidine as an orange colored gum. [Mass spectrum (ESI) MH+=444].

b) A solution of 3.5 g (7.9 mmol) of 5-(2-bromoanilino)methyl-4-[3-(2-hydroxyethyl)phenyl]amino-2-methylthiopyrimidine in 100 ml of dichloromethane was treated with 3.3 g (39 mmol) of dihydropyran and 15 mg (0.08 mmol) of 4-toluenesulfonic acid monohydrate. After 18 hours the mixture was treated with 100 mg (0.4 mmol) of pyridinium 4-toluenesulfonate. After a further 3 days 100 ml of ether and 100 ml of 50% saturated brine were added. The organic phase was dried over magnesium sulfate, filtered and evaporated to give 2.6 g (62%) of 5-(2-bromoanilino) methyl-4-[3-(2-(tetrahydropyran-2-yl)oxyethyl] phenylamino-2-methylthiopyrimidine as a yellow oil. [Mass spectrum (ESI) MH$^+$=529].

c) A solution of 2.6 g (4.9 mmol) of 5-(2-bromoanilino) methyl-4-[3-(2-(tetrahydropyran-2-yl)oxyethyl] phenylamino-2-methylthiopyrimidine in 60 ml of tetrahydrofuran was treated with 2 ml (14.4 mmol) of triethylamine and the mixture was added dropwise to a solution, cooled in ice, of 3 ml of phosgene (20% in toluene) in 20 ml of tetrahydrofuran. After 1 hour 50 ml of saturated aqueous ammonium chloride were added. The organic phase was separated, dried over magnesium sulfate, filtered and evaporated. The residue was dissolved in 100 ml of methanol and 20 ml of saturated hydrochloric acid in ethyl acetate were added. After 10 minutes the mixture was evaporated to give 1.8 g (78%) of 3-(2-bromophenyl)-7-methylthio-3,4-dihydro-1-(3-(2-hydroxyethyl)phenyl)pyrimido[4,5-d]pyrimidin-2(1H)-one as an off-white solid. [Mass spectrum (ESI) MH$^+$=471].

d) A solution of 1.4 g (3 mmol) of 3-(2-bromophenyl)-7-methylthio-3,4-dihydro-1-(3-(2-hydroxyethyl)phenyl) pyrimido[4,5-d]pyrimidin-2(1H)-one in 60 ml of dichloromethane was treated with 2 g (6 mmol) of 3-chloroperbenzoic acid (50% w/w water). After 18 hours 40 ml of saturated aqueous sodium bicarbonate solution were added. The organic phase was dried over magnesium sulfate, filtered and evaporated to give 1.45 g (100%) of 3-(2-bromophenyl)-7-methanesulfonyl-3,4-dihydro-1-[3-(2-hydroxyethyl)phenyl]pyrimido[4,5-d]pyrimidin-2(1H)-one as a white solid. [Mass spectrum (ESI) MH$^+$=503].

Example 50

A solution of 200 mg (0.31 mmol) of 7-anilino-3-(2-bromophenyl)-3,4-dihydro-1-[3-(2-phthalimidoethyl) phenyl]pyrimido[4,5-d]pyrimidin-2(1H)-one in 20 ml of ethanol was treated with 0.3 ml of hydrazine hydrate. After 20 hours the mixture was evaporated and the product purified by column chromatography on silica gel using dichloromethane/methanol/acetic acid/water (240:24:3:2) for the elution. Product-containing fractions were combined, evaporated and the residue evaporated with toluene. The residue was then dissolved in 50 ml of dichloromethane, washed with 50 ml of saturated aqueous sodium bicarbonate solution, dried over magnesium sulfate, filtered and evaporated to give 45 mg (28%) of 1-[3-(2-aminoethyl)phenyl]-7-anilino-3-(2-bromophenyl)-3,4-dihydropyrimido[4,5-d] pyrimidin-2(1H)-one as a white solid of melting point 130° C.

The 7-anilino-3-(2-bromophenyl)-3,4-dihydro-1-[3-(2-phthalimidoethyl)phenyl]pyrimido[4,5-d]pyrimidin-2(1H)-one used as starting material was prepared in a method analogous to that described in Example 37 for 7-anilino-3-(2,6-dichlorophenyl)-3,4-dihydro-1-[3-(2-phthalimidoethyl) phenyl]pyrimido[4,5-d]pyrimidin-2(1H)-one using 2-bromoaniline in place of 2,6-dichloroaniline.

Example 51

A solution of 500 mg (0.86 mmol) of 7-anilino-3,4-dihydro-3-(2,6-dimethylphenyl)-1-[3-(2-phthalimidoethyl) phenyl]pyrimido[4,5-d]pyrimidin-2(1H)-one in 30 ml of ethanol was treated with 0.8 ml of hydrazine hydrate. After 18 hours the mixture was evaporated and the product purified by column chromatography on silica gel using dichloromethane/methanol/acetic acid/water (240:24:3:2) for the elution. Product-containing fractions were combined, evaporated and the residue evaporated with toluene. The residue was then dissolved in 50 ml of dichloromethane, washed with 50 ml of saturated aqueous sodium bicarbonate solution, dried over magnesium sulfate, filtered and evaporated. Trituration of the residue with hexane followed by filtration afforded 10 mg (3%) of 1-[3-(2-aminoethyl) phenyl]-7-anilino-3,4-dihydro-3-(2,6-dimethylphenyl)-pyrimido[4,5-d]pyrimidin-2(1H)-one as a white solid of melting point 128° C.

The 7-anilino-3,4-dihydro-3-(2,6-dimethylphenyl)-1-[3-(2-phthalimidoethyl)phenyl]pyrimido[4,5-d]pyrimidin-2 (1H)-one used as starting material was prepared in a method analogous to that described in Example 37 for 7-anilino-3-(2,6-dichlorophenyl)-3,4-dihydro-1-[3-(2-phthalimidoethyl) phenyl]pyrimido[4,5-d]pyrimidin-2(1H)-one using 2,6-dimethylaniline in place of 2,6-dichloroaniline.

Example 52

A solution of 155 mg (0.23 mmol) of 7-anilino-3-(2-chloro-4-trifluoromethylphenyl)-3,4-dihydro-1-[3-(2-phthalimidoethyl)phenyl]pyrimido[4,5-d]pyrimidin-2(1H)-one in 20 ml of ethanol was treated with 0.3 ml of hydrazine hydrate. After 18 hours the mixture was evaporated and the product purified by column chromatography on silica gel using dichloromethane/methanol/acetic acid/water (240:24:3:2) for the elution. Product-containing fractions were combined, evaporated and the residue evaporated with toluene. The residue was then dissolved in 40 ml of dichloromethane, washed with 40 ml of saturated aqueous sodium bicarbonate solution, dried over magnesium sulfate, filtered and evaporated. Trituration of the residue with hexane followed by filtration afforded 40 mg (32%) of 1-[3-(2-aminoethyl)phenyl]-7-anilino-3-(2-chloro-4-trifluoromethylphenyl)-3,4-dihydropyrimido[4,5-d] pyrimidin-2(1H)-one as a white solid of melting point 102° C.

The 7-anilino-3-(2-chloro-4-trifluoromethylphenyl)-3,4-dihydro-1-[3-(2-phthalimidoethyl)phenyl]pyrimido[4,5-d] pyrimidin-2(1H)-one used as starting material was prepared in a method analogous to that described in Example 37 for 7-anilino-3-(2,6-dichlorophenyl)-3,4-dihydro-1-[3-(2-phthalimidoethyl)phenyl]pyrimido[4,5-d]pyrimidin-2(1H)-one using 2-chloro-4-trifluoromethylaniline in place of 2,6-dichloroaniline.

Example 53

A solution of 1.2 g (1.7 mmol) of 7-anilino-1-[3-(2-(tert-butyldiphenyl-silyloxy)ethyl)phenyl]-3-(2-chloro-6-methylphenyl)-3,4-dihydropyrimido[4,5-d]pyrimidin-2 (1H)-one in 30 ml of tetrahydrofuran was treated with 2.25 ml (2.25 mmol) of tetrabutylammonium fluoride (1M in tetrahydrofuran). The mixture was heated at reflux for 5 hours, cooled and evaporated. The residue was partitioned between 50 ml of ethyl acetate and 50 ml of 2M aqueous hydrochloric acid. The organic phase was washed with 40 ml of water, dried over magnesium sulfate, filtered and evaporated. The residue was purified by flash chromatography on silica gel using a gradient elution from dichloromethane/ methanol 100:1 to dichloromethane/methanol 100:5. Product-containing fractions were evaporated to give 350 mg (42%) of 7-anilino-3-(2-chloro-6-methylphenyl)-3,4-dihydro-1-[3-(2-hydroxyethyl)phenyl]pyrimido[4,5-d] pyrimidin-2(1H)-one as a gum. [Mass spectrum (ESI) MH$^+$=486].

The 7-anilino-1-[3-(2-(tert-butyldiphenylsilyloxy)ethyl) phenyl]-3-(2-chloro-6-methylphenyl)-3,4-dihydropyrimido

[4,5-d]pyrimidin-2(1H)-one used as starting material was prepared as follows:

a) A solution of 3.4 g (11.7 mmol) of 5-formyl-4-(3-(2-hydroxyethyl)phenylamino)-2-methylthiopyrimidine of Example 37(e) in 50 ml of dimethylformamide was treated with 3.9 g (14 mmol) of tert-butyldiphenylchlorosilane, 2.4 g (35 mmol) of imidazole and 50 mg (0.4 mmol) of 4-(dimethylamino)pyridine. The mixture was stirred for 18 hours and then evaporated. The residue was partitioned between 150 ml of ethyl acetate and 100 ml of 2M aqueous hydrochloric acid. The organic phase was washed with a further 100 ml of 2M aqueous hydrochloric acid, dried over magnesium sulfate, filtered and evaporated to yield 6.2 g (100%) of 4-(3-(2-(tert-butyldiphenylsilyloxy)ethyl)phenylamino)-5-formyl-2-methylthiopyrimidine as a white solid. [Mass spectrum (ESI) MH$^+$=528].

b) A mixture of 2.6 g (5 mmol) of 4-(3-(2-(tert-butyldiphenylsilyloxy)ethyl)phenylamino)-5-formyl-2-methylthiopyrimidine and 0.63 ml (722 mg, 5.1 mmol) of 2-chloro-6-methylaniline in 80 ml of toluene was treated with 170 mg (0.9 mmol) of 4-toluenesulfonic acid monohydrate and then heated at reflux with azeotropic removal of water for 2 hours. The mixture was cooled and evaporated. The residue was dissolved in 20 ml of tetrahydrofuran and added dropwise to a solution of 5 ml (5 mmol) of lithium aluminium hydride (1M solution in tetrahydrofuran) in a further 30 ml of tetrahydrofuran. After stirring for 1 hour the reaction was quenched by the cautious dropwise addition of 1.5 ml of water, 2 ml of 2M aqueous sodium hydroxide and 2.5 ml of water. The mixture was filtered through a filter aid and the filtrate evaporated to give 3.3 g (100%) of 4-[3-(2-(tert-butyldiphenylsilyloxy)ethyl)phenyl]amino-5-(2-chloro-6-methylanilino)methyl-2-methylthiopyrimidine as a yellow oil which was used without further purification. [Mass spectrum (ESI) MH$^+$=653].

c) A solution of 3.3 g (5 mmol) of 4-[3-(2-(tert-butyldiphenylsilyloxy)ethyl)phenyl]amino-5-(2-chloro-6-methylanilino)methyl-2-methylthiopyrimidine in 50 ml of tetrahydrofuran was treated with 1.4 ml (10 mmol) of triethylamine and the resulting mixture was added dropwise to a solution of 5 ml (9.6 mmol) of phosgene (20% in toluene) in 30 ml of tetrahydrofuran. The mixture was stirred at room temperature for 24 hours and then heated at reflux for a further 18 hours. The mixture was cooled and evaporated. The mixture was partitioned between 40 ml of dichloromethane and 40 ml of saturated aqueous sodium bicarbonate. The organic phase was dried over magnesium sulfate, filtered and evaporated to give 1.58 g (47%) of 1-[3-(2-(tert-butyldiphenylsilyloxy)ethyl)phenyl]-3-(2-chloro-6-methylphenyl)-3,4-dihydro-7-methylthio-pyrimido[4,5-d]pyrimidin-2(1H)-one as a yellow solid. [Mass spectrum (ESI) MH$^+$=679].

d) A solution of 1.58 g (2.3 mmol) of 1-[3-(2-(tert-butyldiphenylsilyloxy)ethyl)phenyl]-3-(2-chloro-6-methylphenyl)-3,4-dihydro-7-methylthio-pyrimido[4,5-d]pyrimidin-2(1H)-one in 40 ml of dichloromethane was treated with 1.6 g (4.3 mmol) of 3-chloroperbenzoic acid (50% w/w water). After 18 hours 40 ml of saturated aqueous sodium bicarbonate was added. The organic phase was dried over magnesium sulfate, filtered and evaporated. The product was recrystallized from ethanol to yield 1.1 g (67%) of 1-[3-(2-(tert-butyldiphenylsilyloxy)ethyl)phenyl]-3-(2-chloro-6-methylphenyl)-3,4-dihydro-7-methanesulfonyl-pyrimido[4,5-d]pyrimidin-2(1H)-one as a white solid. [Mass spectrum (ESI) MH$^+$=711].

e) A mixture of 1.1 g (1.5 mmol) of 1-[3-(2-(tert-butyldiphenylsilyloxy)ethyl)phenyl]-3-(2-chloro-6-methylphenyl)-3,4-dihydro-7-methanesulfonyl-pyrimido[4,5-d]pyrimidin-2(1H)-one and 3 ml of aniline was heated at 180° C. for 20 minutes. The mixture was cooled and added to 50 ml of 2M aqueous hydrochloric acid. The resulting suspension was filtered and the solid washed with water and dried to give 1.2 g (100%) of 1-[3-(2-(tert-butyldiphenylsilyloxy)ethyl)phenyl]-7-anilino-3-(2-chloro-6-methylphenyl)-3,4-dihydropyrimido[4,5-d]pyrimidin-2(1H)-one as a tan solid. [Mass spectrum (ESI) MH$^+$=724].

Example 54

A solution of 250 mg (0.4 mmol) of 7-anilino-3-(2-chloro-6-methylphenyl)-3,4-dihydro-1-[3-(2-phthalimidoethyl)phenyl]pyrimido[4,5-d]pyrimidin-2(1H)-one in 10 ml of ethanol was treated with 0.5 ml of hydrazine hydrate. After 18 hours the mixture was evaporated and the product purified by column chromatography on silica gel using dichloromethane/methanol/acetic acid/water (240:24:3:2) for the elution. Product-containing fractions were combined, evaporated and the residue evaporated with toluene. The residue was then dissolved in 40 ml of dichloromethane, washed with 40 ml of saturated aqueous sodium bicarbonate solution, dried over magnesium sulfate, filtered and evaporated. Trituration of the residue with hexane followed by filtration afforded 30 mg (15%) of 1-[3-(2-aminoethyl)phenyl]-7-anilino-3-(2-chloro-6-methylphenyl)-3,4-dihydropyrimido[4,5-d]pyrimidin-2(1H)-one as a white solid of melting point 192° C.

The 7-anilino-3-(2-chloro-6-methylphenyl)-3,4-dihydro-1-[3-(2-phthalimidoethyl)phenyl]pyrimido[4,5-d]pyrimidin-2(1H)-one used as starting material was prepared as follows:

a) A solution of 200 mg (0.41 mmol) of 7-anilino-3-(2-chloro-6-methylphenyl)-3,4-dihydro-1-[3-(2-hydroxyethyl)phenyl]pyrimido[4,5-d]pyrimidin-2(1H)-one (prepared in Example 53) in 15 ml of dichloromethane was treated with 0.12 ml (0.82 mmol) of triethylamine and 87 mg (0.5 mmol) of methanesulfonic anhydride. After 18 hours the mixture was washed with 30 ml of saturated aqueous sodium bicarbonate, dried over magnesium sulfate, filtered and evaporated to yield 233 mg (100%) of 7-anilino-3-(2-chloro-6-methylphenyl)-3,4-dihydro-1-[3-(2-methanesulfonyloxyethyl)phenyl]pyrimido[4,5-d]pyrimidin-2(1H)-one as a gum. [Mass spectrum (ESI) MH$^+$=564].

b) A solution of 233 mg (0.41 mmol) of 7-anilino-3-(2-chloro-6-methylphenyl)-3,4-dihydro-1-[3-(2-methanesulfonyloxyethyl)phenyl]pyrimido[4,5-d]pyrimidin-2(1H)-one in 10 ml of dimethylformamide was treated with 100 mg (0.54 mmol) of potassium phthalimide and the mixture heated at 90° C. for 3 hours. The mixture was cooled and evaporated. The residue was partitioned between 50 ml of ethyl acetate and 50 ml of water. The organic phase was dried over magnesium sulfate, filtered and evaporated to give 250 mg (99%) of 7-anilino-3-(2-chloro-6-methylphenyl)-3,4-dihydro-1-[3-(2-phthalimidoethyl)phenyl]-pyrimido[4,5-d]pyrimidin-2(1H)-one as a white solid. [Mass spectrum (ESI) MH$^+$=615].

Example 55

A solution of 90 mg (0.14 mmol) of 7-anilino-3-(2,5-dichlorophenyl)-3,4-dihydro-1-[3-(2-phthalimidoethyl)phenyl]pyrimido[4,5-d]pyrimidin-2(1H)-one and 0.07 ml of hydrazine hydrate in 15 ml of methanol was stirred at room temperature under an atmosphere of nitrogen for 18 hours. The reaction was evaporated and the residue purified by flash column chromatography on silica gel, eluting with dichloromethane/methanol/acetic acid/water (240:24:3:2). Product containing fractions were combined and evaporated and the residue re-evaporated with toluene. The residue was then dissolved in 20 ml of dichloromethane, washed with 20 ml of saturated aqueous sodium bicarbonate, dried over magnesium sulfate, filtered and evaporated to give 37 mg (52%) of 1-[3-(2-aminoethyl)phenyl]-7-anilino-3-(2,5-dichlorophenyl)-3,4-dihydropyrimido[4,5-d]pyrimidin-2 (1H)-one as a white solid of melting point 120–123° C. [Mass spectrum (ESI) MH$^+$=505].

The 7-anilino-3-(2,5-dichlorophenyl)-3,4-dihydro-1-[3-(2-phthalimidoethyl)phenyl]pyrimido[4,5-d]pyrimidin-2 (1H)-one used as the starting material was prepared from 7-anilino-3-(2,5-dichlorophenyl)-3,4-dihydro-1-[3-(2-hydroxyethyl)phenyl]pyrimido[4,5-d]pyrimidin-2(1H)-one (prepared in a manner analogous to that of Example 53 using 2,5-dichloroaniline in place of 2-chloro-6-methylaniline) in a method analogous to that described in Example 54.

Example 56

200 mg (0.40 mmol) of 3-(2-bromophenyl)-3,4-dihydro-1-[3-(2-hydroxyethyl)phenyl]-7-methanesulfonyl-pyrimido [4,5-d]pyrimidin-2(1H)-one was treated with 250 mg (1.2 mmol) of 4-[2-(diethylamino)ethoxy]aniline and the mixture heated at 180° C. for 40 minutes. The mixture was cooled and the product purified by column chromatography on silica gel using dichloromethane/methanol/acetic acid/water (240:24:3:2) for the elution. Product-containing fractions were combined, evaporated and the residue evaporated with toluene. The residue was then dissolved in 40 ml of dichloromethane, washed with 40 ml of saturated aqueous sodium bicarbonate solution, dried over magnesium sulfate, filtered and evaporated to give 45 mg (18%) of 3-(2-bromophenyl)-7-[4-[2-(diethylamino)ethoxy]anilino]-3,4-dihydro-1-[3-(2-hydroxyethyl)phenyl]pyrimido[4,5-d] pyrimidin-2(1H)-one as a white solid of melting point 98° C.

The 3-(2-bromophenyl)-3,4-dihydro-1-[3-(2-hydroxyethyl)phenyl]-7-methanesulfonyl-pyrimido[4,5-d] pyrimidin-2(1H)-one used as starting material was prepared as follows:

a) A solution of 3.5 g (7.9 mmol) of 5-(2-bromoanilino) methyl-4-[3-(2-hydroxyethyl)phenyl]amino-2-methylthiopyrimidine (prepared in a method analogous to that for 5-(2,6-dichloroanilino)methyl-4-[3-(2-hydroxyethyl)phenyl]amino-2-methylthiopyrimidine of Example 37(f) using 2-bromoaniline in place of 2,6-dichloroaniline) in 100 ml of dichloromethane was treated with 3.3 g (39 mmol) of 2,3-dihydropyran and 15 mg (0.08 mmol) of toluenesulfonic acid monohydrate and the mixture stirred at room temperature for 3 days. Subsequently 100 ml of diethyl ether and 100 ml of brine were added. The mixture was separated and the organic phase dried over magnesium sulfate, filtered and evaporated. Flash chromatography on silica gel using diethyl ether and hexane in a ratio of 1:1 as eluent afforded 2.6 g of 5-(2-bromoanilino)methyl-4-[3-(2-(tetrahydropyranyloxy)ethyl)phenyl]amino-2-methylthiopyrimidine as a yellow oil. [Mass spectrum (ESI) MH$^+$=529].

b) A solution of 2.6 g (4.9 mmol) of 5-(2-bromoanilino) methyl-4-[3-(2-(tetrahydropyranyloxy)ethyl)phenyl]amino-2-methylthiopyrimidine in 40 ml of tetrahydrofuran was treated with 2 ml (14.4 mmol) of triethylamine and the resulting solution added dropwise to an ice-cooled solution of phosgene (3 ml of a 20% solution in toluene, 5.8 mmol) in 40 ml of tetrahydrofuran. After 1 hour 50 ml of a saturated solution of ammonium chloride was added. The mixture was separated and the organic phase dried over magnesium sulfate and filtered. To the solution was added 20 ml of a saturated solution of hydrogen chloride in ethyl acetate. After 10 minutes the solution was evaporated to afford 1.8 g (78%) of 3-(2-bromophenyl)-3,4-dihydro-1-[3-(2-hydroxyethyl)phenyl]-7-methylthio-pyrimido[4,5-d] pyrimidin-2(1H)-one as a white solid. [Mass spectrum (ESI) MH$^+$=471].

c) A solution of 1.4 g (3 mmol) of 3-(2-bromophenyl)-3,4-dihydro-1-[3-(2-hydroxyethyl)phenyl]-7-methylthio-pyrimido[4,5-d]pyrimidin-2(1H)-one in 60 ml of dichloromethane was treated with 2 g (6 mmol) of 3-chloroperbenzoic acid (50% w/w water) and the mixture stirred for 18 hours. The mixture was washed with 50 ml of saturated aqueous sodium bicarbonate, dried over magnesium sulfate, filtered and evaporated to give 1.45 g (100%) of 3-(2-bromophenyl)-3,4-dihydro-1-[3-(2-hydroxyethyl) phenyl]-7-methanesulfonyl-pyrimido[4,5-d]pyrimidin-2 (1H)-one as a white solid. [Mass spectrum (ESI) MH$^+$=503].

Example 57

A solution of 1.3 g (1.7 mmol) of 7-anilino-3-(2-bromophenyl)-3,4-dihydro-1-[3-((1,1-dimethyl-2-(tert-butyldiphenylsilyloxy))ethyl)phenyl]pyrimido[4,5-d] pyrimidin-2(1H)-one in 30 ml of tetrahydrofuran was treated with 2.1 ml (2.1 mmol) of tetrabutylammonium fluoride (1M in tetrahydrofuran). The mixture was heated at reflux for 5 hours, cooled and evaporated. The residue was partitioned between 50 ml of ethyl acetate and 50 ml of 2M aqueous hydrochloric acid. The organic phase was washed with 40 ml of water, dried over magnesium sulfate, filtered and evaporated. The residue was purified by flash chromatography on silica gel using a gradient elution from dichloromethane/methanol 100:1 to dichloromethane/methanol 100:5. Product-containing fractions were evaporated and the residue recrystallized from ethyl acetate to give 500 mg (54%) of 7-anilino-3-(2-bromophenyl)-3,4-dihydro-1-[3-((1,1-dimethyl-2-hydroxy)ethyl)phenyl]pyrimido[4,5-d] pyrimidin-2(1H)-one as a cream-colored solid of melting point 178° C. [Mass spectrum (ESI) MH$^+$=545].

The 7-anilino-3-(2-bromophenyl)-3,4-dihydro-1-[3-((1,1-dimethyl-2-(tert-butyldiphenylsilyloxy))ethyl)phenyl] pyrimido[4,5-d]pyrimidin-2(1H)-one used as starting material was prepared in a method analogous to 7-anilino-3-(2-chloro-6-methylphenyl)-3,4-dihydro-1-[3-(2-(tert-butyldiphenylsilyloxy)ethyl)phenyl]pyrimido[4,5-d] pyrimidin-2(1H)-one of Example 53 starting from 5-formyl-4-(3-((1,1-dimethyl-2-hydroxy)ethyl)phenylamino)-2-methylthiopyrimidine in place of 5-formyl-4-(3-(2-hydroxyethyl)phenylamino)-2-methylthiopyrimidine and 2-bromoaniline in place of 2-chloro-6-methylaniline.

5-Formyl-4-(3-((1,1-dimethyl-2-hydroxy)ethyl) phenylamino)-2-methylthiopyrimidine was prepared in a method analogous to 5-formyl-4-(3-( 2-hydroxyethyl) phenylamino)-2-methylthiopyrimidine of Example 37 using ethyl (2,2-dimethyl-2-(3-nitrophenyl))acetate in place of ethyl 3-nitrophenylacetate.

Ethyl (2,2-dimethyl-2-(3-nitrophenyl))acetate was prepared as follows:

A solution of 5 g (24 mmol) of ethyl 3-nitrophenylacetate in 20 ml tetrahydrofuran was added dropwise to a suspension of 2.88 g (72 mmol) of sodium hydride(60% w/w) in 80 ml of tetrahydrofuran. After 30 minutes, 3.6 ml (57 mmol) of iodomethane was added dropwise and the resulting brown suspension stirred for 1 hour. 50 ml of saturated aqueous ammonium chloride was cautiously added followed by 50 ml of ethyl acetate. The mixture was separated and the organic phase washed with 50 ml of brine, dried over magnesium sulfate, filtered and evaporated to afford 5.5 g (97%) of ethyl (2,2-dimethyl-2-(3-nitrophenyl))acetate as a brown oil. [Mass spectrum (ESI) MH$^+$=238].

Example 58

A solution of 250 mg (0.37 mmol) of 7-anilino-3-(2-bromophenyl)-3,4-dihydro-1-[3-((1,1-dimethyl-2-phthalimido)ethyl)phenyl]pyrimido[4,5-d]pyrimidin-2(1H)-one in 10 ml of ethanol was treated with 0.5 ml of hydrazine hydrate. After 18 hours the mixture was evaporated and the product purified by column chromatography on silica gel using dichloromethane/methanol/acetic acid/water (240:24:3:2) for the elution. Product-containing fractions were combined, evaporated and the residue evaporated with toluene. The residue was then dissolved in 50 ml of dichloromethane, washed with 50 ml of saturated aqueous sodium bicarbonate solution, dried over magnesium sulfate, filtered and evaporated. The residue was triturated in hexane to give 40 mg (20%) of 1-[3-((2-amino-1,1-dimethyl)ethyl)phenyl]-7-anilino-3-(2-bromophenyl)-3,4-dihydropyrimido[4,5-d]pyrimidin-2(1H)-one as a white solid of melting point 188° C.

The 7-anilino-3-(2-bromophenyl)-3,4-dihydro-1-[3-((1,1-dimethyl-2-phthalimido)ethyl)phenyl]pyrimido[4,5-d]pyrimidin-2(1H)-one used as starting material was prepared from 7-anilino-3-(2-bromophenyl)-3,4-dihydro-1-[3-((1,1-dimethyl-2-hydroxy)ethyl)phenyl]pyrimido[4,5-d]pyrimidin-2(1H)-one (prepared in Example 57) in a method analogous to that used in Example 54.

Example 59

A solution of 130 mg (0.31 mmol) of 3-(2-bromophenyl)-7-methanesulfonyl-3,4-dihydro-1-[3-(2-phthalimidoethyl)phenyl]pyrimido[4,5-d]pyrimidin-2(1H)-one from Example 50 was treated with 1 g (8 mmol) of 4-methoxyaniline. The mixture was heated to 120° C. for 2 hours. The mixture was cooled and treated with 30 ml of 2M aqueous hydrochloric acid. The suspended solid was filtered, washed with water and dried. The solid was dissolved in 20 ml of ethanol and treated with 0.2 ml of hydrazine hydrate. After 18 hours the mixture was evaporated and the product purified by column chromatography on silica gel using dichloromethane/methanol/acetic acid/water (240:24:3:2) for the elution. Product-containing fractions were combined, evaporated and the residue evaporated with toluene. The residue was then dissolved in 50 ml of dichloromethane, washed with 50 ml of saturated aqueous sodium bicarbonate solution, dried over magnesium sulfate, filtered and evaporated to give 35 mg (31%) of 1-[3-(2-aminoethyl)phenyl]-3-(2-bromophenyl)-7-(4-methoxyanilino-3,4-dihydropyrimido[4,5-d]pyrimidin-2(1H)-one as a white solid of melting point 132–133° C.

Example 60

25 mg of 1-[3-(2-aminoethyl)phenyl]-3-(2-bromophenyl)-7-(4-methoxyanilino)-3,4-dihydropyrimido[4,5-d]pyrimidin-2(1H)-one (prepared in Example 59) was treated with 2 ml of 40% aqueous hydrobromic acid and the mixture heated at 150° C. for 2 hours. The mixture was cooled and evaporated. The residue was triturated with hexane to afford 20 mg (80%) of 1-[3-(2-aminoethyl)phenyl]-3-(2-bromophenyl)-7-(4-hydroxyanilino)-3,4-dihydropyrimido[4,5-d]pyrimidin-2(1H)-one hydrobromide as a white solid of melting point 210° C. (decomposition).

Example 61

A solution of 230 mg of 7-anilino-3-(2-bromophenyl)-3,4-dihydro-1-[3-(phthalimidomethyl)phenyl]pyrimido[4,5-d]pyrimidin-2(1H)-one in 10 ml of ethanol was treated with 0.5 ml of hydrazine hydrate. After 18 hours the mixture was evaporated and the product purified by column chromatography on silica gel using dichloromethane/methanol/acetic acid/water (240:24:3:2) for the elution. Product-containing fractions were combined, evaporated and the residue evaporated with toluene. The residue was then dissolved in 50 ml of dichloromethane, washed with 50 ml of saturated aqueous sodium bicarbonate solution, dried over magnesium sulfate, filtered and evaporated to give 5 mg (2.8%) of 1-[3-(aminomethyl)phenyl]-7-anilino-3-(2-bromophenyl)-3,4-dihydropyrimido[4,5-d]pyrimidin-2(1H)-one as a white solid of melting point 121° C.

The 7-anilino-3-(2-bromophenyl)-3,4-dihydro-1-[3-(phthalimidomethyl)phenyl]pyrimido[4,5-d]pyrimidin-2(1H)-one used as starting material was prepared as follows:

a) A solution of 5 g (33 mmol) of 3-nitrobenzyl alcohol in 100 ml of dimethylformamide was treated with 10.8 g (40 mmol) of tert-butyldiphenylchlorosilane, 6.7 g (99 mmol) of imidazole and 100 mg (0.9 mmol) of 4-(dimethylamino)pyridine and the mixture stirred at ambient temperature for 4 hours. The solvent was evaporated and the residue partitioned between 100 ml of ethyl acetate and 100 ml of 2M aqueous hydrochloric acid. The organic phase was washed with a further 50 ml of 2M aqueous hydrochloric acid, dried over magnesium sulfate, filtered and evaporated to afford 12.9 g (100%) of 3-(tert-butyldiphenylsilyloxymethyl)nitrobenzene as a colorless oil. [Mass spectrum (ESI) MH$^+$=392].

b) A solution of 12.9 g (33 mmol) of 3-(tert-butyldiphenylsilyloxymethyl)nitrobenzene in 150 ml of ethanol was treated with 1 g of 10% palladium on charcoal and then shaken in an atmosphere of hydrogen for 18 hours. The mixture was filtered and the filtrate evaporated to afford $^{1}$2 g (100%) of 3-(tert-butyldiphenylsilyloxymethyl)aniline as a colorless oil. [Mass spectrum (ESI) MH$^+$=362].

c) A solution of 2.32 g (10 mmol) of ethyl 4-chloro-2-methylthiopyrimidine-5-carboxylate in 30 ml of 1,4-dioxan was treated with 1.4 ml (10 mmol) of triethylamine and 4.7 g (13 mmol) of 3-(tert-butyldiphenylsilyloxymethyl)aniline. The mixture was heated to 50° C. for 18 hours and then evaporated. The residue was partitioned between 50 ml of ethyl acetate and 50 ml of 2M aqueous hydrochloric acid. The organic phase was dried over magnesium sulfate, filtered and evaporated to afford 5.6 g (100%) of ethyl 4-[3-(tert-butyldiphenylsilyloxymethyl)anilino]-2-methylthiopyrimidine-5-carboxylate as a colorless oil. [Mass spectrum (ESI) MH$^+$=558].

d) A solution of 5.6 g (10 mmol) of ethyl 4-[3-(tert-butyldiphenylsilyloxymethyl)anilino]-2-methylthiopyrimidine-5-carboxylate in 30 ml of tetrahydrofuran was added dropwise to an ice-cooled solution of 10 ml of a 1M solution of lithium aluminium hydride in tetrahydrofuran (10 mmol) in a further 20 ml of tetrahydrofuran. After 1 hour the reaction was cautiously quenched by the sequential addition of 1 ml of water, 1.5 ml of 2M aqueous sodium hydroxide and 2 ml of water. The mixture was filtered through hyflo filter aid and the solids washed thoroughly with tetrahydrofuran. The combined filtrate and washings were evaporated to afford 4.6 g(88%) of 4-[3-(tert-butyldiphenylsilyloxymethyl)anilino]-5-hydroxymethyl-2-methylthiopyrimidine as a yellow oil. [Mass spectrum (ESI) MH$^+$=516].

e) A solution of 7.7 g (15 mmol) of 4-[3-(tert-butyldiphenylsilyloxymethyl)anilino]-5-hydroxymethyl-2- methylthiopyrimidine in 100 ml of dichloromethane was treated with 13 g (150 mmol) of manganese dioxide and the mixture stirred for 18 hours. The mixture was filtered and the filtrate evaporated. The product was purified by flash chromatography on silica gel using ethyl acetate/hexane as eluent in a ratio of 1:2. Product-containing fractions were combined and evaporated to afford 3.5 g (46%) of 4-[3-(tert-butyldiphenylsilyloxymethyl)anilino]-2-methylthiopyrimidine-5-carboxaldehyde as a colorless oil. [Mass spectrum (ESI) MH$^+$=514]

f) A solution of 3.5 g (6.8 mmol) of 4-[3-(tert-butyldiphenylsilyloxymethyl)anilino]-2-methylthiopyrimidine-5-carboxaldehyde in 100 ml of toluene was treated with 12 g (7 mmol) of 2-bromoaniline and 100 mg (0.5 mmol) of toluenesulfonic acid monohydrate. The mixture was heated to reflux with azeotropic removal of water for 2 hours and then cooled and evaporated. The residue was dissolved in 20 ml of tetrahydrofuran and then added dropwise to an ice-cooled solution of 7 ml of 1M lithium aluminium hydride in tetrahydrofuran (7 mmol) in a further 20 ml of tetrahydrofuran. After 1 hour the reaction was cautiously quenched by the sequential addition of 1.5 ml of water, 2 ml of 2M aqueous sodium hydroxide and 3 ml of water. The mixture was filtered through hyflo filter aid and the solids washed thoroughly with tetrahydrofuran. The combined filtrate and washings were evaporated to afford 4.5 g (100%) of 5-((2-bromoanilino)methyl)-4-[3-(tert-butyldiphenylsilyloxymethyl)anilino]-2-methylthiopyrimidine as a white solid. [Mass spectrum (ESI) MH$^+$=670].

g) A solution of 4.5 g (6.8 mmol) 5-((2-bromoanilino)methyl)-4-[3-(tert-butyldiphenylsilyloxymethyl)anilino]-2-methylthiopyrimidine and 1.9 ml (13.6 mmol) of triethylamine in 50 ml of toluene was added dropwise to a solution of 7 ml of a 20% solution of phosgene in toluene (13.6 mmol) in a further 50 ml of toluene. The mixture was heated at reflux for 5 hours and the cooled. 50 ml of ethyl acetate and 60 ml of saturated aqueous sodium bicarbonate were added and the mixture separated. The organic phase was dried over magnesium sulfate, filtered and evaporated to afford 4.7 g (100%) of 3-(2-bromophenyl)-1-[3-(tert-butyldiphenylsilyloxymethyl)phenyl]-3,4-dihydro-7-methylthio-pyrimido[4,5-d]pyrimidin-2(1H)-one as a colorless oil. [Mass spectrum (ESI) MH$^+$=696].

h) A solution of 4.7 g (6.8 mmol) of 3-(2-bromophenyl)-1-[3-(tert-butyldiphenylsilyloxymethyl)phenyl]-3,4-dihydro-7-methylthio-pyrimido[4,5-d]pyrimidin-2(1H)-one in 100 ml of dichloromethane was treated with 4.6 g (13.6 mmol) of 3-chloroperbenzoic acid (50% w/w water) and the mixture stirred for 18 hours. 60 ml of saturated aqueous sodium bicarbonate was added. The organic phase was dried over magnesium sulfate and evaporated. The residue was recrystallized from ethanol to afford 4.3 g (87%) of 3-(2-bromophenyl)-1-[3-(tert-butyldiphenylsilyloxymethyl)phenyl]-3,4-dihydro-7-methanesulfonyl-pyrimido[4,5-d]pyrimidin-2(1H)-one as a white solid. [Mass spectrum (ESI) MH$^+$=728].

i) A solution of 400 mg (0.55 mmol) of 3-(2-bromophenyl)-1-[3-(tert-butyldiphenylsilyloxymethyl)phenyl]-3,4-dihydro-7-methanesulfonyl-pyrimido[4,5-d]pyrimidin-2(1H)-one in 30 ml of methanol was treated with 400 mg (11 mmol) of ammonium fluoride and the mixture heated at reflux for 1 hour. The mixture was evaporated and the product purified by flash chromatography on silica gel eluting with dichloromethane/methanol in a ratio of 20:1. The product-containing fractions were combined and evaporated to afford 257 mg (96%) of 3-(2-bromophenyl)-3,4-dihydro-1-[3-(hydroxymethyl)phenyl]-7-methanesulfonyl-pyrimido[4,5-d]pyrimidin-2(1H)-one as a white solid. [Mass spectrum (ESI) MH$^+$=490].

j) A solution of 257 mg (0.53 mmol) of 3-(2-bromophenyl)-3,4-dihydro-1-[3-(hydroxymethyl)phenyl]-7-methanesulfonyl-pyrimido[4,5-d]pyrimidin-2(1H)-one in 15 ml of dichloromethane was treated with 0.15 ml (1.06 mmol) of triethylamine and 104 mg (0.6 mmol) of methanesulfonic anhydride. After 18 hours 10 ml of saturated aqueous sodium bicarbonate was added. The mixture was separated and the organic phase dried over magnesium sulfate, filtered and evaporated to afford 250 mg (83%) of 3-(2-bromophenyl)-3,4-dihydro-7-(methanesulfonyl)-1-[3-(methanesulfonyloxymethyl)phenyl]pyrimido[4,5-d]pyrimidin-2(1H)-one as a colorless oil. [Mass spectrum (ESI) MH$^+$=567].

k) A solution of 250 mg (0.44 mmol) of 3-(2-bromophenyl)-3,4-dihydro-7-(methanesulfonyl)-1-[3-(methanesulfonyloxymethyl)phenyl]pyrimido[4,5-d]pyrimidin-2(1H)-one in 10 ml of dimethylformamide was treated with 111 mg (0.6 mmol) of potassium phthalimide and the mixture heated at 90° C. for 1 hour then cooled and evaporated. The residue was partitioned between 30 ml of dichloromethane and 30 ml of water. The organic phase was collected, dried over magnesium sulfate, filtered and evaporated to afford 270 mg (99%) of 3-(2-bromophenyl)-3,4-dihydro-7-(methanesulfonyl)-1-[3-(phthalimidomethyl)phenyl]pyrimido[4,5-d]pyrimidin-2(1H)-one as a white solid. [Mass spectrum (ESI) MH$^+$=618].

l) 270 mg (0.44 mmol) of 3-(2-bromophenyl)-3,4-dihydro-7-(methanesulfonyl)-1-[3-(phthalimidomethyl)phenyl]pyrimido[4,5-d]pyrimidin-2(1H)-one was treated with 3 ml of aniline and the mixture heated to 180° C. for 20 minutes and cooled. 20 ml of ethyl acetate and 20 ml of 2M aqueous hydrochloric acid were added. The organic phase was dried over magnesium sulfate, filtered and evaporated to afford 230 mg (83%) of 7-anilino-3-(2-bromophenyl)-3,4-dihydro-1-[3-(phthalimidomethyl)phenyl]pyrimido[4,5-d]pyrimidin-2(1H)-one as a tan solid. [Mass spectrum (ESI)= 632].

Example 62

A solution of 1.5 g (2 mmol) of 7-anilino-3-(2-bromophenyl)-1-[3-((tert-butyldiphenylsilyloxy)methyl)phenyl]-3,4-dihydro-pyrimido[4,5-d]pyrimidin-2(1H)-one in 30 ml of tetrahydrofuran was treated with 2.5 ml (2.5 mmol) of tetrabutylammonium fluoride (1M in tetrahydrofuran). The mixture was heated at reflux for 5 hours, cooled and evaporated. The residue was partitioned between 50 ml of ethyl acetate and 50 ml of 2M aqueous hydrochloric acid. The organic phase was washed with 40 ml of water, dried over magnesium sulfate, filtered and evaporated. The residue was purified by flash chromatography on silica gel using dichloromethane/methanol 100:1 as eluent. Product-containing fractions were evaporated to give 550 mg (55%) of 7-anilino-3-(2-bromophenyl)-3,4-dihydro-1-[3-(hydroxymethyl)phenyl]pyrimido[4,5-d]pyrimidin-2 (1H)-one as a white solid of melting point 136° C. [Mass spectrum (ESI) MH$^+$=486].

The 7-anilino-3-(2-bromophenyl)-1-[3-((tert-butyldiphenylsilyloxy)methyl)phenyl]-3,4-dihydro-pyrimido[4,5-d]pyrimidin-2(1H)-one used as starting material was prepared as follows:

1.5 g (2 mmol) of 3-(2-bromophenyl)-1-[3-(tert-butyldiphenylsilyloxymethyl)phenyl]-3,4-dihydro-7-methanesulfonyl-pyrimido[4,5-d]pyrimidin-2(1H)-one (prepared in Example 61(h)) was treated with 3 ml of aniline and the mixture heated at 180° C. for 20 minutes and cooled. The mixture was poured into 50 ml of 2M aqueous hydrochloric acid and the precipitated product filtered off, washed with water and dried to afford 1.5 g (100%) of 7-anilino-3-(2-bromophenyl)-1-[3-((tert-butyldiphenylsilyloxy)methyl)phenyl]-3,4-dihydropyrimido[4,5-d]pyrimidin-2(1H)-one as a light brown solid. [Mass spectrum (ESI) MH$^+$=741].

Example 63

A mixture of 180 mg (0.37 mmol) of 3-(2-bromophenyl)-3,4-dihydro-1-[4-(hydroxymethyl)phenyl]-7-methanesulfonyl-pyrimido[4,5-d]pyrimidin-2(1H)-one and 0.34 ml (3.7 mmol) of aniline was heated at 120° C. for 3 hours. The reaction mixture was cooled to room temperature then triturated with 5 ml of 2M hydrochloric acid. The fawn solid was collected by filtration, washed with water then diethyl ether. The crude material was purified by flash chromatography on silica gel, using 3% methanol in dichloromethane for the elution. Product containing fractions were combined and evaporated to give 65 mg (35%) of 7-anilino-3-(2-bromophenyl)-3,4-dihydro-1-[4-(hydroxymethyl)phenyl]pyrimido[4,5-d]pyrimidin-2(1H)-one as an off-white solid of melting point 129–132° C. [Mass spectrum (ESI) MH$^+$=502].

The 3-(2-bromophenyl)-3,4-dihydro-1-[4-(hydroxymethyl)phenyl]-7-methanesulfonyl-pyrimido[4,5-d]pyrimidin-2(1H)-one used as the starting material was prepared as follows:

a) A solution of 5.9 g (38.7 mmol) of 4-nitrobenzyl alcohol, 17.6 ml(193.5 mmol) of 3,4-dihydro-2H-pyran and 500 mg (2.6 mmol) of p-toluene sulfonic acid monohydrate in 200 ml of dichloromethane was stirred at room temperature for 4 hours. The reaction mixture was evaporated and the residue purified by flash chromatography on silica gel, using 1:4 ethyl acetate/hexane as eluent. Product containing fractions were combined and evaporated to give 8.52 g (93%) of 2-(4-nitrobenzyloxy)-tetrahydropyran as a pale yellow oil.

b) A solution of 8.5 g (35.9 mmol) of 2-(4-nitrobenzyloxy)-tetrahydropyran in 150 ml of methanol was hydrogenated at room temperature and atmospheric pressure in the presence of 800 mg of 10% palladium on carbon for 8 hours. The catalyst was removed by filtration and the filtrate evaporated to give a dark yellow oil. Purification by flash column chromatography on silica gel using 1:2 ethyl acetate/hexane as eluent gave 4.8 g (65%) of 4-(tetrahydropyran-2-yloxymethyl)aniline as a pale yellow oil. [Mass spectrum (ESI) [MH+MeCN]$^+$=249].

c) A solution of 4.25 g (18.26 mmol) of ethyl 4-chloro-2-methylthio-pyrimidine-5-carboxylate, 4.73 g (22.85 mmol) of 4-(tetrahydropyran-2-yloxymethyl)aniline and 6.4 ml (45.7 mmol) of triethylamine in sieve-dried 1,4-dioxan was heated at 60° C. for 4 hours. The reaction mixture was evaporated and the residue partitioned between ethyl acetate and water. The ethyl acetate layer was separated, dried (MgSO$_4$) and evaporated to give a brown oil which was purified by flash chromatography on silica gel using1:4 ethyl acetate/hexane as eluent. Product containing fractions were combined and evaporated to give 6.68 g (90%) of ethyl 4-[4-(tetrahydropyran-2-yloxymethyl)phenyl]amino-2-methylthiopyrimidine-5-carboxylate as a yellow oil. [Mass spectrum (ESI) MH$^+$=404].

d) A solution of 6.6 g (16.37 mmol) of ethyl 4-[4-(tetrahydropyran-2-yloxymethyl)phenyl]amino-2-methylthiopyrimidine-5-carboxylate in 100 ml of anhydrous tetrahydrofuran was added dropwise to 20.5 ml (20.5 mmol) of lithium aluminium hydride (1M in tetrahydrofuran) in 100 ml of anhydrous tetrahydrofuran at 0° C. The reaction was warmed to room temperature for 2 hours then to 65° C. where it was quenched by the sequential addition of 0.75 ml of water, 0.75 ml of 2M sodium hydroxide solution and 2.25 ml of water. The reaction was allowed to cool then filtered through filter aid and the filtrate evaporated to give 4.5 g (75%) of 4-[4-(tetrahydropyran-2-yloxymethyl)phenyl]amino-5-hydroxymethyl-2-methylthiopyrimidine as a yellow semi-solid.

e) Reaction of 4.54 g (12.57 mmol) of 4-[4-(tetrahydropyran-2-yloxymethyl)phenyl]amino-5-hydroxymethyl-2-methylthiopyrimidine in a method analogous to Example 7(c) gave 4.02 g (89%) of 5-formyl-4-[4-(tetrahydropyran-2-yloxymethyl)phenyl]amino-2-methylthiopyrimidine.

f) Reaction of 4.0 g (11.1 mmol) of 5-formyl-4-[4-(tetrahydropyran-2-yloxymethyl)phenyl]amino-2-methylthiopyrimidine with 2-bromoaniline in a method analogous to Example 37(f) gave 1.13 g (24%) of 5-(2-bromoanilino)methyl-4-[4-(tetrahydropyran-2-yloxymethyl)phenyl]amino-2-methylthiopyrimidine as a pale yellow gum. [Mass spectrum (ESI) MH$^+$=515].

g) A solution containing 0.93 g (1.8 mmol) of 5-(2-bromoanilino)methyl-4-[4-(tetrahydropyran-2-yloxymethyl)phenyl]amino-2-methylthiopyrimidine and 0.5 ml (3.61 mmol) of triethylamine in 5 ml of anhydrous tetrahydrofuran was added dropwise to 1.9 ml (3.61 mmol) of a 20% solution of phosgene in toluene dissolved in 5 ml of tetrahydrofuran at 0° C. under an atmosphere of nitrogen. The reaction was stirred at 0° C. for a further 60 minutes then evaporated. The residue was partitioned between ethyl acetate (10 ml) and 2M hydrochloric acid (10 ml), the ethyl acetate layer was separated then washed with saturated aqueous sodium bicarbonate (10 ml), dried over magnesium sulfate, filtered and evaporated to give 0.945 g (97%) of 3-(2-bromophenyl)-3,4-dihydro-1-[4-(tetrahydropyran-2-yloxymethyl)phenyl]-7-methylthio-pyrimido[4,5-d]pyrimidin-2(1H)-one as a yellow gum. [Mass spectrum (ESI) MH$^+$=541].

h) A solution of 0.945 mg (1.75 mmol) of 3-(2-bromophenyl)-3,4-dihydro-1-[4-(tetrahydropyran-2-yloxymethyl)phenyl]-7-methylthio-pyrimido[4,5-d]pyrimidin-2(1H)-one in 10 ml of saturated hydrogen chloride in ethyl acetate was stirred at room temperature for 2 hours. The reaction was diluted with ethyl acetate (10 ml) then washed with water (10 ml) and saturated aqueous sodium bicarbonate (20 ml), dried over magnesium sulfate, filtered and evaporated to give 0.68 g (85%) of 3-(2-bromophenyl)-3,4-dihydro-1-[4-(hydroxymethyl)phenyl]-7-methylthio-pyrimido[4,5-d]pyrimidin-2(1H)-one as a yellow gum. [Mass spectrum (ESI) MH$^+$=457].

i) 0.68 g (1.49 mmol) of 3-(2-bromophenyl)-3,4-dihydro-1-[4-(hydroxymethyl)phenyl]-7-methylthio-pyrimido[4,5-d]pyrimidin-2(1H)-one was reacted with 3-chloroperbenzoic acid in a manner analogous to 7 f to give 0.36 g (49%) of 3-(2-bromophenyl)-3,4-dihydro-1-[4-(hydroxymethyl)phenyl]-7-methanesulfonyl-pyrimido[4,5-d]pyrimidin-2(1H)-one as a cream foam. [Mass spectrum (ESI) MH$^+$=491].

Example 64

A solution of 160 mg (0.253 mmol) of 7-anilino-3-(2-bromophenyl)-3,4-dihydro-1-[4-(phthalimidomethyl)phenyl]pyrimido[4,5-d]pyrimidin-2(1H)-one and 0.5 ml of hydrazine hydrate in 5 ml of ethanol was stirred at room temperature under an atmosphere of nitrogen for 4 hours. The reaction mixture was evaporated and the residue purified by flash chromatography on silica gel using dichloromethane/methanol/acetic acid/water (240:24:3:2) as the eluent. Product containing fractions were combined and evaporated and the residue re-evaporated with toluene. The residue was then dissolved in 20 ml of dichloromethane, washed with saturated aqueous sodium bicarbonate (20 ml), dried over magnesium sulfate, filtered and evaporated to give 55 mg (43%) of 1-[4-(aminomethyl)phenyl]-7-anilino-3-(2-bromophenyl)-3,4-dihydropyrimido[4,5-d]pyrimidin-2(1H)-one as a white solid of melting point 133–136° C. [Mass spectrum (ESI) MH$^+$=501].

The 7-anilino-3-(2-bromophenyl)-3,4-dihydro-1-[4-(phthalimidomethyl)phenyl]pyrimido[4,5-d]pyrimidin-2(1H)-one used as the starting material was prepared from 7-anilino-3-(2-bromophenyl)-3,4-dihydro-1-[4-(hydroxymethyl)phenyl]pyrimido[4,5-d]pyrimidin-2(1H)-one (prepared in Example 63) in a method analogous to that described in Example 54.

Example 65

A mixture of 160 mg (0.3 mmol) of 3-(2-bromophenyl)-3,4-dihydro-7-methanesulfonyl-1-(1-naphthyl)pyrimido[4,5-d]pyrimidin-2(1H)-one and 200 μl (2.2 mmol) of aniline was heated at 120° C. for 2 hours. The residue was partitioned between ethyl acetate (10 ml) and 2M hydrochloric acid (10 ml) and the ethyl acetate layer separated then washed with saturated aqueous sodium bicarbonate (10 ml), dried over magnesium sulfate, filtered and evaporated to give 100 mg (67%) of 7-anilino-3-(2-bromophenyl)-3,4-dihydro-1-(1-naphthyl)pyrimido[4,5-d]pyrimidin-2(1H)-one as an orange solid of melting point 120–125° C. [Mass spectrum (ESI) MH$^+$=522].

The 3-(2-bromophenyl)-3,4-dihydro-7-methanesulfonyl-1-(1-naphthyl)pyrimido[4,5-d]pyrimidin-2(1H)-one used as the starting material was prepared in a method analogous to that described in Example 7 from ethyl 4-chloro-2-methylthio-pyrimidine-5-carboxylate and 1-naphthylamine.

Example 66

A mixture of 0.655 g (1.1 mmol) of methyl 3-[[7-benzylsulfonyl-3-(2-bromophenyl)-1,2,3,4-tetrahydro-2-oxopyrimido[4,5-d]pyrimidin-1-yl]methyl]benzoate and 0.55 ml (6 mmol) of aniline was heated at 100° C. for 2 hours. The reaction mixture was partitioned between dichloromethane(10 ml) and 2M hydrochloric acid (10 ml) and the dichloromethane layer separated, washed with saturated aqueous sodium bicarbonate (10 ml), dried over magnesium sulfate, filtered and evaporated. The crude material was purified by flash chromatography on silica gel using 1:1 ethyl acetate/hexane as the eluent. Product containing fractions were combined and evaporated to give 120 mg (20%) of methyl 3-[[7-anilino-3-(2-bromophenyl)-1,2,3,4-tetrahydro-2-oxopyrimido[4,5-d]pyrimidin-1-yl]methyl]benzoate as a white solid of melting point 79–82° C. [Mass spectrum (ESI) MH$^+$=546].

The methyl 3-[[7-benzylsulfonyl-3-(2-bromophenyl)-1,2,3,4-tetrahydro-2-oxopyrimido[4,5-d]pyrimidin-1-yl]methyl]benzoate used as the starting material was prepared as follows:

a) 650 μl (8.8 mmol) of thionyl chloride was added dropwise to a stirred solution of 1 g (5.8 mmol) of 3-(chloromethyl) benzoic acid in 40 ml of methanol at 0° C. under a nitrogen atmosphere, then stirred at room temperature overnight. The solvent was evaporated, the residue dissolved in dichloromethane (30 ml), washed with saturated aqueous sodium bicarbonate (2×40 ml), brine (40 ml), dried over magnesium sulfate, filtered and evaporated to give 0.94 g (88%) of methyl-3-(chloromethyl)benzoate as a colorless mobile liquid.

b) A solution of 1 g (2.2 mmol) of 7-benzylsulfonyl-3-(2-bromophenyl)-3,4-dihydropyrimido[4,5-d]pyrimidin-2(1H)-one in 20 ml of dimethylformamide was cooled to 0° C. under a nitrogen atmosphere, treated with 112 mg (4.2 mmol) of 60% sodium hydride in mineral oil then stirred for 30 minutes. 440 mg (2.4 mmol) of methyl- 3-(chloromethyl) benzoate was added, then the reaction was heated at 90° C. for 3 hours. The solvent was evaporated and the residue partitioned between ethyl acetate (40 ml) and water (40 ml), the ethyl acetate layer was separated, washed with saturated aqueous sodium bicarbonate (40 ml), dried over magnesium sulfate, filtered and evaporated. The crude material was purified by flash chromatography on silica gel, eluting with 1:1 ethyl acetate/hexane. Product containing fractions were combined and evaporated to give 750 mg (56%) of methyl 3-[[7-benzylsulfonyl 3-(2-bromophenyl)-1,2,3,4-tetrahydro-2-oxopyrimido[4,5-d]pyrimid-1-yl]methyl]benzoate as a white solid. [Mass spectrum (ESI) MH$^+$=607].

The 7-benzylsulfonyl-3-(2-bromophenyl)-3,4-dihydropyrimido[4,5-d]pyrimidin-2(1H)-one was prepared in a manner analogous to that described in Example 8(a)–(f) starting from commercially available 4-amino-5-carbethoxypyrimidine-2-thiol and using benzyl bromide in place of iodomethane and 2-bromoaniline in place of 2,6-dichloroaniline.

Example 67

A solution of 90 mg (0.17 mmol) of methyl 3-[[7-anilino-3-(2-bromophenyl)-1,2,3,4-tetrahydro-2-oxopyrimido[4,5-d]pyrimidin-1-yl]methyl]benzoate in tetrahydrofuran/methanol/water (6 ml:6 ml:1.5 ml) was treated with 27 mg (1.125 mmol) of lithium hydroxide monohydrate then heated at 60° C. for 3 hours under a nitrogen atmosphere. The solvent was evaporated and the residue partitioned between ethyl acetate (10 ml) and 2M hydrochloric acid (10 ml). The ethyl acetate layer was separated, washed with saturated aqueous sodium bicarbonate (10 ml), dried over magnesium sulfate, filtered and evaporated to give 30 mg (35%) of 3-[[7-anilino-3-(2-bromophenyl)-1,2,3,4-tetrahydro-2-oxopyrimido[4,5-d]pyrimidin-1-yl]methyl] benzoic acid as a pale yellow solid of melting point 180–183° C. [Mass spectrum (ESI) MH$^+$=530].

Example 68

A mixture of 158 mg (0.35 mmol) of 3-(2,6-dichlorophenyl)-7-methanesulfonyl-3,4-dihydro-1-phenylpyrimido[4,5-d]pyrimidin-2(1H)-one (prepared in Example 7) and 250 μl (1.9 mmol) of 4-ethoxyaniline were heated at 90° C. for 2 hours. The reaction mixture was partitioned between dichloromethane (10 ml) and 2M hydrochloric acid (10 ml) and the dichloromethane layer separated, washed with saturated aqueous sodium bicarbonate (10 ml), dried over magnesium sulfate, filtered and evaporated. The crude material was purified by flash chromatography on silica gel, eluting with 1:1 ethyl acetate/hexane. Product containing fractions were combined and evaporated to give 126 mg (71%) of 3-(2,6-dichlorophenyl)-7-(4-ethoxyanilino)-3,4-dihydro-1-phenylpyrimido[4,5-d] pyrimidin-2(1H)-one as a white solid of melting point 224–226° C. [Mass spectrum (ESI) MH$^+$=506].

Example 69

A solution of 960 mg (1.29 mmol) of 7-anilino-1-[3-(2-tert-butyldiphenylsilyloxyethyl)phenyl]-3-(2,6-dichlorophenyl)-3,4-dihydro-pyrimido[4,5-d]pyrimidin-2(1H)-one in dry tetrahydrofuran (8 ml) was treated with 1.6 ml of a 1M solution of tetrabutylammonium fluoride in tetrahydrofuran at 0° C. The reaction was allowed to warm to room temperature overnight. The solvent was evaporated and the residue partitioned between ethyl acetate (30 ml) and 2M hydrochloric acid (30 ml) and the ethyl acetate layer separated, washed with saturated aqueous sodium bicarbonate (30 ml), dried over magnesium sulfate, filtered and evaporated to give 730 mg of a dark brown solid. The crude material was triturated with diethyl ether, the solid was collected by filtration and washed with more diethyl ether to give 240 mg (37%) of 7-anilino-3-(2,6-dichlorophenyl)-3,4-dihydro-1-[3-(2-hydroxyethyl)phenyl]pyrimido[4,5-d]pyrimidin-2(1H)-one as an off white solid of melting point >250° C. [Mass spectrum (ESI) MH$^+$=506].

The 7-anilino-1-[3-(2-t-butyldiphenylsilyloxyethyl)phenyl]-3-(2,6-dichlorophenyl)-3,4-dihydro-pyrimido[4,5-d]pyrimidin-2(1H)-one used as starting material was prepared as follows:

a) A solution of 0.8 g (1.84 mmol) of 5-(2,6-dichloroanilino)methyl-4-[3-(2-hydroxyethyl)phenyl]amino-2-methylthiopyrimidine (prepared in Example 37(f)), 580 μl (2.2 mmol) of tert-butylchlorodiphenylsilane, 0.38 mg (5.5 mmol) of imidazole and 15 mg of N,N-dimethylaminopyridine in dimethylformamide (5 ml) was stirred under a nitrogen atmosphere at room temperature overnight. The solvent was evaporated and the residue partitioned between ethyl acetate (40 ml) and 2M hydrochloric acid (40 ml), and the ethyl acetate layer separated, washed with saturated aqueous sodium bicarbonate (40 ml), dried over magnesium sulfate, filtered and evaporated to give 1.36 g of 4-[3-( 2-tertbutyldiphenylsilyloxyethyl)phenyl]amino-5-(2,6-dichloroanilino)methyl-2-methylthiopyrimidine as a yellow gum. [Mass spectrum (ESI) MH$^+$=673].

b) A solution containing 1.35 g (2 mmol) of 4-[3-(2-tertbutyldiphenylsilyloxyethyl)phenyl]amino-5-(2,6-dichloroanilino)methyl-2-methylthiopyrimidine and 0.85 ml (6 mmol) of triethylamine in 5 ml of anhydrous toluene was added dropwise to 3.2 ml (6 mmol) of a 20% solution of phosgene in toluene dissolved in 10 ml of toluene at 0° C. under an atmosphere of nitrogen. The reaction was then heated at reflux for 6 hours then evaporated. The residue was partitioned between ethyl acetate (40 ml) and 2M hydrochloric acid (40 ml) and the ethyl acetate layer separated, washed with saturated aqueous sodium bicarbonate (40 ml ), dried over magnesium sulfate, filtered and evaporated to give 1.5 g of 1-[3-(2-t-butyldiphenylsilyloxyethyl)phenyl]-3-(2,6-dichlorophenyl)-7-methylthio-3,4-dihydropyrimido[4,5-d]pyrimidin-2(1H)-one as a yellow gum. [Mass spectrum (ESI) MH$^+$=699].

c) 1.4 g (2 mmol) of 1-[3-(2-t-butyldiphenylsilyloxyethyl)phenyl]-3-(2,6-dichlorophenyl)-7-methylthio-3,4-dihydropyrimido[4,5-d]pyrimidin-2(1H)-one was reacted with 3-chloroperbenzoic acid in a manner analogous to that described in Example 7(f) to give 0.98 g (67%) of 1-[3-(2-tert-butyldiphenylsilyloxyethyl)phenyl]-3-(2,6-dichlorophenyl)-7-methanesulfonyl-3,4-dihydropyrimido[4,5-d]pyrimidin-2(1H)-one as a cream solid. [Mass spectrum (ESI) MH$^+$=731].

d) A mixture of 980 mg (1.22 mmol) of 1-[3-(2-t-butyldiphenylsilyloxyethyl)phenyl]-3-(2,6-dichlorophenyl)-7-methanesulfonyl-3,4-dihydropyrimido[4,5-d]pyrimidin-2(1H)-one and 5 ml of aniline was heated at 100° C. for 30 minutes. The reaction was allowed to cool then poured into 50 ml of 2M hydrochloric acid. The product was collected by filtration, washed with water (50 ml), then hexane (50 ml) and dried to give 960 mg (96%) of 7-anilino-1-[3-(2-tert-butyldiphenylsilyloxyethyl)phenyl]-3-(2,6-dichlorophenyl)-3,4-dihydro-pyrimido[4,5-d]pyrimidin-2(1H)-one as a fawn solid. [Mass spectrum (ESI) MH$^+$=744].

Example 70

A solution of 125 mg (0.214 mmol) of 7-anilino-3-(2,6-chlorophenyl)-3,4-dihydro-1-[3-(2-methanesulfonyloxyethyl)phenyl]pyrimido[4,5-d]pyrimidin-2(1H)-one in 5 ml of 33% methylamine in ethanol was heated at 60° C. for 3 hours. The reaction mixture was evaporated and the crude material purified by flash chromatography on silica gel, eluting with dichloromethane/methanol/acetic acid/water (120:14:3:2). Product-containing fractions were combined, evaporated and the residue evaporated with toluene. The residue was then dissolved in 50 ml of dichloromethane, washed with 50 ml of saturated aqueous sodium bicarbonate solution, dried over magnesium sulfate, filtered and evaporated to give 38 mg (34%) of 7-anilino-3-(2,6-dichlorophenyl)-3,4-dihydro-1-[3-[2-(methylamino)ethyl]phenyl]pyrimido[4,5-d]pyrimidin-2(1H)-one as a white solid of melting point 122–125° C. [Mass spectrum (ESI) MH$^+$=519].

The 7-anilino-3-(2,6-chlorophenyl)-3,4-dihydro-1-[3-(2-methanesulfonyloxyethyl)phenyl]pyrimido[4,5-d]pyrimidin-2(1H)-one used as the starting material was prepared in a manner analogous to that described in Example 54(a) from 7-anilino-3-(2,6-dichlorophenyl)-3,4-dihydro-1-[3-(2-hydroxyethyl)phenyl]pyrimido[4,5-d]pyrimidin-2(1H)-one (prepared in Example 69).

Example 71

A solution of 125 mg (0.214 mmol) of 7-anilino-3-(2,6-chlorophenyl)-3,4-dihydro-1-[3-(2-methanesulfonyloxyethyl)phenyl]pyrimido[4,5-d]pyrimidin-2(1H)-one (prepared as described in Example 70) in 5 ml of 33% dimethylamine in ethanol was heated at 60° C. for 3 hours. The reaction mixture was evaporated and the crude material purified by flash chromatography on silica gel, eluting with dichloromethane/methanol/acetic acid/water (120:14:3:2). Product-containing fractions were combined, evaporated and the residue evaporated with toluene. The residue was then dissolved in 50 ml of dichloromethane, washed with 50 ml of saturated aqueous sodium bicarbonate solution, dried over magnesium sulfate, filtered and evaporated to give 18 mg (16%) of 7-anilino-3-(2,6-dichlorophenyl)-3,4-dihydro-1-[3-[2-(dimethylamino)ethyl]phenyl]pyrimido[4,5-d]pyrimidin-2(1H)-one as a white of melting point 101–105° C. [Mass spectrum (ESI) MH$^+$=533].

Example 72

A mixture of 1.09 g (2.2 mmol) of 3-(2,4-dichlorophenyl)-3,4-dihydro-1-[3-(2-hydroxyethyl)phenyl]-7-methanesulfonyl-pyrimido[4,5-d]pyrimidin-2(1H)-one and aniline was heated at 120° C. for 1 hour. The reaction mixture was partitioned between dichloromethane (20 ml) and 2M hydrochloric acid (20 ml) and the dichloromethane layer separated, washed with saturated aqueous sodium bicarbonate (20 ml), dried over magnesium sulfate, filtered and evaporated. The crude material was purified by flash chromatography on silica gel, eluting with 5:1 ethyl acetate/hexane. Product containing fractions were combined and evaporated to give 630 mg (55%) of 7-anilino-3-(2,4-dichlorophenyl)-3,4-dihydro-1-[3-(2-hydroxyethyl)phenyl]pyrimido[4,5-d]pyrimidin-2(1H)-one as a white solid of melting point 213–217° C. [Mass spectrum (ESI) MH$^+$=506].

The 3-(2,4-dichlorophenyl)-3,4-dihydro-1-[3-(2-hydroxyethyl)phenyl]-7-methanesulfonyl-pyrimido[4,5-d]pyrimidin-2(1H)-one used as the starting material was prepared as follows:

a) 1.97 g (2.83 mmol) of 1-[3-(2-tertbutyldiphenylsilyloxyethyl)phenyl]-3-(2,4-dichlorophenyl)-3,4-dihydro-7-methylthio-pyrimido[4,5-d]pyrimidin-2(1H)-one (prepared in a manner analogous to that described in Example 53(a)–(b) using 2,4-dichloroaniline in place of 2-chloro-6-methylaniline) was reacted with a 1M solution of tetrabutylammonium fluoride in a manner analogous to that described in Example 69. 1.3 g (100%) of 3-(2,4-dichlorophenyl)-3,4-dihydro-1-[3-(2-hydroxyethyl)phenyl]-7-methylthio-pyrimido[4,5-d]pyrimidin-2(1H)-one was isolated as a yellow solid. [Mass spectrum (ESI) MH$^+$=461].

b) 1.3 g (2.8 mmol) of 3-(2,4-dichlorophenyl)-3,4-dihydro-1-[3-(2-hydroxyethyl)phenyl]-7-methylthio-pyrimido[4,5-d]pyrimidin-2(1H)-one was reacted with 3-chloroperbenzoic acid in a manner analogous to that described in Example 7(f) to give 1.1 (78%) of 3-(2,4-dichlorophenyl)-3,4-dihydro-1-[3-(2-hydroxyethyl)phenyl]-7-methanesulfonylpyrimido[4,5-d]pyrimidin-2(1H)-one as a cream solid. [Mass spectrum (ESI) MH$^+$=493].

Example 73

A solution of 370 mg (0.6 mmol) of 7-anilino-3-(2,4-dichlorophenyl)-3,4-dihydro-1-[3-(2-phthalimidoethyl)phenyl]pyrimido[4,5-d]pyrimidin-2(1H)-one and 0.3 ml (6 mmol) of hydrazine hydrate in 5 ml of dichloromethane/methanol was stirred at room temperature under an atmosphere of nitrogen overnight. The reaction mixture was evaporated and the residue purified by flash chromatography on silica gel, eluting with dichloromethane/methanol/acetic acid/water (120:14:3:2). Product containing fractions were combined and evaporated and the residue re-evaporated with toluene. The residue was then dissolved in 20 ml of dichloromethane, washed with saturated aqueous sodium bicarbonate (20 ml), dried over magnesium sulfate, filtered and evaporated to give 100 mg (33%) of 1-[3-(2-aminoethyl)phenyl]-7-anilino-3-(2,4-dichlorophenyl)-3,4-dihydropyrimido[4,5-d]pyrimidin-2(1H)-one as a white solid of melting point 131–135° C. [Mass spectrum (ESI) MH$^+$=505].

The 7-anilino-3-(2,4-dichlorophenyl)-3,4-dihydro-1-[3-(2-phthalimidoethyl)phenyl]pyrimido[4,5-d]pyrimidin-2(1H)-one used as the starting material was prepared from 7-anilino-3-(2,4-dichlorophenyl)-3,4-dihydro-1-[3-(2-hydroxyethyl)phenyl]pyrimido[4,5-d]pyrimidin-2(1H)-one (prepared in Example 72) in a method analogous to that described in Example 54.

Example 74

A solution of 120 mg (0.2 mmol) of 7-anilino-3-(2,4-dichlorophenyl)-3,4-dihydro-1-[3-(2-methanesulfonyloxyethyl)phenyl]pyrimido[4,5-d]pyrimidin-2(1H)-one in 4 ml of 40% methylamine in ethanol was heated at 50° C. for 3 hours. The reaction mixture was evaporated and the crude material purified by flash column chromatography on silica gel eluting with dichloromethane/methanol/acetic acid/water (120:14:3:2). Product containing fractions were combined and evaporated to give 18 mg (16%) of 7-anilino-3-(2,4-dichlorophenyl)-3,4-dihydro-1-[3-[2-(methylamino)ethyl]phenyl]pyrimido[4,5-d]pyrimidin-2(1H)-one as a solid of melting point 120–122° C. [Mass spectrum (ESI) MH$^+$=519].

The 7-anilino-3-(2,4-chlorophenyl)-3,4-dihydro-1-[3-(2-methanesulfonyloxyethyl)phenyl]pyrimido[4,5-d]pyrimidin-2(1H)-one used as the starting material was prepared from 7-anilino-3-(2,4-dichlorophenyl)-3,4-dihydro-1-[3-(2-hydroxyethyl)phenyl]pyrimido[4,5-d]pyrimidin-2(1H)-one (prepared in Example 72) in a method analogous to that described in Example 54(a).

Example 75

A solution of 204 mg (0.35 mmol) of 7-anilino-3-(2,4-chlorophenyl)-3,4-dihydro-1-[3-(2-methanesulfonyloxyethyl)phenyl]pyrimido[4,5-d]pyrimidin-2(1H)-one (prepared in Example 74) in 4 ml of 33% dimethylamine in ethanol was heated at 40° C. for 2 hours. The reaction was evaporated and the crude material purified by flash chromatography on silica gel eluting with dichloromethane/methanol/acetic acid/water (120:14:3:2). Product containing fractions were combined and evaporated to give 80 mg (43%) of 7-anilino-3-(2,4-dichlorophenyl)-3,4-dihydro-1-[3-[2-(dimethylamino)ethyl]phenyl]pyrimido[4,5-d]pyrimidin-2(1H)-one as a white solid of melting point 101–105° C. [Mass spectrum (ESI) MH$^+$=533].

Example 76

A mixture of 240 mg (0.4 mmol) of 7-benzylsulfonyl-3-(2-bromophenyl)-1-cyclohexylmethyl-3,4-dihydro-pyrimido[4,5-d]pyrimidin-2(1H)-one and 0.39 ml (4.3 mmol) of aniline was heated at 150° C. for 2 hours. The reaction mixture was cooled to room temperature then partitioned between 2M hydrochloric acid (20 ml) and dichloromethane (20 ml). The organic layer was separated, washed with saturated aqueous sodium bicarbonate (20 ml), dried over magnesium sulfate, filtered and evaporated. The crude material was purified by flash chromatography on silica gel, eluting with 1:2 ethyl acetate/hexane. Product containing fractions were combined and evaporated to give 80 mg (42%) of 7-anilino-3-(2-bromophenyl)-1-cyclohexylmethyl-3,4-dihydro-pyrimido[4,5-d]pyrimidin-2(1H)-one as an off-white solid of melting point 200–202° C. [Mass spectrum (ESI) MH$^+$=492].

The 7-benzylsulfonyl-3-(2-bromophenyl)-1-cyclohexylmethyl-3,4-dihydro-pyrimido[4,5-d]pyrimidin-2(1H)-one used as the starting material was prepared from 7-benzylsulfonyl-3-(2-bromophenyl)-3,4-dihydropyrimido[4,5-d]pyrimidin-2(1H)-one (prepared in Example 66) and bromomethylcyclohexane in a method analogous to that described in Example 66(b).

Example 77

A solution of 195 mg (0.3 mmol) of 7-anilino-3-(2,4-dichlorophenyl)-3,4-dihydro-1-[4-(2-phthalimidoethyl)phenyl]-pyrimido[4,5-d]pyrimidin-2(1H)-one and 150 µl (3 mmol) of hydrazine hydrate in methanol/dichloromethane (3 ml:3 ml) was stirred at room temperature under an atmosphere of nitrogen overnight. The reaction mixture was evaporated and the residue purified by flash chromatography on silica gel eluting with dichloromethane/methanol/acetic acid/water (120:14:3:2). Product containing fractions were combined and evaporated and the residue re-evaporated with toluene. The residue was dissolved in 20 ml of dichloromethane, washed with saturated aqueous sodium bicarbonate (20 ml), dried over magnesium sulfate, filtered and evaporated to give 90 mg (67%) of 1-[4-(2-aminoethyl)phenyl]-7-anilino-3-(2,4-dichlorophenyl)-3,4-dihydropyrimido[4,5-d]pyrimidin-2(1H)-one as a white solid of melting point 117–121° C. [Mass spectrum (ESI) MH$^+$=505].

The 7-anilino-3-(2,4-dichlorophenyl)-3,4-dihydro-1-[4-(2-phthalimidoethyl)phenyl]pyrimido[4,5-d]pyrimidin-2 (1H)-one used as the starting material was prepared from ethyl 4-chloro-2-methylthio-5-pyrimidinecarboxylate and 4-[2-(tert-butyldiphenylsilyloxy)ethyl]aniline in a manner analogous to that described in Example 63. 2,4-dichloroaniline was used in place of 2-bromoaniline in step 63(f).

The 4-[2-(tert-butyldiphenylsilyloxy)ethyl]aniline was prepared as follows:

A solution containing 3 g (18 mmol) of 4-nitrophenethyl alcohol, 5.2 ml (20 mmol) of tert-butylchlorodiphenylsilane, 3.05 g (45 mmol) of imidazole and 438 mg (3.5 mmol) of N,N-dimethylaminopyridine in dimethylformamide (20 ml) was stirred under a nitrogen atmosphere at room temperature for 3 hours. The solvent was evaporated and the residue partitioned between ethyl acetate (40 ml) and 2M hydrochloric acid (40 ml). The ethyl acetate layer was separated, washed with saturated aqueous sodium bicarbonate (40 ml), dried over magnesium sulfate, filtered and evaporated to give 6.56 g of 4-[2-(tert-butyldiphenylsilyloxy) ethyl] nitrobenzene as a yellow gum.

A solution of 6.5 g (16 mmol) 4-[2-(tert-butyldiphenylsilyloxy)ethyl]nitrobenzene in methanol (30 ml) containing 750 mg of 10% palladium on carbon was hydrogenated at room temperature and atmospheric pressure for 2 hours. The catalyst was removed by filtration and the solvent evaporated to give 5.7 g of 4-[2-(tert-butyldiphenylsilyloxy)ethyl]phenylamine as a colorless liquid. [Mass spectrum (ESI) $MH^+$=376].

Example 78

A mixture of 350 mg (0.7 mmol) of 3-(2,4-dichlorophenyl)-3,4-dihydro-1-[4-(hydroxymethyl)phenyl]-7-methanesulfonyl-pyrimido[4,5-d]pyrimidin-2(1H)-one and 2 ml of aniline was heated at 120° C. for 3 hours. The reaction was cooled to room temperature then partitioned between 2M hydrochloric acid (20 ml) and dichloromethane (20 ml). The organic layer was separated, washed with saturated aqueous sodium bicarbonate (20 ml), dried over magnesium sulfate, filtered and evaporated to give 200 mg (57%) of 7-anilino-3-(2,4-dichlorophenyl)-3,4-dihydro-1-[4-(hydroxymethyl)phenyl]pyrimido[4,5-d]pyrimidin-2 (1H)-one as a yellow solid of melting point 121–125° C. [Mass spectrum (ESI) $MH^+$=492].

The 3-(2,4-dichlorophenyl)-3,4-dihydro-1-[4-(hydroxymethyl)phenyl]-7-methanesulfonyl-pyrimido[4,5-d]pyrimidin-2(1H)-one used as the starting material was prepared in a manner analogous to that described in Example 63. 2,4-dichloroaniline was used in place of 2-bromoaniline in step 63(f).

Example 79

A mixture of 200 mg (0.48 mmol) of 3-(2,4,6-trichlorophenyl)-7-methanesulfonyl-3,4-dihydro-1-methylpyrimido[4,5-d]pyrimidin-2(1H)-one and 300 mg (1.4 mmol) of 4-[2-(diethylamino)ethoxy]aniline was heated at 180° C. for 30 minutes. The mixture was cooled and the product purified by column chromatography on silica gel using dichloromethane/methanol/acetic acid/water (240:24:3:2) for the elution. Product-containing fractions were combined, evaporated and the residue evaporated with toluene. The residue was then dissolved in 40 ml of dichloromethane, washed with 40 ml of saturated aqueous sodium bicarbonate solution, dried over magnesium sulfate, filtered and evaporated to afford 45 mg (17%) of 3-(2,4,6-trichlorophenyl)-7-[4-[2-(diethylamino)ethoxy]anilino]-3,4-dihydro-1-methylpyrimido[4,5-d]pyrimidin-2(1H)-one as a white solid of melting point 142° C.

The 3-(2,4,6-trichlorophenyl)-7-methanesulfonyl-3,4-dihydro-1-methylpyrimido[4,5-d]pyrimidin-2(1H)-one used as starting material was prepared in a method analogous to that for 3-(2,6-dichlorophenyl)-7-methanesulfonyl-3,4-dihydro-1-methylpyrimido[4,5-d]pyrimidin-2(1H)-one of Example 1 using 2,4,6-trichloroaniline in place of 2,6-dichloroaniline.

Example 80

A solution of 200 mg (0.23 mmol) of 1-[3-(tert-butyldiphenylsilyloxyethyl)phenyl]-3-(2,4-dichlorophenyl)-7-[4-[2-(diethylamino)ethoxy]anilino]-3,4-dihydropyrimido [4,5-d]pyrimidin-2(1H)-one in 5 ml of tetrahydrofuran was treated with 0.5 ml (0.5 mmol) of a 1M solution of tetrabutylammonium fluoride in tetrahydrofuran. After 1 hour the mixture was evaporated and the product purified by chromatography on silica gel using dichloromethane/methanol in a ratio 20:1 as eluting solvent. Evaporation of the product-containing fractions followed by trituration of the residue with hexane and filtration gave 60 mg (42%) 3-(2,4-dichlorophenyl)-7-[4-[2-(diethylamino)ethoxy]anilino]-3,4-dihydro-1-[3-(2-hydroxyethyl))phenyl]pyrimido[4,5-d] pyrimidin-2(1H)-one as a white solid of melting point 110° C.

The 1-[3-(tert-butyldiphenylsilyloxyethyl)phenyl]-3-(2,4-dichlorophenyl)-7-[4-[2-(diethylamino)ethoxy]anilino]-3,4-dihydropyrimido[4,5-d]pyrimidin-2(1H)-one used as starting material was prepared as follows:

A mixture of 500 mg (0.7 mmol) of 1-[3-(tert-butyldiphenylsilyloxyethyl)phenyl]-3-(2,4-dichlorophenyl)-3,4-dihydro-7-methanesulfonyl-pyrimido[4,5-d]pyrimidin-2(1H)-one and 1 g (4.8 mmol) of 4-[2-(diethylamino) ethoxy]aniline was heated at 180° C. for 30 minutes. The mixture was cooled and the product purified by column chromatography on silica gel using dichloromethane/ methanol/acetic acid/water (240:24:3:2) for the elution. Product-containing fractions were combined, evaporated and the residue evaporated with toluene. The residue was then dissolved in 40 ml of dichloromethane, washed with 40 ml of saturated aqueous sodium bicarbonate solution, dried over magnesium sulfate, filtered and evaporated to afford 200 mg (33%) of 1-[3-(tert-butyldiphenylsilyloxyethyl) phenyl]-3-(2,4-dichlorophenyl)-7-[4-[2-(diethylamino) ethoxy]anilino]-3,4-dihydropyrimido[4,5-d]pyrimidin-2 (1H)-one as a yellow gum. [Mass spectrum (ESI) $MH^+$= 859].

The 1-[3-(tert-butyldiphenylsilyloxyethyl)phenyl]-3-(2,4-dichlorophenyl)-3,4-dihydro-7-methanesulfonyl-pyrimido [4,5-d]pyrimidin-2(1H)-one was prepared in a manner analogous to that for 1-[3-(2-(tert-butyldiphenylsilyloxy) ethyl)phenyl]-3-(2-chloro-6-methylphenyl)-3,4-dihydro-7-methanesulfonyl-pyrimido[4,5-d]pyrimidin-2(1H)-one of Example 53(d) using 2,4-dichloroaniline in place of 2-chloro-6-methylaniline.

Example 81

A solution of 50 mg (0.07 mmol) of 3-(2,4-dichlorophenyl)-7-[4-[2-(diethylamino)ethoxy]anilino]-3,4-dihydro-1-[3-(2-phthalimidoethyl)phenyl]pyrimido[4,5-d] pyrimidin-2(1H)-one in 5 ml of ethanol was treated with 0.5 ml of hydrazine hydrate. After 18 hours the mixture was evaporated and the product purified by column chromatography on silica gel using dichloromethane/methanol/acetic acid/water (60:18:2:3) for the elution. Product-containing fractions were combined, evaporated and the residue evaporated with toluene. The residue was then dissolved in 40 ml of dichloromethane, washed with 40 ml of saturated aqueous sodium bicarbonate solution, dried over magnesium sulfate, filtered and evaporated. The residue was triturated with pentane and filtered to give 10 mg (23%) of 3-(2,4-dichlorophenyl)-7-[4-[2-(diethylamino)ethoxy]anilino]-3,4-dihydro-1-[3-(2-aminoethyl)phenyl]pyrimido[4,5-d]pyrimidin-2(1H)-one as a white solid of melting point 108° C.

3-(2,4-dichlorophenyl)-7-[4-[2-(diethylamino)ethoxy]anilino]-3,4-dihydro-1-[3-(2-phthalimidoethyl)phenyl]pyrimido[4,5-d]pyrimidin-2(1H)-one used as starting material was prepared as follows:

a) A solution of 100 mg (0.16 mmol) of 3-(2,4-dichlorophenyl)-7-[4-[2-(diethylamino)ethoxy]anilino]-3,4-dihydro-1-[3-(2-hydroxyethyl))phenyl]pyrimido[4,5-d]pyrimidin-2(1H)-one of Example 80 in 10 ml of dichloromethane was treated with 0.05 ml (0.32 mmol) of triethylamine and 34 mg (0.2 mmol) of methanesulfonic anhydride. After 4 hours the mixture was washed with 10 ml of saturated aqueous sodium bicarbonate, dried over magnesium sulfate, filtered and evaporated to give 100 mg (90%) of 3-(2,4-dichlorophenyl)-7-[4-[2-(diethylamino)ethoxy]anilino]-3,4-dihydro-1-[3-(2-methanesulfonyloxyethyl)phenyl]pyrimido[4,5-d]pyrimidin-2(1H)-one as a white solid. [Mass spectrum (ESI) MH$^+$=699].

b) A solution of 50 mg (0.07 mmol) of 3-(2,4-dichlorophenyl)-7-[4-[2-(diethylamino) ethoxy]anilino]-3,4-dihydro-1-[3-(2-methanesulfonyloxyethyl)phenyl]pyrimido[4,5-d]pyrimidin-2(1H)-one in 5 ml of dimethylformamide was treated with 17 mg (0.09 mmol) of potassium phthalimide and the mixture was heated at 90° C. for 1 hour. The mixture was cooled and evaporated. The residue was partitioned between 20 ml of ethyl acetate and 20 ml of water. The organic phase was dried over magnesium sulfate and evaporated to yield 50 mg (95%) of 3-(2,4-dichlorophenyl)-7-[4-[2-(diethylamino)ethoxy]anilino]-3,4-dihydro-1-[3-(2-phthalimidoethyl)phenyl]pyrimido[4,5-d]pyrimidin-2(1H)-one as a white solid. [Mass spectrum (ESI) MH$^+$=750].

Example 82

50 mg (0.07 mmol) of 3-(2,4-dichlorophenyl)-7-[4-[2-(diethylamino)ethoxy]anilino]-3,4-dihydro-1-[3-(2-methanesulfonyloxyethyl)phenyl]pyrimido[4,5-d]pyrimidin-2(1H)-one of Example 81(a) was treated with 3 ml of a 33% solution of dimethylamine in ethanol and the mixture heated at 50° C. for 3 hours. The mixture was cooled and evaporated. The product was purified by column chromatography on silica gel using dichloromethane/methanol/acetic acid/water (240:24:3:2) for the elution. Product-containing fractions were combined, evaporated and the residue evaporated with toluene. The residue was then dissolved in 40 ml of dichloromethane, washed with 40 ml of saturated aqueous sodium bicarbonate solution, dried over magnesium sulfate, filtered and evaporated to afford 10 mg (22%) of 3-(2,4-dichlorophenyl)-7-[4-[2-(diethylamino)ethoxy]anilino]-3,4-dihydro-1-[3-(2-(dimethylamino)ethyl)phenyl]pyrimido[4,5-d]pyrimidin-2(1H)-one as a white solid of melting point 92° C.

Example 83

A mixture of 300 mg (0.65 mmol) of 3-(2,4-dichlorophenyl)-3,4-dihydro-7-methanesulfonyl-1-phenylpyrimido[4,5-d]pyrimidin-2(1H)-one and 400 mg (1.9 mmol) of 4-[2-(diethylamino)ethoxy]aniline was heated at 180° C. for 30 minutes. The mixture was cooled and the product purified by column chromatography on silica gel using dichloromethane/methanol/acetic acid/water (240:24:3:2) for the elution. Product-containing fractions were combined, evaporated and the residue evaporated with toluene. The residue was then dissolved in 40 ml of dichloromethane, washed with 40 ml of saturated aqueous sodium bicarbonate solution, dried over magnesium sulfate, filtered and evaporated to afford 30 mg (8%) of 3-(2,4-dichlorophenyl)-7-[4-[2-(diethylamino)ethoxy]anilino]-3,4-dihydro-1-phenylpyrimido[4,5-d]pyrimidin-2(1H)-one as a white solid of melting point 106–108° C.

The 3-(2,4-dichlorophenyl)-3,4-dihydro-7-methanesulfonyl-1-phenylpyrimido[4,5-d]pyrimidin-2(1H)-one used as starting material was prepared in a method analogous to that for 3-(2,6-dichlorophenyl)-7-methanesulfonyl-3,4-dihydro-1-phenylpyrimido[4,5-d]pyrimidin-2(1H)-one of Example 7 using 2,4-dichloroaniline in place of 2,6-dichloroaniline.

Example 84

A mixture of 370 mg (0.6 mmol) of (2-[3-[3-(2,6-dichlorophenyl)-7-methanesulfonyl-2-oxo-3,4-dihydro-2H-pyrimido[4,5-d]pyrimidin-1-yl]-phenyl]-1,1-dimethyl-ethyl)-carbamic acid tert-butyl ester and 300 mg (3.2 mmol) of aniline was heated at 140° C. for 40 minutes and cooled. 10 ml of dichloromethane and 10 ml of trifluoroacetic acid were added. After 10 minutes the mixture was evaporated and the product purified by column chromatography on silica gel using dichloromethane/methanol/acetic acid/water (240:24:3:2) for the elution. Product-containing fractions were combined, evaporated and the residue evaporated with toluene. The residue was then dissolved in 40 ml of dichloromethane, washed with 40 ml of saturated aqueous sodium bicarbonate solution, dried over magnesium sulfate, filtered and evaporated to afford, after trituration in dichloromethane/pentane, 73 mg (23%) of 1-[3-(2-amino-2-methyl-propyl)-phenyl]-3-(2,6-dichlorophenyl)-7-phenylamino-3,4-dihydro-pyrimido[4,5-d]pyrimidin-2(1H)-one as a white solid of melting point 128° C.

The (2-[3-[3-(2,6-dichlorophenyl)-7-methanesulfonyl-2-oxo-3,4-dihydro-2H-pyrimido[4,5-d]pyrimidin-1-yl]-phenyl]-1,1-dimethyl-ethyl)-carbamic acid tert-butyl ester used as starting material was prepared as follows:

a) An ice-cooled suspension of 50 g (215 mmol) of ethyl 4-chloro-2-methylthiopyrimidine-5-carboxylate in 300 ml of ethanol was treated dropwise with a solution of sodium ethoxide (prepared from 5.1 g (222 mg.atom) of sodium and 300 ml of ethanol). After 1 hour the mixture was evaporated and the residue partitioned between 400 ml of dichloromethane and 400 ml of water. The organic phase was dried over magnesium sulfate, filtered and evaporated to give 48 g (92%) of ethyl 4-ethoxy-2-methylthiopyrimidine-5-carboxylate as a colorless oil. [Mass spectrum (ESI) MH$^+$=243].

b) A dry-ice/acetone cooled solution of 15 g (62 mmol) of ethyl 4-ethoxy-2-methylthiopyrimidine-5-carboxylate in 500 ml of dichloromethane was treated dropwise with 185 ml (185 mmol) of a 1M solution of diisobutylaluminium hydride in dichloromethane. After 1 hour, 12 ml of saturated ammonium chloride was added and the mixture allowed to warm to ambient temperature. The mixture was filtered through hyflo filter aid and evaporated to afford 12.4 g (100%) of 4-ethoxy-2-methylthio-5-(hydroxymethyl) pyrimidine as a pale yellow oil. [Mass spectrum (ESI) MH$^+$=201].

c) A solution of 12.4 g (62 mmol) of 4-ethoxy-2-methylthio-5-(hydroxymethyl)pyrimidine in 500 ml of dichloromethane was treated with 54 g (620 mmol) of manganese dioxide. After 3 hours the mixture was filtered and evaporated to give 12.7 g (100%) of 4-ethoxy-2-methylthiopyrimidine-5-carboxaldehyde as a white solid. [Mass spectrum (ESI) MH$^+$=199].

d) A mixture of 12.7 g (64 mmol) of 4-ethoxy-2-methylthiopyrimidine-5-carboxaldehyde, 10.4 g (64 mmol) of 2,6-dichloroaniline and 0.6 g (3 mmol) of toluenesulfonic acid monohydrate in 400 ml of toluene was heated at reflux with azeotropic removal of water for 18 hours. The mixture was cooled and added dropwise to an ice-cooled suspension of 2.4 g (65 mmol) of lithium aluminium hydride in 400 ml of tetrahydrofuran. After 1 hour, the mixture was quenched by the cautious addition of 2.4 ml of water, 1.2 ml of 2M aqueous sodium hydroxide and 3.6 ml of water. The mixture was filtered through hyflo filter aid and evaporated to give 22 g (100%) of 5-(2,6-dichloroanilinomethyl)-4-ethoxy-2-methylthiopyrimidine as a viscous orange oil which was used without further purification. [Mass spectrum (ESI) MH$^+$=344].

e) 22 g (64 mmol) of 5-(2,6-dichloroanilinomethyl)-4-ethoxy-2-methylthiopyrimidine was treated with 100 ml of concentrated sulfuric acid and the mixture was heated at 120° C. for 20 minutes, cooled and cautiously added to 1500 ml of ice/water. The mixture was extracted with dichloromethane (3×300 ml). The combined organic phases were dried over magnesium sulfate, filtered and evaporated to afford 14 g of a brown solid. A small portion was purified by flash chromatography using ethyl acetate/isohexane in a ratio of 1:2 as eluent to give 5-(2,6-dichloroanilinomethyl)-2-methylthio-3H-pyrimidin-4-one as a white solid. [Mass spectrum (ESI) MH$^+$=316].

f) 13.6 g (43 mmol) of crude 5-(2,6-dichloroanilinomethyl)-2-methylthio-3H-pyrimidin-4-one was treated with 120 ml of phosphorus oxychloride and the mixture heated at 100° C. for 15 minutes then cooled. The mixture was evaporated and cautiously partitioned between 200 ml of ethyl acetate and 200 ml of water. The organic phase was dried over magnesium sulfate, filtered and evaporated. The product was purified by flash chromatography on silica gel eluting with diethyl ether/isohexane in a ratio of 1:9 to give 3.2 g (22%) of 4-chloro-5-(2,6-dichloroanilinomethyl)-2-methylthiopyrimidine as a pale yellow oil. [Mass spectrum (ESI) MH$^+$=334].

g) A solution of 520 mg (1.6 mmol) of 4-chloro-5-(2,6-dichloroanilinomethyl)-2-methylthiopyrimidine, 420 mg (1.6 mmol) of (2-(3-aminophenyl)-1,1-dimethyl-ethyl)-carbamic acid tert-butyl ester and 250 mg (1.7 mmol) of N,N-diethylaniline in 5 ml of dichloromethane was heated at 80° C. until the solvent had evaporated and then to 120° C. for 30 minutes and then cooled. The product was purified by flash chromatography on silica gel eluting with diethyl ether/isohexane in a ratio 1:1 to give 350 mg (39%) of (2-(3-[5-[(2,6-dichlorophenylamino)-methyl]-2-methylthiopyrimidin-4-yl-amino]-phenyl)-1,1-dimethyl-ethyl)-carbamic acid tert-butyl ester as a white solid. [Mass spectrum (ESI) MH$^+$=562].

h) A solution of 320 mg (0.6 mmol) of (2-(3-[5-[(2,6-dichlorophenylamino)-methyl]-2-methylthiopyrimidin-4-yl-amino]-phenyl)-1,1-dimethyl-ethyl)-carbamic acid tert-butyl ester in 40 ml of toluene was treated with 0.25 ml (1.8 mmol) of triethylamine and the resulting solution was added dropwise to a solution of phosgene (0.6 ml of a 20% solution in toluene) in a further 40 ml of toluene. The mixture was heated at reflux for 1 hour and then cooled. 80 ml of ethyl acetate and 80 ml of water were added. The organic phase was dried over magnesium sulfate, filtered and evaporated to give 350 mg (100%) of (2-[3-[3-(2,6-dichlorophenyl)-7-methylthio-2-oxo-3,4-dihydro-2H-pyrimido[4,5-d]pyrimidin-1-yl]-phenyl]-1,1-dimethylethyl)-carbamic acid tert-butyl ester as a white solid. [Mass spectrum (ESI) MH$^+$=588].

i) A solution of 350 mg (0.6 mmol) of (2-[3-[3-(2,6-dichlorophenyl)-7-methylthio-2-oxo-3,4-dihydro-2H-pyrimido[4,5-d]pyrimidin-1-yl]-phenyl]-1,1-dimethyl-ethyl)-carbamic acid tert-butyl ester in 10 ml of dichloromethane was treated with 400 mg (1.2 mmol) of 3-chloroperbenzoic acid (50% w/w water) and the mixture stirred for 3 hours. Dimethyl sulfoxide (0.5 ml) was added. After a further 10 minutes 10 ml of saturated aqueous sodium bicarbonate was added. The organic phase was dried over magnesium sulfate, filtered and evaporated to give 370 mg (100%) of (2-[3-[3-(2,6-dichlorophenyl)-7-methanesulfonyl-2-oxo-3,4-dihydro-2H-pyrimido[4,5-d]pyrimidin-1-yl]-phenyl]-1,1-dimethyl-ethyl)-carbamic acid tert-butyl ester as a white solid. [Mass spectrum (ESI) MH$^+$=620].

The (2-(3-aminophenyl)-1,1-dimethyl-ethyl)-carbamic acid tert-butyl ester used as starting material in part (g) above was prepared as follows:

j) A solution of 4 g (16.5 mmol) of ethyl 4-bromophenylacetate in 60 ml of diethyl ether was treated with 26 ml (36.4 mmol) of a 1.4M solution of methylmagnesium bromide in toluene/tetrahydrofuran (3:1) and the mixture heated at 40° C. for 1 hour and then cooled. 100 ml of saturated aqueous ammonium chloride were added and the phases separated. The organic phase was dried over magnesium sulfate, filtered and evaporated to give 3.5 g (93%) of 1-(4-bromophenyl)-2-methyl-propan-2-ol as a colorless oil. [Mass spectrum (ESI) MH$^+$=229].

k) A solution of 3.5 g (15.4 mmol) of 1-(4-bromophenyl)-2-methyl-propan-2-ol in 20 ml of glacial acetic acid was treated with 630 mg (15.4 mmol) of acetonitrile and cooled in ice. 10 ml of concentrated sulfuric acid was added slowly and the mixture stirred for 72 hours. The mixture was poured into 300 ml of ice/water and neutralised with potassium carbonate. The product was extracted with diethyl ether (2×250 ml). The combined organic phases were dried over magnesium sulfate, filtered and evaporated. The product was purified by recrystallisation from diethyl ether/hexane to give 3.3 g (80%) of N-[2-(4-bromophenyl)-1,1-dimethyl-ethyl]acetamide as a white solid. [Mass spectrum (ESI) MH$^+$=270].

l) An ice-cooled solution of 3.3 g (12 mmol) of N-[2-(4-bromophenyl)-1,1-dimethylethyl]-acetamide in 3 ml of concentrated sulfuric acid was treated dropwise with a mixture of 3 ml of concentrated sulfuric acid and 6 ml of 90% nitric acid. After 1 hour the mixture was cautiously added to 200 ml of ice/water and the precipitated product extracted with 150 ml of dichloromethane. The organic solution was dried over magnesium sulfate, filtered and evaporated to give 3.7 g (98%) of N-[2-(4-bromo-3-nitrophenyl)-1,1-dimethylethyl]acetamide as a white solid. [Mass spectrum (ESI) MH$^+$=315].

m) A solution of 3.5 g (11 mmol) of N-[2-(4-bromo-3-nitrophenyl)-1,1-dimethyl-ethyl]acetamide in 60 ml of ethanol was treated with 3 ml (22 mmol) of triethylamine and 500 mg of 10% palladium on charcoal. The mixture was hydrogenated at atmospheric pressure for 6 hours, filtered and evaporated. The residue was partitioned between 60 ml of ethyl acetate and 60 ml of saturated aqueous sodium bicarbonate. The organic phase was dried over magnesium sulfate, filtered and evaporated to give 1.7 g (75%) of N-[2-(3-aminophenyl)-1,1-dimethyl-ethyl]-acetamide as an orange gum. [Mass spectrum (ESI) MH$^+$=207].

n) A solution of 1.7 g (8.3 mmol) of N-[2-(3-aminophenyl)-1,1-dimethyl-ethyl]-acetamide in 20 ml of ethylene glycol was treated with 3 g (75 mmol) of sodium hydroxide and the mixture heated at 195° C. for 20 hours. The mixture was cooled and added to 150 ml of 1M aqueous sodium hydroxide saturated with sodium chloride. The product was extracted with diethyl ether (3×100 ml). The combined organic phases were dried over magnesium sulfate, filtered and evaporated to give 1.2 g (88%) of 3-(2-amino-2-methyl-propyl)-aniline as a colorless oil. [Mass spectrum (ESI) M+CH$_3$CN$^+$=206].

o) A dry-ice/acetone cooled solution of 1 g (6.1 mmol) of 3-(2-amino-2-methyl-propyl)-aniline in 30 ml of tetrahydrofuran was treated dropwise with a solution of 1.13 g (6.1 mmol) of di-tert-butyl dicarbonate in 20 ml of tetrahydrofuran. The cooling was removed after 1 hour and the mixture allowed to warm to ambient temperature and stirred at this temperature for 2 hours. 40 ml of saturated aqueous ammonium chloride was added. The organic phase was dried over magnesium sulfate, filtered and evaporated. The product was purified by flash chromatography on silica gel using diethyl ether/isohexane in a ratio of 1:1 as eluent to give 960 mg (60%) of (2-(3-aminophenyl)-1,1-dimethyl-ethyl)-carbamic acid tert-butyl ester as a white solid. [Mass spectrum (ESI) MH$^+$=265].

Example 85

A mixture of 400 mg (0.62 mmol) of (2-[3-[3-(2,6-dichlorophenyl)-7-methanesulfonyl-2-oxo-3,4-dihydro-2H-pyrimido[4,5-d]pyrimidin-1-yl]-phenyl]-2-ethyl-butyl)-carbamic acid tert-butyl ester and 600 mg (6.5 mmol) of aniline was heated at 140° C. for 45 minutes and cooled. The residue was dissolved in 20 ml of a 1:1 mixture of dichloromethane and trifluoroacetic acid. After 10 minutes the mixture was evaporated and the product purified by flash chromatography on silica gel using a gradient elution from dichloromethane/methanol 98:2 to dichloromethane/methanol 95:5. Product-containing fractions were evaporated and the residue dissolved in 4 ml of dichloromethane. The product was precipitated by the addition of pentane and subsequently filtered and dried to give 65 mg (19%) of 1-[3-(1-aminomethyl-1-ethyl-propyl)-phenyl]-3-(2,6-dichloro-phenyl)-7-phenylamino-3,4-dihydro-pyrimido[4,5-d]pyrimidin-2(1H)-one trifluoroacetate as a white solid of melting point 232° C.

The (2-[3-[3-(2,6-dichlorophenyl)-7-methanesulfonyl-2-oxo-3,4-dihydro-2H-pyrimido[4,5-d]pyrimidin-1-yl]-phenyl]-2-ethyl-butyl)-carbamic acid tert-butyl ester used as starting material was prepared using a method analogous to that described for (2-[3-[3-(2,6-dichlorophenyl)-7-methanesulfonyl-2-oxo-3,4-dihydro-2H-pyrimido[4,5-d]pyrimidin-1-yl]-phenyl]-1,1-dimethyl-ethyl)-carbamic acid tert-butyl ester of Example 84 using (2-(3-aminophenyl)-2-ethyl-butyl)-carbamic acid tert-butyl ester in place of (2-(3-aminophenyl)-1,1-dimethyl-ethyl)-carbamic acid tert-butyl ester.

The (2-(3-aminophenyl)-2-ethyl-butyl)-carbamic acid tert-butyl ester was prepared as follows:

a) A dry-ice/acetone cooled solution of 2 g (12 mmol) of 3-nitrophenylacetonitrile in 100 ml of tetrahydrofuran was treated with 4.4 g (26.5 mmol) of iodoethane, 3 g (27 mmol) of potassium tert-butoxide and 800 mg (3 mmol) of 18-crown-6. The mixture was stirred for 18 hours allowing the reaction temperature to steadily rise to ambient temperature. 100 ml of saturated aqueous ammonium chloride were added and the organic phase separated, dried over magnesium sulfate, filtered and evaporated. The product was purified by flash chromatography on silica gel using diethyl ether/hexane in a ratio of 3:7 as eluent. Product-containing fractions were evaporated to give 2.1 g (80%) of 2-ethyl-2-(3-nitro-phenyl)-butyronitrile as a pale brown oil. [Mass spectrum (ESI) MH$^+$=219].

b) A solution of 3.2 g (14.7 mmol) of 2-ethyl-2-(3-nitrophenyl)-butyronitrile in 50 ml of ethanol was treated with 350 mg of water-wet Raney nickel and the mixture heated to 60° C. 10 ml of hydrazine hydrate was added dropwise over 20 minutes and the reaction stirred for a further 1 hour at 60° C. The cooled mixture was filtered through hyflo filter aid and evaporated to give 2.5 g (90%) of 2-(3-amino-phenyl)-2-ethyl-butyronitrile as an orange oil. [Mass spectrum (ESI) MH$^+$=189].

c) A solution of 2.5 g (13 mmol) of 2-(3-amino-phenyl)-2-ethyl-butyronitrile in 30 ml of tetrahydrofuran was treated with 30 ml (30 mmol) of a 1M solution of lithium aluminium hydride in tetrahydrofuran and the mixture was heated at reflux for 2 hours then cooled. The mixture was cautiously quenched by the addition of 1 ml water, 0.5 ml 2M sodium hydroxide and 1.5 ml water and then filtered through hyflo filter aid. The filtrate was evaporated to give 0.88 g (35%) of 3-(1-aminomethyl-1-ethyl-propyl)-aniline as a pale yellow oil. [Mass spectrum (ESI) MH$^+$=193].

d) A dry-ice/acetone solution of 880 mg (4.6 mmol) of 3-(1-aminomethyl-1-ethylpropyl)-aniline in 30 ml of tetrahydrofuran was treated dropwise with a solution of 850 mg (4.6 mmol) of di-tert-butyl dicarbonate in 30 ml of tetrahydrofuran. After 1 hour the cooling was removed. After a further 2 hours 40 ml of saturated aqueous ammonium chloride were added. The organic phase was dried over magnesium sulfate, filtered and evaporated. The product was purified by flash chromatography on silica gel using diethyl ether/isohexane in a ratio 2:3 as eluent. Product-containing fractions were evaporated to afford 950 mg (71%) of (2-(3-aminophenyl)-2-ethyl-butyl)-carbamic acid tert-butyl ester as a pale orange oil. [Mass spectrum (ESI) MH$^+$=293].

Example 86

A solution of 200 mg (0.3 mmol) of 2-(3-[3-[3-(2,4-dichlorophenyl)-2-oxo-7-phenylamino-3,4-dihydro-2H-pyrimido[4,5-d]pyrimidin-1-yl]-phenyl]-propyl)-isoindole-1,3-dione in 10 ml of ethanol was treated with 1 ml of hydrazine hydrate. After 18 hours at ambient temperature the mixture was evaporated and the product purified by column chromatography on silica gel using dichloromethane/methanol/acetic acid/water (240:24:3:2) for the elution. Product-containing fractions were combined, evaporated and the residue evaporated with toluene. The residue was then dissolved in 40 ml of dichloromethane, washed with 40 ml of saturated aqueous sodium bicarbonate solution, dried over magnesium sulfate, filtered and evaporated to afford, after trituration in dichloromethane/pentane, 25 mg (16%) of 1-[3-(3-amino-propyl)-phenyl]-3-(2,4-dichlorophenyl)-7-phenylamino-3,4-dihydro-pyrimido[4,5-d]pyrimidin-2(1H)-one as a solid of melting point 120° C.

The 2-[3-[3-[3-(2,4-dichlorophenyl)-2-oxo-7-phenylamino-3,4-dihydro-2H-pyrimido[4,5-d]pyrimidin-1-yl]-phenyl]-propyl]-isoindole-1,3-dione used as starting material was prepared as follows:

a) An ice-cooled suspension of 2.1 g (53 mmol) of sodium hydride (60% w/w dispersion in mineral oil) in 120 ml of tetrahydrofuran was treated dropwise with a solution of 6.5 g (47 mmol) of 4-methoxybenzyl alcohol in 40 ml of tetrahydrofuran. After 30 minutes, a solution of 10 g (43 mmol) of ethyl 4-chloro-2-methylthiopyrimidine-5-carboxylate was added slowly. After a further 40 minutes the reaction was quenched by the cautious addition of 60 ml of saturated aqueous ammonium chloride. The mixture was separated and the organic phase dried over magnesium sulfate, filtered and evaporated to give 14.2 g (99%) of ethyl 4-(4-methoxy-benzyloxy)-2-methylthiopyrimidine-5-carboxylate as a pale yellow oil. [Mass spectrum (ESI) MH$^+$=335].

b) An ice-cooled suspension of 1.6 g (42 mmol) of lithium aluminium hydride in 150 ml of tetrahydrofuran was treated slowly with a solution of 14 g (42 mmol) of ethyl 4-(4-methoxy-benzyloxy)-2-methylthiopyrimidine-5-carboxylate in 150 ml of tetrahydrofuran. After 15 minutes the reaction was quenched by the cautious addition of 1.5 ml of water, 0.8 ml of 2M aqueous sodium hydroxide and 2.3 ml of water. The resulting suspension was filtered through hyflo filter aid. The filtered solid was washed thoroughly with tetrahydrofuran and the combined filtrate and washings evaporated. The residue was partitioned between 200 ml of dichloromethane and 100 ml of water. The organic phase was dried over magnesium sulfate and filtered. To the filtrate was added a further 100 ml of dichloromethane which was then treated with 36 g (414 mmol) of manganese dioxide. The mixture was stirred at ambient temperature for 2 hours and filtered through hyflo filter aid. The filtrate was evaporated to give 11.6 g (95%) of 4-(4-methoxy-benzyloxy)-2-methylthiopyrimidine-5-carboxaldehyde as a pale yellow oil. [Mass spectrum (ESI) MH$^+$=291].

c) A mixture of 11.6 g (40 mmol) of 4-(4-methoxy-benzyloxy)-2-methylthiopyrimidine-5-carboxaldehyde, 6.5 g (40 mmol) of 2,4-dichloroaniline and 400 mg (2.1 mmol) of toluenesulfonic acid monohydrate was heated at reflux with azeotropic removal of water for 1 hour and cooled. The mixture was added dropwise to an ice-cooled suspension of 1.5 g (40 mmol) of lithium aluminium hydride in 100 ml of tetrahydrofuran. After 1 hour the reaction was quenched by the cautious addition of 1.5 ml of water, 0.7 ml of 2M aqueous sodium hydroxide solution and 2.2 ml of water. A further 100 ml of tetrahydrofuran was added and the mixture filtered through hyflo filter aid and the filtrate evaporated to give 10.5 g (60%) of 5-(2,4-dichloroanilinomethyl)-4-(4-methoxy-benzyloxy)-2-methylthiopyrimidine as an orange-colored viscous oil which was used without further purification. [Mass spectrum (ESI) MH$^+$=436].

d) A solution of 5 g (11.5 mmol) of 5-(2,4-dichloroanilinomethyl)-4-(4-methoxy-benzyloxy)-2-methylthiopyrimidine in 30 ml of trifluoroacetic acid was heated at reflux for 20 minutes, cooled and evaporated. The product was purified by flash chromatography on silica gel using ethyl acetate/isohexane in a ratio of 1:2 as eluent. Product-containing fractions were combined and evaporated to give 1.2 g (24%) of 5-[2,4-dichloroanilinomethyl]-2-methylthio-3H-pyrimidin-4-one as a pale yellow solid. [Mass spectrum (ESI) MH$^+$=316].

e) A solution of 1.2 g (3.8 mmol) of 5-[2,4-dichloroanilinomethyl]-2-methylthio-3H-pyrimidin-4-one in 40 ml of phosphorus oxychloride was treated with 0.6 ml (3.7 mmol) of N,N-diethylaniline and the mixture was heated at 110° C. for 1 hour, cooled and evaporated. The residue was cautiously partitioned between 40 ml of ice/water and 30 ml of diethyl ether. The aqueous phase was extracted with a further 30 ml of diethyl ether and the combined organic phases were dried over magnesium sulfate, filtered and evaporated to give 1.1 g (87%) of 4-chloro-5-(2,4-dichloroanilinomethyl)-2-methylthiopyrimidine as an oil which slowly solidified to a white solid. [Mass spectrum (ESI) MH$^+$=334].

f) A solution of 180 mg (0.54 mmol) of 4-chloro-5-(2,4-dichloroanilinomethyl)-2-methylthiopyrimidine in 3 ml of dichloromethane was treated with 150 mg (0.54 mmol) of 2-[3-(3-aminophenyl)-propyl]-isoindole-1,3-dione and 85 mg (0.57 mmol) of N,N-diethylaniline and the mixture heated to 120° C. allowing the dichloromethane to evaporate and then heated at 120° C. for a further 30 minutes. The cooled mixture was subjected to flash chromatography on silica gel eluting with ethyl acetate/isohexane in a ratio of 1:2. Product-containing fractions were combined and evaporated to give 200 mg (64%) of 2-[3-[3-[5-[(2,4-dichloroanilinomethyl]-2-methylthiopyrimidin-4-yl-amino]-phenyl]-propyl]-isoindole-1,3-dione as a white solid. [Mass spectrum (ESI) MH$^+$=578].

g) A solution of 200 mg (0.35 mmol) of 2-[3-[3-[5-[(2,4-dichloroanilinomethyl]-2-methylthiopyrimidin-4-yl-amino]-phenyl]-propyl]-isoindole-1,3-dione in 10 ml of toluene was treated with 0.15 ml (1.05 mmol) of triethylamine and the resulting mixture was added dropwise to an ice-cooled solution of 0.4 ml (0.7 mmol) of phosgene (as a 20% solution in toluene) in a further 20 ml of toluene. The mixture was heated at reflux for 1 hour and then cooled. 30 ml of ethyl acetate and 30 ml of water were added. The organic phase was dried over magnesium sulfate, filtered and evaporated to give 180 mg (85%) of 2-[3-[3-[3-(2,4-dichlorophenyl)-7-methylthio-2-oxo-3,4-dihydro-2H-pyrimido[4,5-d]pyrimidin-1-yl]-phenyl]-propyl]-isoindole-1,3-dione as a white solid. [Mass spectrum (ESI) MH$^+$=604].

h) A solution of 180 mg (0.3 mmol) of 2-[3-[3-[3-(2,4-dichlorophenyl)-7-methylthio-2-oxo-3,4-dihydro-2H-pyrimido[4,5-d]pyrimidin-1-yl]-phenyl]-propyl]-isoindole-1,3-dione in 10 ml of dichloromethane was treated with 200 mg (0.6 mmol) of 3-chloroperbenzoic acid (50% w/w water) and the mixture stirred at ambient temperature for 18 hours. 0.1 ml of dimethyl sulfoxide was added. After a further 15 minutes 10 ml of dichloromethane and 20 ml of saturated aqueous sodium bicarbonate were added. The organic phase was dried over magnesium sulfate, filtered and evaporated to give 190 mg (100%) of 2-[3-[3-[3-(2,4-dichlorophenyl)-7-methanesulfonyl-2-oxo-3,4-dihydro-2H-pyrimido[4,5-d]pyrimidin-1-yl]-phenyl]-propyl]-isoindole-1,3-dione as a white solid. [Mass spectrum (ESI) MH$^+$=636].

i) A mixture of 190 mg (0.3 mmol) of 2-[3-[3-[3-(2,4-dichlorophenyl)-7-methanesulfonyl-2-oxo-3,4-dihydro-2H-pyrimido[4,5-d]pyrimidin-1-yl]-phenyl]-propyl]-isoindole-1,3-dione and 1 ml of aniline was heated at 140° C. for 35 minutes and then cooled. The mixture was added to 40 ml of 2M aqueous hydrochloric acid and the precipitated product was filtered off, washed with 2M aqueous hydrochloric acid, then with water and finally dried to give 200 mg (100%) of 2-[3-[3-[3-(2,4-dichlorophenyl)-2-oxo-7-phenylamino-3,4-dihydro-2H-pyrimido[4,5-d]pyrimidin-1-yl]-phenyl]-propyl]-isoindole-1,3-dione as a pale brown solid. [Mass spectrum (ESI) MH$^+$=649].

The 2-[3-(3-aminophenyl)-propyl]-isoindole-1,3-dione used as starting material in part (f) was prepared as follows:

j) To a solution of 15 g (100 mmol) of sodium iodide in 120 ml of acetone was added 3 g (11 mmol) of N-(3-bromopropyl)phthalimide and the mixture was heated at reflux for 30 minutes. The cooled mixture was filtered and evaporated. The residue was partitioned between 50 ml of diethyl ether and 50 ml of water. The organic phase was dried over magnesium sulfate, filtered and evaporated to give 2.6 g (75%) of N-(3-iodopropyl)phthalimide as a white solid. [Mass spectrum (ESI) MH$^+$=316].

k) Under an atmosphere of nitrogen, a stirred suspension of 1.6 g (24 mg.atom) of zinc dust (<10 micron diameter) in 20 ml of dimethylformamide was treated with 0.11 ml (1.2 mmol) of 1,2-dibromoethane and the mixture was heated to 60° C. then allowed to cool to room temperature. The heating and cooling was repeated twice more. 0.04 ml (0.24 mmol) of chlorotrimethylsilane was added and the mixture stirred at ambient temperature for 30 minutes. The mixture was then treated with 1.26 g (4 mmol) of N-(3-iodopropyl) phthalimide and the resulting suspension stirred for 30 minutes at ambient temperature and then heated at 35° C. for 1 hour and cooled. To the mixture were then added sequentially 750 mg (3 mmol) of 1-iodo-3-nitrobenzene, 60 mg (0.06 mmol) of tris(dibenzylideneacetone)dipalladium and 70 mg (0.23 mmol) of tri(o-tolyl)phosphine and the resulting mixture stirred at ambient temperature for 1 hour. The suspension was filtered and the filtrate diluted with 50 ml of ethyl acetate, washed twice with 40 ml of water, dried over magnesium sulfate, filtered and evaporated. The product was purified by flash chromatography on silica gel using ethyl acetate/isohexane in a ratio of 1:2 as eluent. Product containing fractions were combined and evaporated to give 190 mg (20%) of 2-[3-(3-nitrophenyl)-propyl]-isoindole-1,3-dione as a pale pink solid. [Mass spectrum (ESI) MH$^+$=311].

l) A solution of 190 mg (0.6 mmol) of 2-[3-(3-nitrophenyl)-propyl]-isoindole-1,3-dione in 20 ml of ethanol was treated with 50 mg of 10% palladium on charcoal and shaken in an atmosphere of hydrogen for 2 hours. The mixture was filtered and the filtrate evaporated to give 120 mg (71%) of 2-[3-(3-aminophenyl)-propyl]-isoindole-1,3-dione as a yellow oil. [Mass spectrum (ESI) MH$^+$=281].

Example 87

A solution of 58 mg (0.1 mmol) of 7-anilino-3-(2,4-dichlorophenyl)-3,4-dihydro-1-[3-(2-methanesulfonyloxyethyl)phenyl]-pyrimido[4,5-d]pyrimidin-2(1H)-one (prepared in Example 74) and 0.5 ml of diethylamine in 2 ml of ethanol was heated at 50° C. for 3 hours. The reaction mixture was evaporated and the crude material purified by flash chromatography on silica gel, eluting with 5% methanol in dichloromethane. Product containing fractions were combined and evaporated to give 16 mg (28%) of 7-anilino-3-(2,4-dichlorophenyl)-1-[3-[2-(diethylamino) ethyl]phenyl]-3,4-dihydro-pyrimido[4,5-d]pyrimidin-2(1H)-one as an off-white solid of melting point 186° C. [Mass spectrum (ESI) MH$^+$=561].

Example 88

A solution of 58 mg (0.1 mmol) of 7-anilino-3-(2,4-dichlorophenyl)-3,4-dihydro-1-[3-(2-methanesulfonyloxyethyl)phenyl]-pyrimido[4,5-d]pyrimidin-2(1H)-one (prepared in Example 74) and 0.5 ml of morpholine in 2 ml of ethanol was heated at 50° C. for 3 hours. The reaction mixture was evaporated and the crude material was purified by flash chromatography on silica gel, eluting with 5% methanol in dichloromethane. Product containing fractions were combined and evaporated to give 26 mg (45%) of 7-anilino-3-(2,4-dichlorophenyl)-3,4-dihydro-1-[3-(2-morpholinoethyl)phenyl]-pyrimido[4,5-d]pyrimidin-2(1H)-one as a pale yellow solid of melting point 118° C. [Mass spectrum (ESI) MH$^+$=575].

Example 89

A solution of 58 mg (0.1 mmol) of 7-anilino-3-(2,4-dichlorophenyl)-3,4-dihydro-1-[3-(2-methanesulfonyloxyethyl)phenyl]-pyrimido[4,5-d]pyrimidin-2(1H)-one (prepared in Example 74) and 100 mg of piperazine in 2 ml of ethanol was heated at 50° C. for 3 hours. The reaction mixture was evaporated and the crude material purified by flash chromatography on silica gel, eluting with dichloromethane/methanol/acetic acid/water (90:18:3:2). Product containing fractions were combined and evaporated. The residue was dissolved in 10 ml of dichloromethane, washed with saturated aqueous sodium bicarbonate (10 ml), dried over magnesium sulfate, filtered and evaporated to give 3 mg (5%) of 7-anilino-3-(2,4-dichlorophenyl)-3,4-dihydro-1-[3-[2-(1-piperazinyl)-ethyl]phenyl]-pyrimido[4,5-d]pyrimidin-2(1H)-one as a white solid of melting point 126° C. [Mass spectrum (ESI) MH$^+$=574].

Example 90

A mixture of 100 mg (0.26 mmol) of 3-(2,6-dichlorophenyl)-3,4-dihydro-7-(methanesulfonyl)-1-methylpyrimido[4,5-d]pyrimidin-2(1H)-one (prepared in Example 1f) and 2 ml of furfurylamine was stirred at room temperature overnight under a nitrogen atmosphere. The reaction mixture was partitioned between dichloromethane (10 ml) and 2M hydrochloric acid (10 ml), and the organic phase washed with saturated aqueous sodium bicarbonate (10 ml), dried over magnesium sulfate, filtered and evaporated. The crude material was triturated with diethyl ether/hexane, filtered and dried under vacuum to give 80 mg (76%) of 3-(2,6-dichlorophenyl)-3,4-dihydro-7-(furan-2-yl-methylamino)-1-methylpyrimido[4,5-d]pyrimidin-2(1H)-one as a pale brown solid of melting point 150° C. (with decomposition). [Mass spectrum (ESI) MH$^+$=404].

Example 91

A solution of 320 mg (0.47 mmol) of 1-[3-(2-tert-butyldiphenylsilyloxyethyl)-phenyl]-3-(1-oxy-pyridin-3-yl)-7-phenylamino-3,4-dihydro-pyrimido[4,5-d]pyrimidin-2(1H)-one in dry tetrahydrofuran (5 ml) was treated with 0.425 ml (0.425 mmol) of tetrabutylammonium fluoride (1M solution in tetrahydrofuran) then stirred at room temperature for 2 hours. The solvent was evaporated and the crude material purified by flash chromatography on silica gel, eluting with 10% methanol in dichloromethane. Product containing fractions were combined and evaporated to give 95 mg (61%) of 1-[3-(2-hydroxyethyl)-phenyl]-3-(1-oxy-pyridin-3-yl)-7-phenylamino-3,4-dihydro-pyrimido[4,5-d]pyrimidin-2(1H)-one as a pale brown solid of melting point 220° C. (with decomposition). [Mass spectrum (ESI) MH$^+$=455].

The 1-[3-(2-tert-butyldiphenylsilyloxyethyl)-phenyl]-3-(1-oxy-pyridin-3-yl)-7-phenylamino-3,4-dihydro-pyrimido[4,5-d]pyrimidin-2(1H)-one used as the starting material was prepared in a manner analogous to that described in Example 53, using 3-aminopyridine in place of 2-chloro-6-methyl-aniline (53b) and 3 molar equivalents of 3-chloroperbenzoic acid instead of 2 (53d).

Example 92

A solution of 320 mg (0.47 mmol) of 1-[3-(2-tert-butyldiphenylsilyloxyethyl)-phenyl]-3-(furan-2-yl-methyl)-7-phenylamino-3,4-dihydro-pyrimido[4,5-d]pyrimidin-2(1H)-one in dry tetrahydrofuran (5 ml) was treated with 0.6 ml (0.6 mmol) of tetrabutylammonium fluoride (1M solution in tetrahydrofuran) then stirred at room temperature for 2 hours. The solvent was evaporated and the crude material purified by flash chromatography on silica gel, eluting with 4:1 ethyl acetate/hexane. Product containing fractions were combined and evaporated to give 170 mg (82%) of 3-(furan-2-yl-methyl)-1-[3-(2-hydroxyethyl)-phenyl]-7-phenylamino-3,4-dihydro-pyrimido[4,5-d]pyrimidin-2(1H)-one as a pale pink solid of melting point 195° C. [Mass spectrum (ESI) MH$^+$=442].

The 1-[3-(2-tert-butyldiphenylsilyloxyethyl)-phenyl]-3-(furan-2-yl-methyl)-7-phenylamino-3,4-dihydro-pyrimido[4,5-d]pyrimidin-2(1H)-one used as the starting material was prepared in a manner analogous to that described in Example 53, using furfurylamine in place of 2-chloro-6-methyl-aniline (53b).

What is claimed is:

1. A bicyclic heterocycle, comprising a compound of the formula

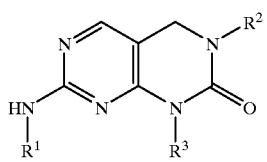

(I)

wherein

R$^1$ is hydrogen, lower alkyl, aryl, aryl-lower alkyl, heteroaryl, heteroaryl-lower alkyl, lower cycloalkyl or lower cycloalkyl-lower alkyl, R$^2$ is lower alkyl, aryl, aryl-lower alkyl, heteroaryl, heteroaryl-lower alkyl, lower cycloalkyl or lower cycloalkyl-lower alkyl, and R$^3$ is hydrogen, lower alkyl, aryl, aryl-lower alkyl, heteroaryl, heteroaryl-lower alkyl, lower cycloalkyl, lower cycloalkenyl or lower cycloalkyl-lower alkyl, wherein each said aryl and heteroaryl is independently unsubstituted or substituted by one or more groups selected from the group consisting of halogen, lower alkyl, lower alkoxy, lower-alkoxy lower alkyl, trifluoromethyl, hydroxy, hydroxy lower-alkyl, carboxylic acid, carboxylic ester, nitro, amino, phenyl, —Z—NR$^4$R$^5$ and —Z—OR$^6$;

wherein Z is —O(CH$_2$)$_n$— in which n is 2, 3 or 4, or —(CH$_2$)$_m$— in which m is 1, 2, 3 or 4 and wherein each hydrogen of the —(CH$_2$)$_m$ chain is present or independently replaced by lower-alkyl, hydroxy lower-alkyl or lower-alkyloxy lower-alkyl; and R$^4$ and R$^5$ are each individually hydrogen or lower alkyl or R$^4$ and R$^5$ together with the nitrogen atom to which they are attached are a 4-, 5- or 6-membered saturated or partially unsaturated or 5- or 6-membered aromatic heterocyclic group which contains one or more hetero atoms selected from nitrogen, sulfur and oxygen and which is optionally substituted by lower alkyl, lower alkoxy and/or oxo and/or which is optionally benzfused; and R$^6$ is hydrogen or lower-alkyl;

or, if the compound is basic a pharmaceutically acceptable salt thereof with an acid, and if the compound is acidic a pharmaceutically acceptable salt thereof with a base.

2. The heterocycle according to claim 1 wherein the compound is of the formula

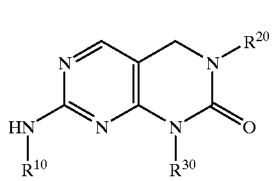

(Ia)

wherein R$^{10}$ is lower alkyl, aryl or aryl-lower alkyl, R$^{20}$ is aryl and R$^{30}$ is hydrogen, lower alkyl, aryl or aryl-lower alkyl.

3. The heterocycle according to claim 2 wherein the compound is of the formula

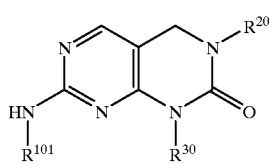

(Iai)

wherein R$^{101}$ is aryl and R$^{20}$ and R$^{30}$ have the significance given in claim 2.

4. The heterocycle according to claim 3, wherein R$^{101}$ is unsubstituted or substituted phenyl.

5. The heterocycle according to claim 4, wherein R$^{101}$ is unsubstituted phenyl.

6. The heterocycle according to claim 4, wherein R$^{101}$ is phenyl substituted by —O(CH$_2$)$_n$R$^4$R$^5$, wherein n is 2 and R$^4$ and R$^5$ are both ethyl.

7. The heterocycle according to claim 4, wherein R$^{20}$ is halophenyl.

8. The heterocycle according to claim 4, wherein R$^{20}$ is 2,6-dichlorophenyl.

9. The heterocycle according to claim 2, wherein R$^{30}$ is phenyl substituted by a group of the formula —Z—NR$^4$R$^5$.

10. The heterocycle according to claim 1 wherein the compound is of the formula

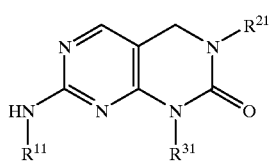

(Ib)

wherein R$^{11}$ is lower alkyl, R$^{21}$ is aryl and R$^{31}$ is heteroaryl-lower alkyl.

11. The heterocycle according to claim 10, wherein R$^{11}$ is isopropyl.

12. The heterocycle of claim 11, wherein R$^{21}$ is halophenyl.

13. The heterocycle according to claim 10, wherein R$^{21}$ is halophenyl.

14. The heterocycle of claim 1, 1-[3-(2-Aminoethyl)phenyl]-7-anilino-3-(2,6-dichlorophenyl)-3,4-dihydro-pyrimido[4,5-d]pyrimidin-2(1H)-one.

15. A process for the manufacture of the heterocycle according to claim 1, which process comprises (a) reacting a compound of the formula

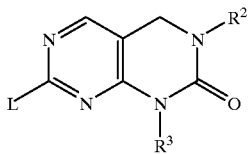
(II)

wherein $R^2$ and $R^3$ have the significance given in claim 1, with the proviso that any hydroxy, amino or carboxylic acid group present may be in protected form, and L signifies benzyl sulfonyl or lower alkanesulfonyl, with an amine of the formula $R^1$—$NH_2$ (III)

wherein $R^1$ has the significance given in claim 1, with the proviso that any hydroxy, amino or carboxylic acid group present may be in protected form, and, where required, converting a protected hydroxy or protected amino or protected carboxylic acid group present in the reaction product into a free hydroxy or free amino or free carboxylic acid group, or b) for the manufacture of a compound of formula I in which $R^1$ represents hydrogen, cleaving off the aryl-methyl group from a compound of formula I in which $R^1$ signifies aryl-methyl, and c) if desired, converting a basic compound of formula I obtained into a pharmaceutically acceptable salt with an acid, or converting an acidic compound of formula I obtained into a pharmaceutically acceptable salt with a base.

16. A compound of the formula

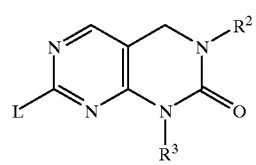
(II)

wherein $R^2$ and $R^3$ have the significance given in claim 1, with the proviso that any hydroxy, amino or carboxylic acid group present may be in protected form, and L signifies benzyl sulfonyl or lower alkanesulfonyl.

* * * * *